United States Patent
Abou-Elkacem et al.

(10) Patent No.: US 12,274,759 B2
(45) Date of Patent: Apr. 15, 2025

(54) AFFIBODY PROTEINS SPECIFIC FOR B7-H3 (CD276)

(71) Applicants: THE BOARD OF TRUSTEES OF THE LELAND STANFORD JUNIOR UNIVERSITY, Stanford, CA (US); REGENTS OF THE UNIVERSITY OF MINNESOTA, Minneapolis, MN (US)

(72) Inventors: Lotfi Abou-Elkacem, Houston, TX (US); Juergen Karl Willmann, Stanford, CA (US); Benjamin J. Hackel, Edina, MN (US); Lawrence Arthur Stern, Monrovia, CA (US); Patrick Samuel Lown, Minneapolis, MN (US); Amelie Margarete Marianne Lutz, Stanford, CA (US); Rakesh Kumar Bam, Menlo Park, CA (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 875 days.

(21) Appl. No.: 17/267,733

(22) PCT Filed: Aug. 22, 2019

(86) PCT No.: PCT/US2019/047764
§ 371 (c)(1),
(2) Date: Feb. 10, 2021

(87) PCT Pub. No.: WO2020/041626
PCT Pub. Date: Feb. 27, 2020

(65) Prior Publication Data
US 2021/0340257 A1 Nov. 4, 2021

Related U.S. Application Data

(60) Provisional application No. 62/872,122, filed on Jul. 9, 2019, provisional application No. 62/721,974, filed on Aug. 23, 2018.

(51) Int. Cl.
*A61K 38/16* (2006.01)
*A61K 9/00* (2006.01)
*A61K 47/68* (2017.01)
*A61K 49/22* (2006.01)
*A61P 35/00* (2006.01)
*C07K 16/28* (2006.01)
*A61K 39/00* (2006.01)

(52) U.S. Cl.
CPC .......... *A61K 49/221* (2013.01); *A61K 9/0019* (2013.01); *A61K 47/6849* (2017.08); *A61K 49/223* (2013.01); *A61P 35/00* (2018.01); *C07K 16/2827* (2013.01); *A61K 2039/505* (2013.01); *C07K 2317/92* (2013.01); *C07K 2318/20* (2013.01)

(58) Field of Classification Search
None
See application file for complete search history.

(56) References Cited

U.S. PATENT DOCUMENTS

| 2016/0031967 A1 | 2/2016 | Ekblad et al. |
| 2017/0240637 A1 | 8/2017 | Cheung et al. |

OTHER PUBLICATIONS

Lowe, Derek; "Not alphafold's fault." blog "In the Pipeline" entry of Sep. 7, 2022.*
Guo, Haiwei H. et al; "Protein tolerance to random amino acid change." PNAS (2004) 101(25) p. 9205-9210.*
Yampolsky, Lev Y. and Stoltzfus, Arlin; "The exchangeability of amino acids in proteins." Genetics (2005) 170 p. 1459-1472.*
Bam, Rakes et al; "Affibody indocyanine green based contrast agent for photoacoustic and fluorescece molecular imaging of b7-h3 expression in breast cancer." Bioconj. Chem. (May 2019) 30 p. 1677-1689.*

* cited by examiner

*Primary Examiner* — Fred H Reynolds
(74) *Attorney, Agent, or Firm* — Mueting Raasch Group

(57) ABSTRACT

Affibody polypeptides that specifically bind to B7-H3 are provided. Exemplary anti-B7-H3 affibodies are provided. The affibody polypeptides specifically recognize and bind to B7-H3 with high affinity. The affibodies can be conjugated to contrast agents, including without limitation microbubbles for contrast-enhanced ultrasound imaging

26 Claims, 14 Drawing Sheets
Specification includes a Sequence Listing.

Sequences of Affibody Proteins (SEQ ID NO:1) AC2:  AEAKYAKEKIFAVGEIYWLPNLTHGQIMAFIAALNDDPSQSSELLSEAKKLNDSQAPK
(SEQ ID NO:2) AC9:  AEAKYAKEKIIALSEIIALSEIIWLPNLTHGQIMAFIAALNDDPSQSSELLSEAKKLNDSQAPK
(SEQ ID NO:3) AC12: AEAKYAKEKIAALSEIIWLPNLTHGQIMAFIAALNDDPSQSSELLSEAKKLNDSQAPK
(SEQ ID NO:4) AC16: AEAKYAKEKVHALSEIIWLPNLTHGQIMAFIAALNDDPSQSSELLSEAKKLNDSQAPK

FIG. 1

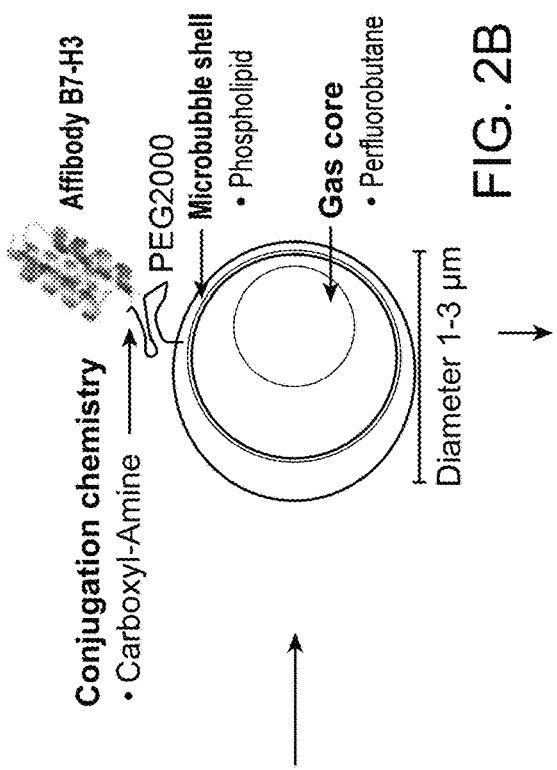
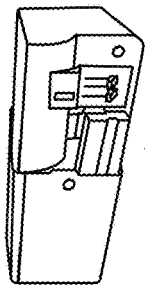
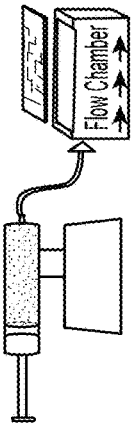
FIG. 2A
FIG. 2B
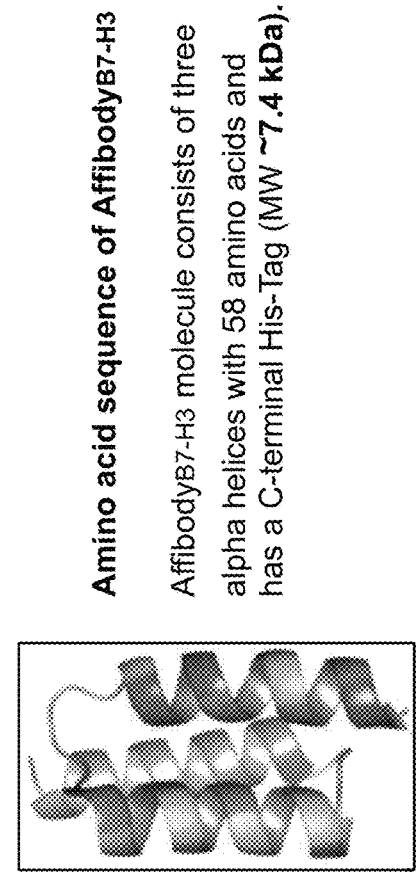
FIG. 2C
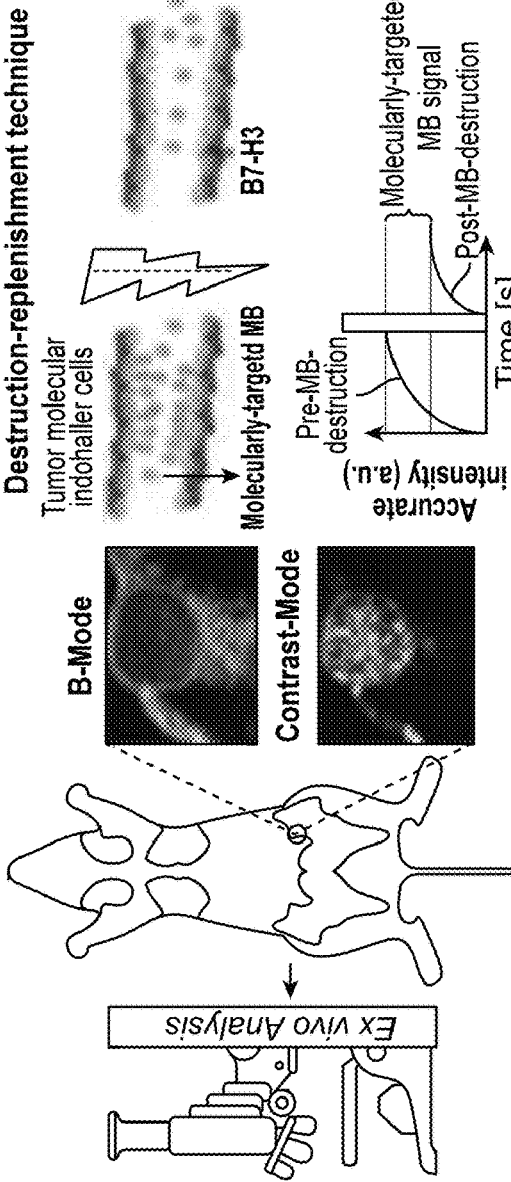
FIG. 2D

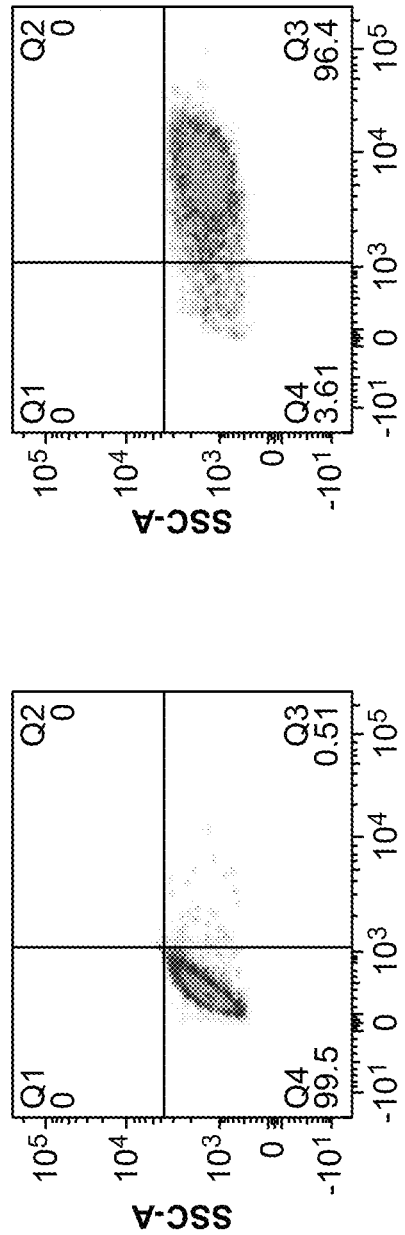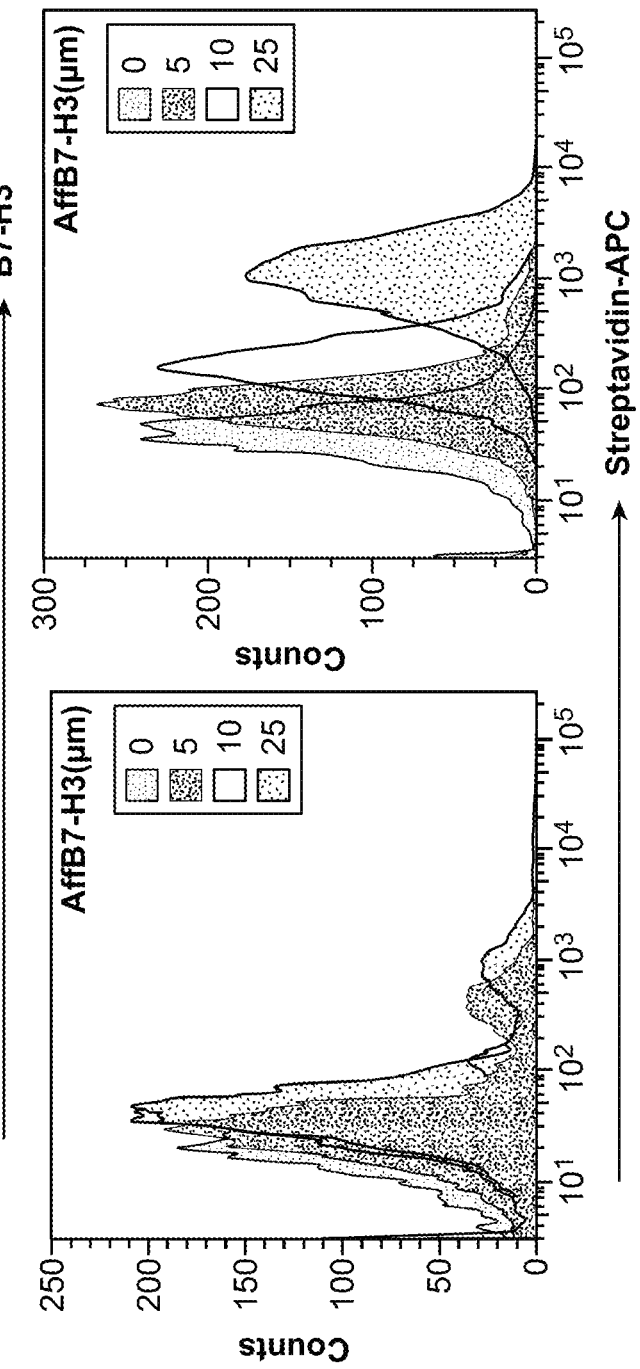
FIG. 3

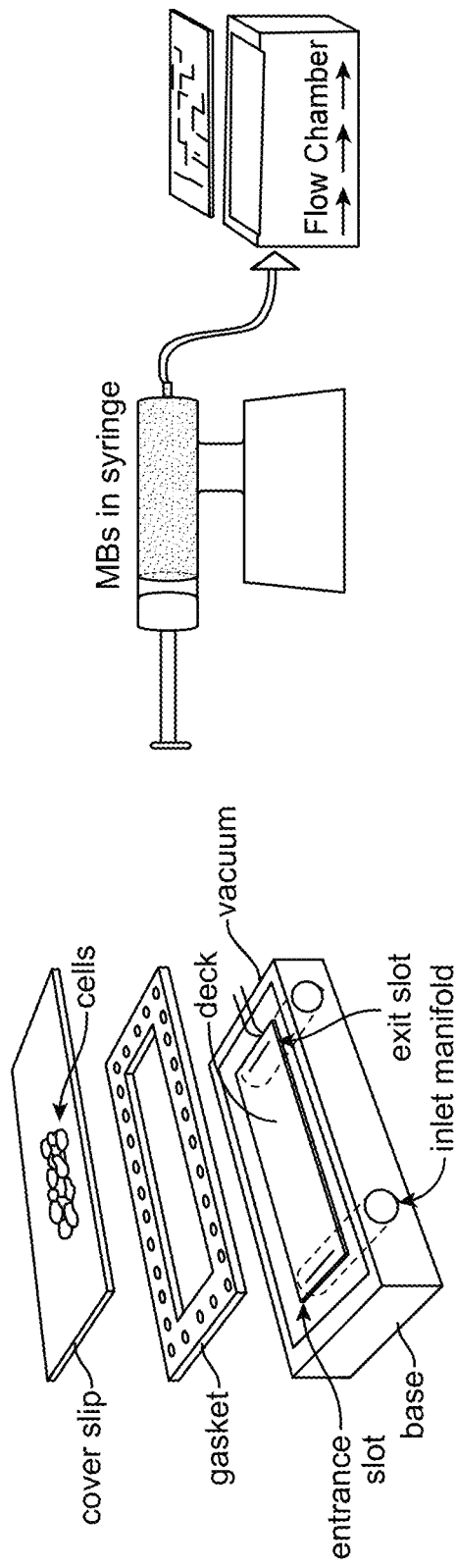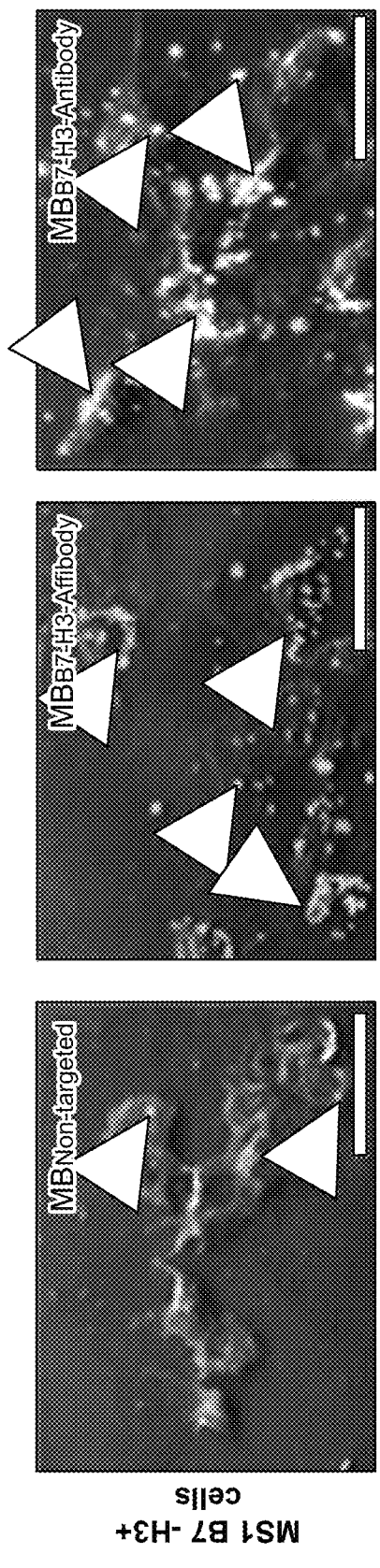
FIG. 4

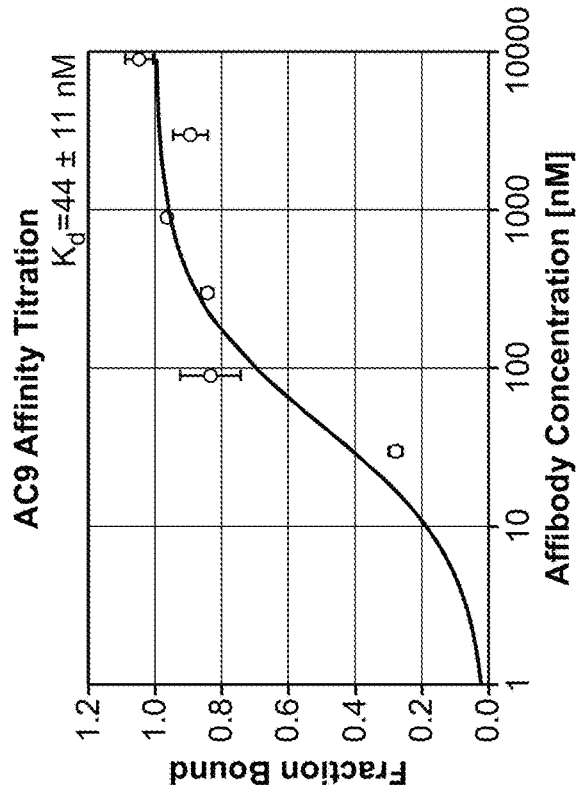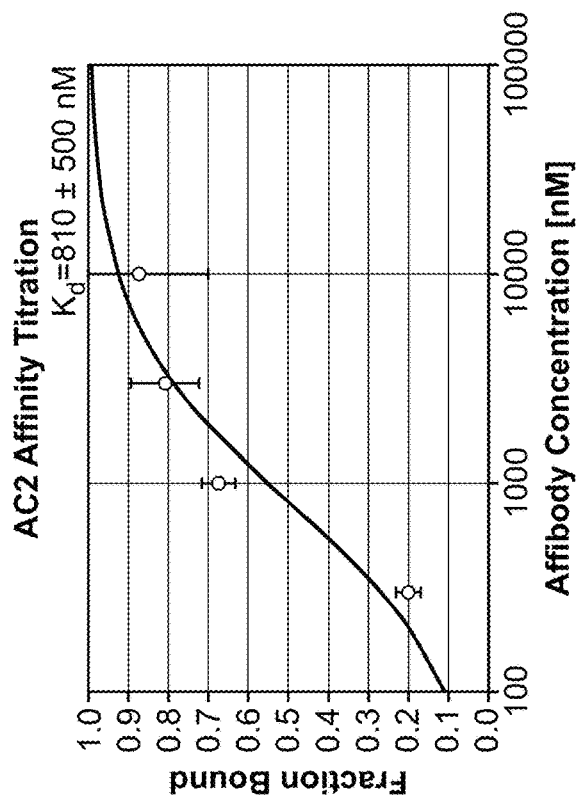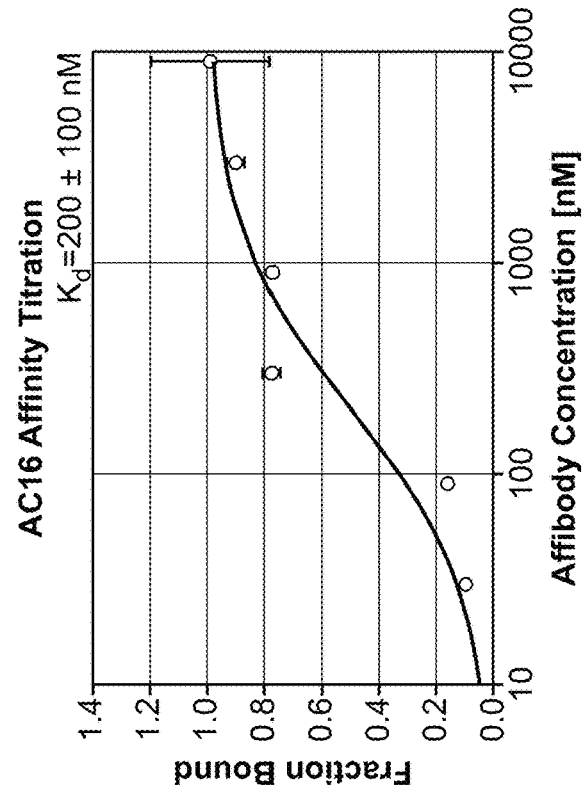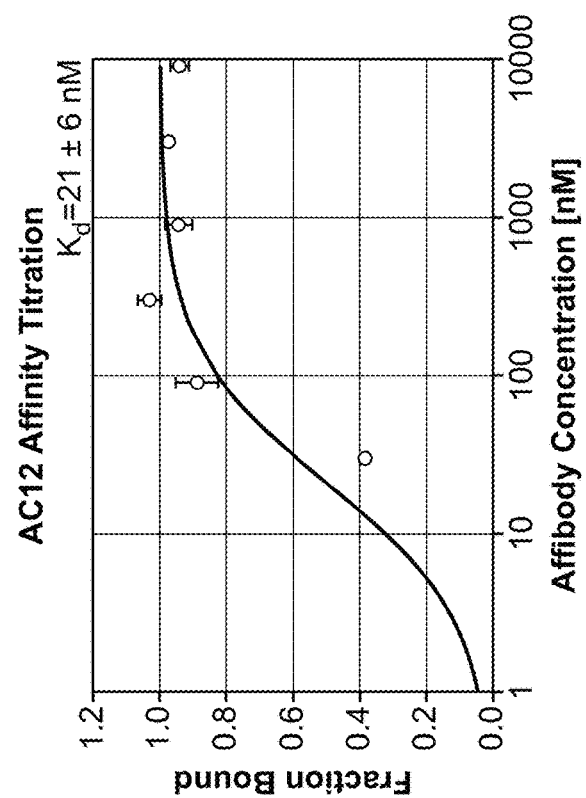
FIG. 7

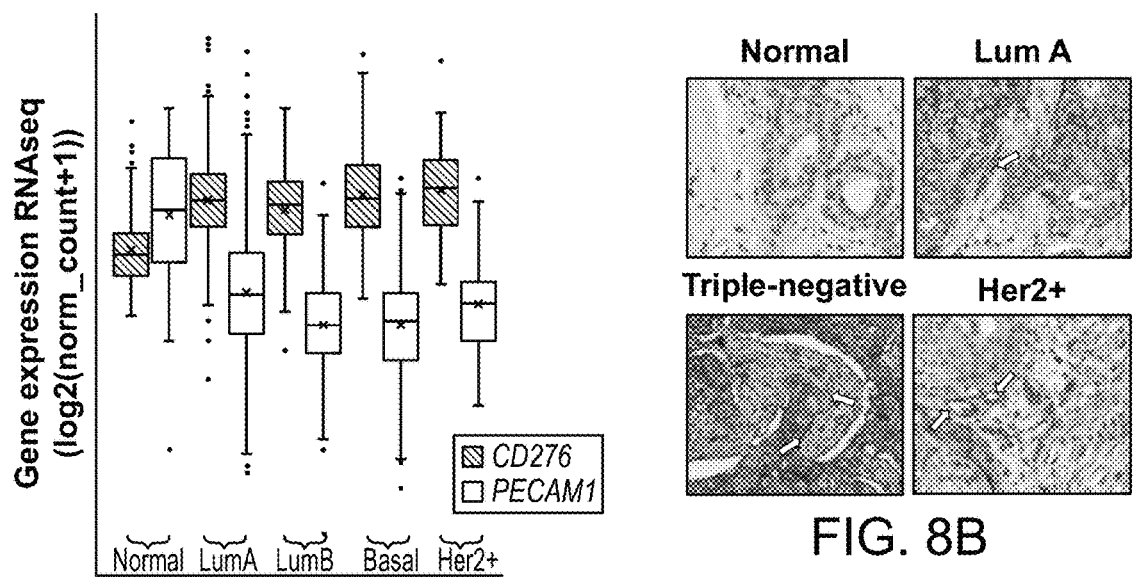
FIG. 8A
FIG. 8B
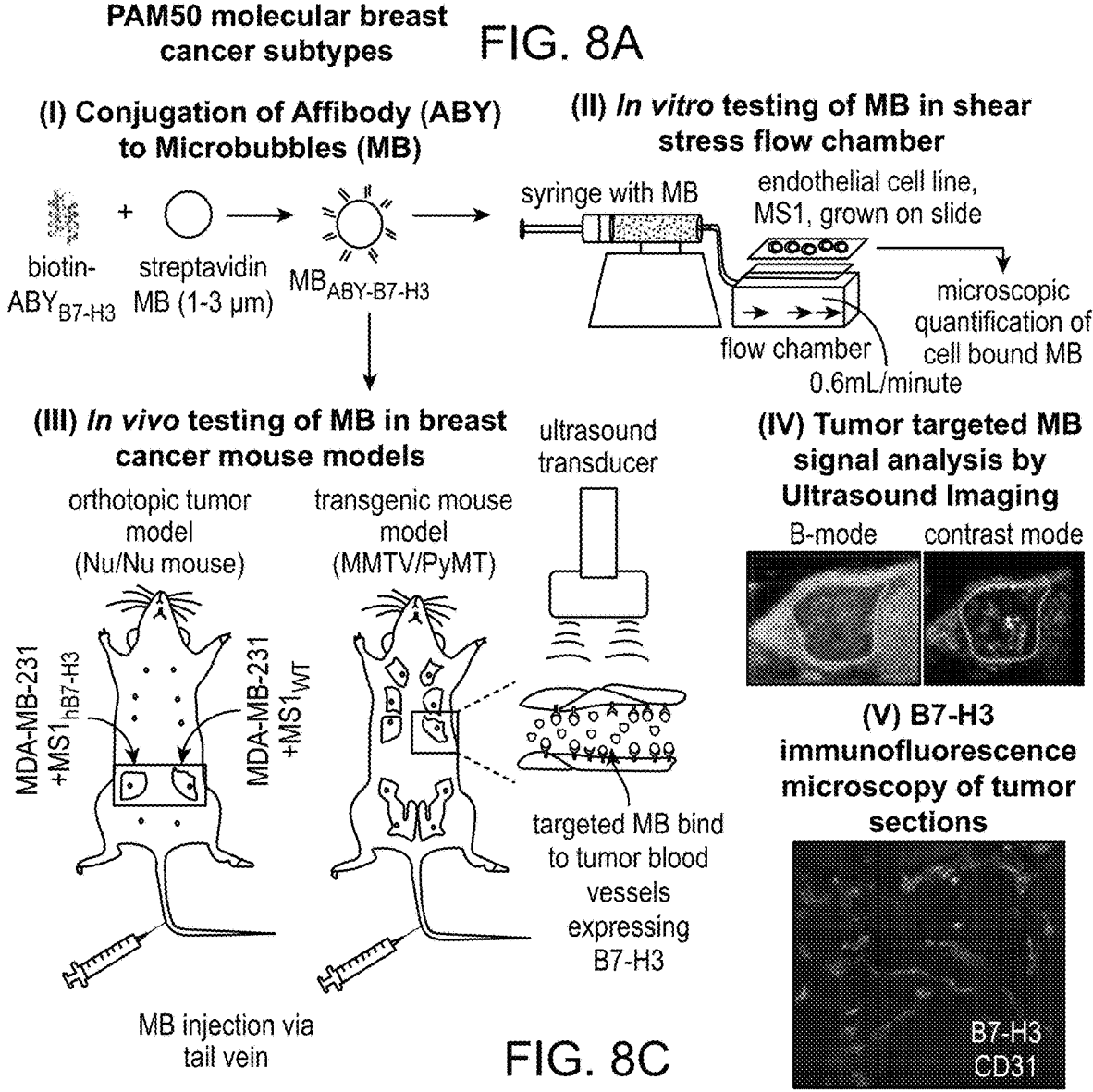
FIG. 8C

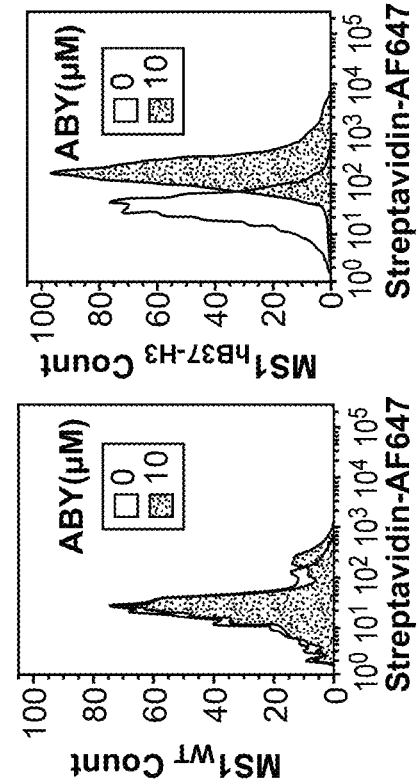
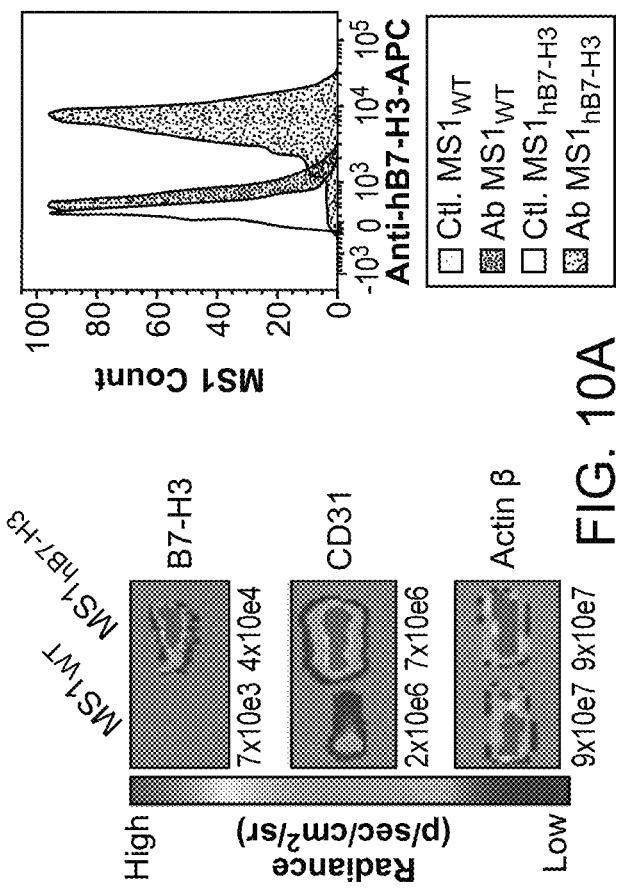
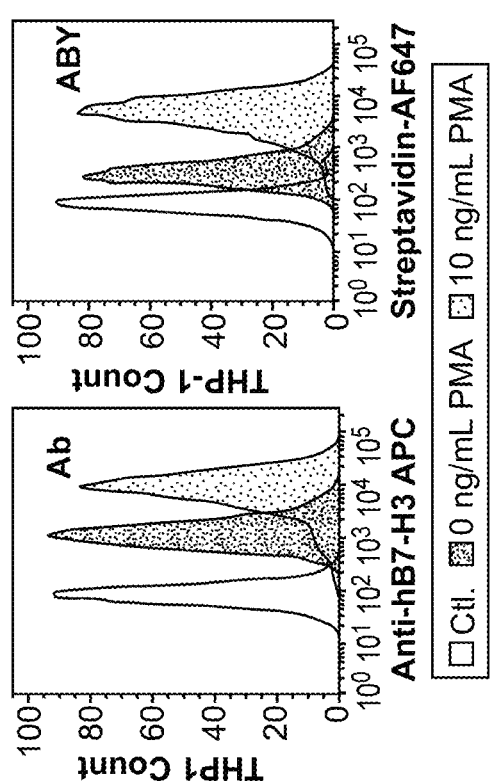
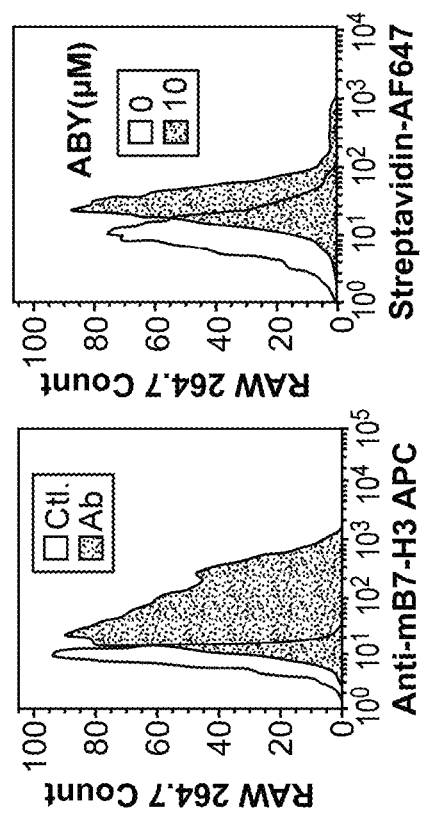
FIG. 10A
FIG. 10B
FIG. 10C
FIG. 10D

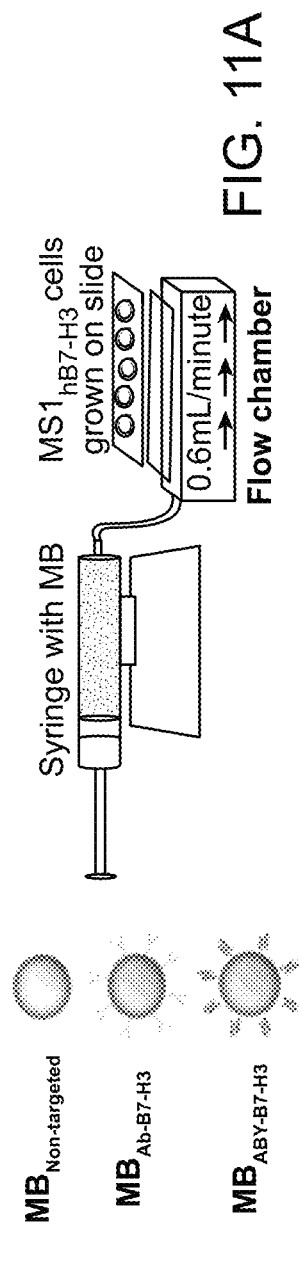
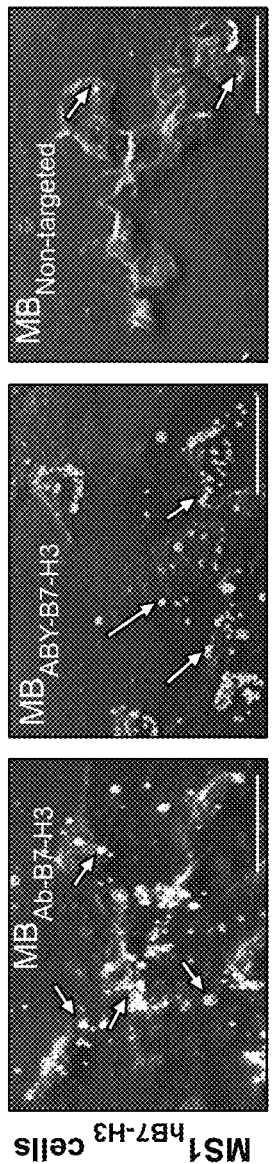
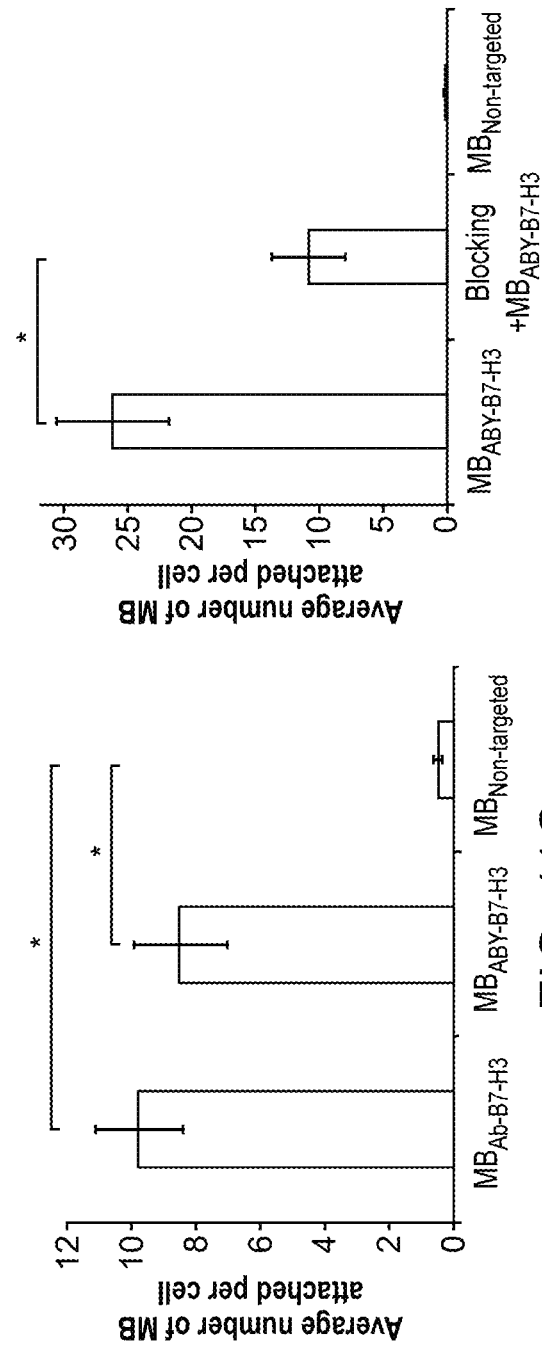
FIG. 11A
FIG. 11B
FIG. 11C
FIG. 11D

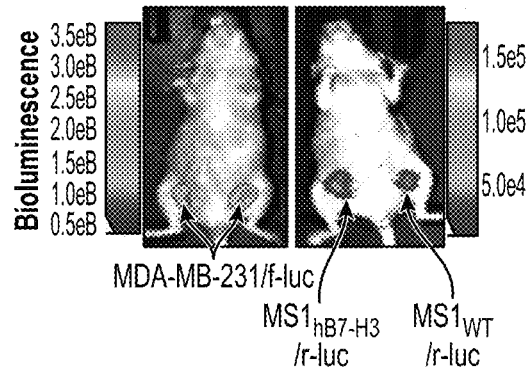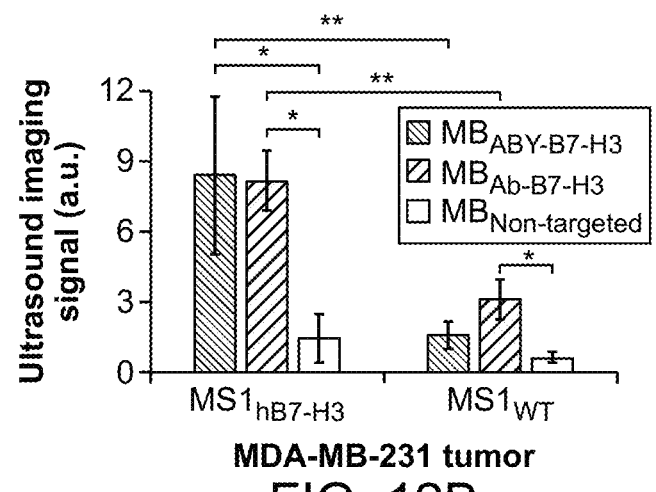
FIG. 12A  FIG. 12B
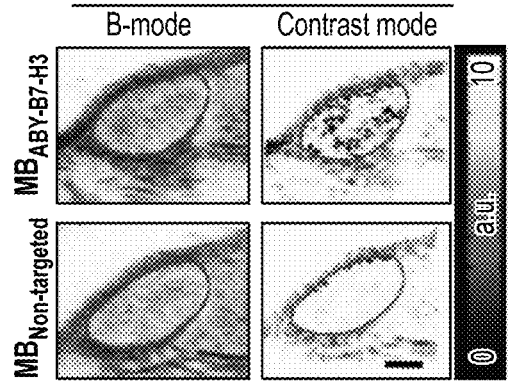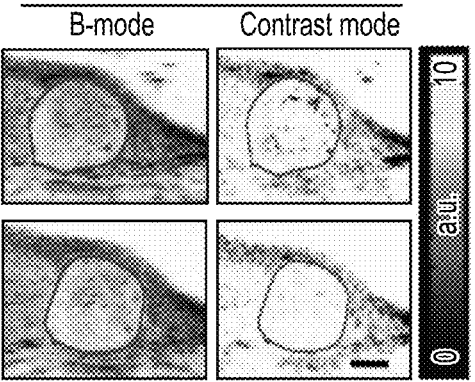
FIG. 12C
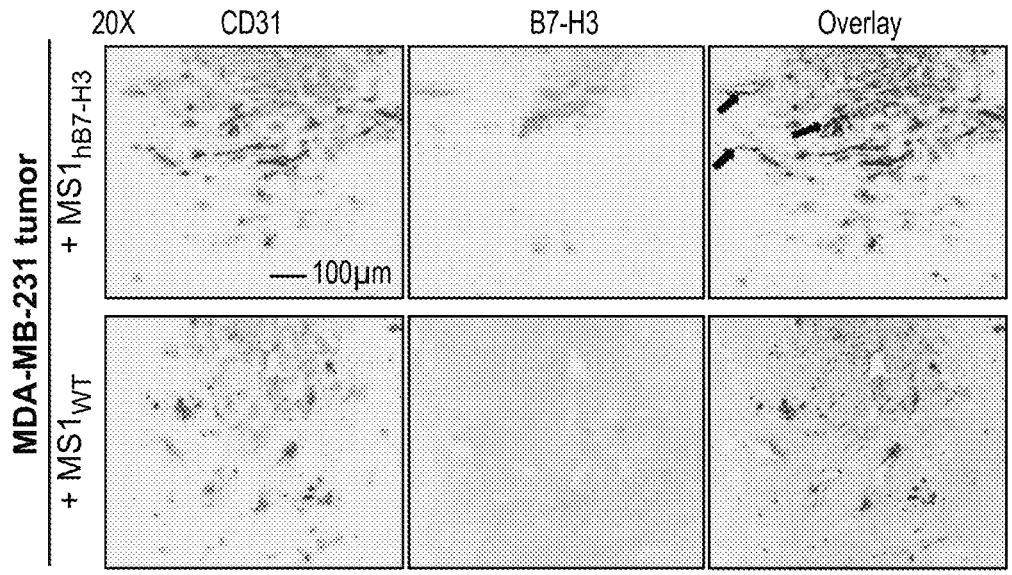
FIG. 12D

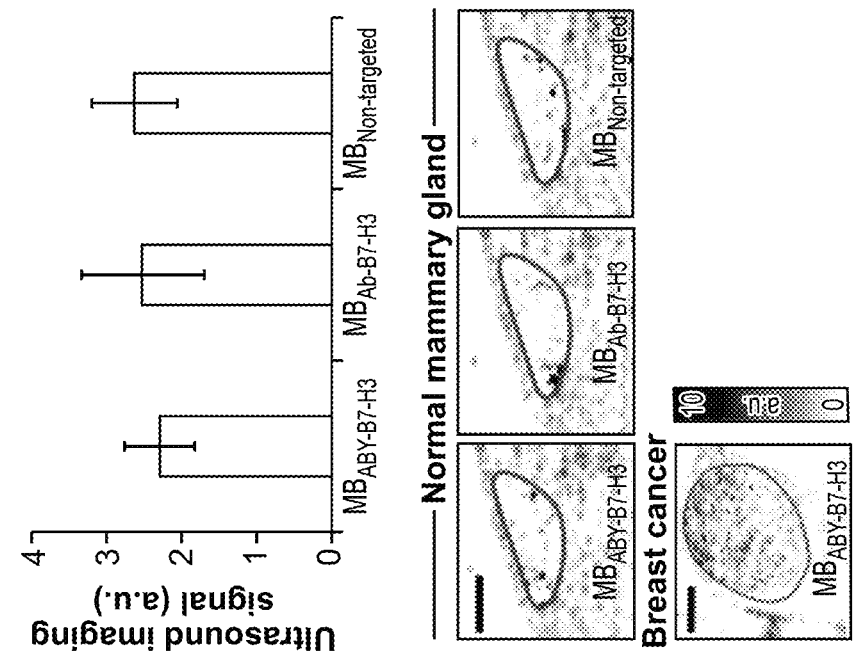
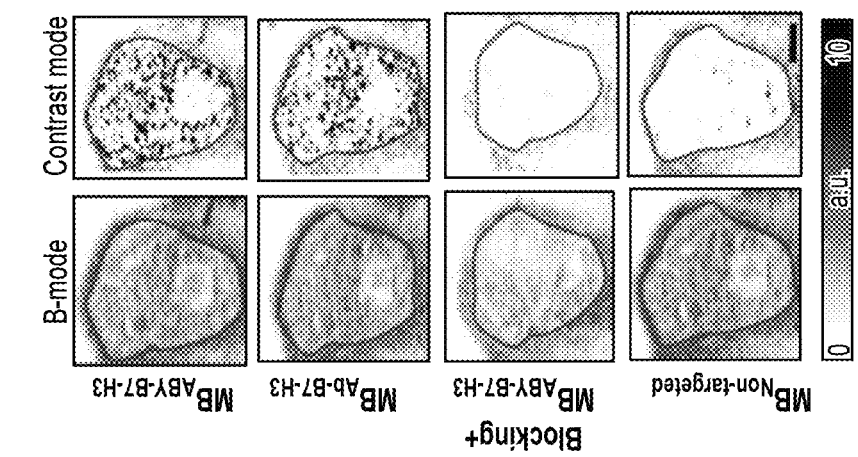
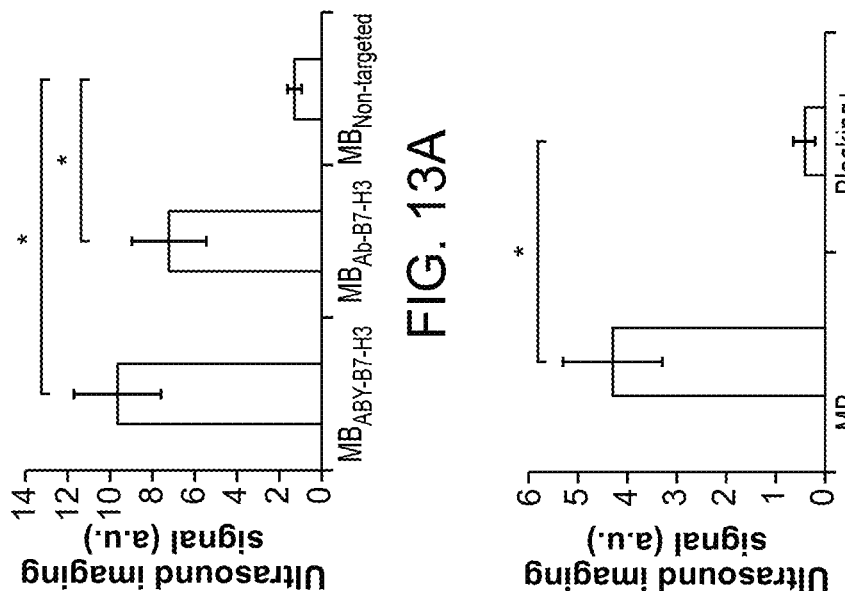
FIG. 13A
FIG. 13B
FIG. 13C
FIG. 13D

AFFIBODY PROTEINS SPECIFIC FOR B7-H3 (CD276)

CROSS REFERENCE

This application is the § 371 U.S. National Stage of International Application No. PCT/US2019/047764, filed Aug. 22, 2019, which claims the benefit of U.S. Provisional Application No. 62/721,974, filed Aug. 23, 2018, and U.S. Provisional Application No. 62/872,122, filed Jul. 9, 2019, the disclosure of each of which is incorporated herein by reference in its entirety.

GOVERNMENT SUPPORT

This invention was made with Government support under contract CA213544, awarded by the National Institutes of Health. The Government has certain rights in the invention.

SEQUENCE LISTING

This application contains a Sequence Listing electronically submitted via EFS-Web to the United States Patent and Trademark Office as an ASCII text file entitled "S17-486_STAN- 1483_Sequence_Listing_ST25.txt" having a size of 12,192 bytes and created on Mar. 20, 2024. The information contained in the Sequence Listing is incorporated by reference herein.

BACKGROUND

The development of imaging biomarkers and quantitative imaging techniques has been identified as a major research priority in oncology. In the clinical as well as the preclinical research setting, imaging biomarkers can be a measure of anatomical, physiologicalifunctional or molecular characteristics. Of particular interest are cell surface markers that provide an indication of the presence of cancer, for example solid tumor lesions. Certain biomarkers can also find utility as a therapeutic target for tumor-associated antigens (TAA), and in immunotherapy. A protein of interest in this respect is B7-H3 (CD276), which is a glycoprotein expressed on antigen-presenting cells (APC). It is often induced in human tumors and its overexpression is closely correlated with survival, prognosis or tumor grade. B7-H3 provides a target for imaging and treatment, since its expression is mainly restricted to the tumor; and it is also of interest as a target for immune therapy.

Immune evasion is a crucial adaptation in the progression of cancer. A feature in immune evasion is immune checkpoints regulation. For example, programmed cell death-1 (PD-1) is an immune inhibitory receptor expressed on T-cells and B-cells. PD-1 interacts with two ligands, PD-(B7-H1) or PD-L2 (B7-DC), which exert a range of roles in the immunoregulation of T-cells. Activation of PD-1 by its ligand is responsible for downregulating activity of T-cells. Blockade of PD-1 enhances activity of effector T-cells in the tumor microenvironment; and as an adaptive modification, cancer cells express PD-L1, which allows them to escape immune detection and destruction. Inhibiting the interaction of PD-1 with its ligands increases antitumor immunity.

Other members of the PD-1 family can have a similar influence on tumor growth and microenvironment modification, including B7-H3, which is a member of the B7/CD28 superfamily that has a number of similarities with PD-L1. It has been proposed to have costimulatory and coinhibitory functions that are dependent on the contexts of tumor specificity, microenvironmental factors and signaling intensity. In addition to its role as an immune regulator, B7-H3 has been implicated in enhancing metastasis and angiogenesis in cancer.

The prevalence of B7-H3 overexpression across lung, breast, brain, kidney, and prostate cancers make B7-H3 a target for developing combination immunotherapeutic treatments. Specific cancers reported to upregulate B7-H3 include without limitation non-small cell lung cancer (NSCLC), breast cancer, prostate cancer, renal cell carcinomas, and a number of brain cancers, including gliomas and medulloblastomas. Increased expression of B7-H3 is frequently associated with increased metastasis and progression of the cancer.

Breast cancer is the second leading cause of cancer-related deaths and the most common site for cancer development at 30% of all new cancer cases in women in the United States, with an estimated 41,760 deaths and 268,600 new cases diagnosed in 2019. This incidence is expected to grow by more than 50% by 2030. Detection during early, localized stages of the disease significantly improves survival with five-year survival rates of 99% compared to 27% for in highly advanced stages.

Mammography is the first line method in breast cancer screening programs, which creates two-dimensional images based on x-ray attenuation. Clinically detected lesions have a median size of 2.6 cm, while those found with mammography screening have a median size of 1.5 cm. Digital mammogram analyses between 2000-2012 showed increased screening sensitivity and deaths averted compared to plain-film mammography. Despite these improvements, mammograms often result in over-diagnosis and unnecessary biopsies with one-half of the women experiencing false-positives during the course of multiple screenings. Increased frequency of mammography exams along with factors such as age and breast density lower the overall specificity of screening and result in more false-positives. Women with extremely or heterogeneously dense breasts have a four- to six-fold greater chance of developing breast cancer compared to women with fatty breasts. Furthermore, women with dense breasts frequently have worse prognosis due to late-stage disease detection. Mammographically dense tissues decrease detection of malignant lesions because dense tissues appear opaque, which can obscure or mimic malignant lesions and to some extent calcifications, and mislead even experienced radiologists.

Currently, alternative imaging tools are applied whenever mammography alone is insufficient for radiological detection of breast lesions. Digital tomosynthesis, a form of 3D mammography, is able to detect breast cancer with high accuracy but shows significant variabilities in sensitivity and specificity based on breast density. MRI is used to screen high-risk candidates with familial history of breast cancer, but is expensive, not readily available, and has potential health concerns such as deposition of gadolinium in the brain. At present, supplemental screening by ultrasound (US) is recommended to assess suspicious lesions observed in mammograms and is available for high-risk patients with contraindications to MRI. It has been shown that US detects more cancer than mammography alone in women with dense breast tissue, and is widely available, portable, non-invasive, cost-effective, and free of ionizing radiation. However, US is associated with a high false-positive rate, low positive predictive value (5.6-8.6%), and a sensitivity as low as 17%.

Contrast-mode US (also called contrast-enhanced US) using molecularly-targeted contrast microbubbles (MB) that bind to proteins expressed on the tumor neovasculature is an emerging imaging approach with large potential for improving diagnostic accuracy and characterization of focal breast lesions. MB are gas filled lipid- or protein-stabilized particles and enhance US imaging contrast due to differential response to changes in acoustic pressure. Gas filled MB that are a few micrometers in size (1-4 μm) remain within the blood vessel lumen, which renders molecularly-targeted MB uniquely suitable for US imaging of molecular markers expressed on the neovasculature. It is of high importance to identify molecular markers that are differentially expressed on tumor-associated neovasculature compared to that of normal tissue or benign breast lesions. B7-H3 (CD276) is a promising breast cancer US molecular imaging target. B7-H3, a T-cell modulator, has highly specific over-expression on vascular endothelial cells of different sub-types of human breast cancer and high- grade DCIS compared to normal breast tissue and benign lesions. B7-H3 is a cell-surface receptor protein and highly correlated with tumor drug resistance, metastasis, and immune-regulation.

Monoclonal antibodies produced by hybridoma technology have primarily been used as target-binding ligands to functionalize the surface of MB although small protein scaffolds have been used as well for other targets. Previously, an anti-B7-H3 antibody-conjugated MB was utilized for preclinical US molecular imaging of mammary tumors. In this study, US molecular imaging signal with antibody-conjugated MB was shown to be highly correlated with pathology-based B7-H3 expression in the mammary tumors. Unfortunately, antibody-based ligands can be problematic for clinical translation due to inefficient and random conjugation, costly and time-consuming production, and potential immune response, especially with repeated dosing.

Improved agents for imaging are of great interest and are provided herein.

SUMMARY

Affibody polypeptides that specifically bind to B7-H3 are provided. Exemplary anti-B7-H3 affibodies are provided in any of SEQ ID NO:1-4, and variants thereof as described herein. The polypeptide ligands were developed using a yeast displayed affibody library and directed evolution. The affibody polypeptides specifically recognize and bind to soluble B7-H3, and also specifically recognize and bind to B7-H3 expressed on a cell surface. B7-H3 is expressed or overexpressed on a variety of human tumors, including pediatric solid tumors and adult carcinomas. Examples of cancers that express or overexpress B7-H3 include, but are not limited to, neuroblastoma, Ewing's sarcoma, rhabdomyosarcoma, and prostate, ovarian, colorectal, and lung cancers. B7-H3 is also expressed in tumor vasculature and is a tumor endothelial marker. The affibody may be cross-reactive with non-human B7-H3, e.g. with mouse B7-H3 protein.

B7-H3 is a target for cancer detection, including, for example, breast carcinoma, and has been identified and evaluated as a marker to distinguish benign and precursor lesions from malignant lesions with high diagnostic accuracy. Therefore, the development of specific imaging agents for identification of B7-H3 expressing cells can improve diagnosis of cancer. It has also been found that B7-H3 is upregulated in the tumor microenvironment.

In some embodiments, an anti-B7-H3 affibody is conjugated to an imaging moiety, for example a contrast agent moiety, a radionuclide moiety, a fluorescent moiety, and the like to provide a B7-H3-specific imaging agent. The imaging agent may be provided as a composition comprising an effective unit dose for imaging, and a pharmaceutically acceptable excipient. The composition may be suitable for clinical use, e.g. administration to a human subject. In some embodiments such an imaging agent is contacted with a tissue, e.g. human tissue, suspected of having a cancerous lesion, e.g. a solid tumor, micro-metastases, etc. Cancers of interest include, without limitation, breast carcinomas. The contacting may be performed in vivo or in vitro, e.g. on biopsy samples. The imaging agent is allowed to bind to B7-H3 present in the tissue, and the presence of bound imaging agent is then detected by a suitable means, e.g, ultrasound, radiography, positron-emission tomography, magnetic resonance imaging, direct or indirect visual inspection, etc., where increased presence of the bound imaging agent relative to normal tissue is indicative of the presence of a cancerous lesion.

In some embodiments an anti-B7-H3 affibody as described herein is conjugated to a microbubble (MB) for diagnostic, theranostic and/or therapeutic use. Conjugation may utilize covalent or non-covalent linkage, including without limitation affinity reagents such a biotin/avidin, biotin streptavidin, etc.; catalyst-free strain-promoted alkyne-azide cycloaddition (SPAAC) chemistry, cysteine-maleimide conjugation; and the like. The microbubble may comprise any microbubble composition suitable for clinical or pre-clinical use, typically a gas-filled microbubble with a shell or lipid, protein, polymer, surfactant, etc. Microbubbles find use, for example, as contract agents for clinical ultrasound imaging. Such a clinical grade MB contrast agent is suitable for breast cancer screening, and additionally provides for ultrasonic detection of mammographically occult malignancy in women with dense breast tissue.

In some embodiments, methods are provided for imaging cancer with an anti-B7-H3 affibody-MB composition. Targeting of a MB contrast agent by functionalization with surface conjugation of anti-B7-H3 affibody significantly increases attachment of the MB to endothelial cells under flow shear stress conditions. In some embodiments the cancer is breast cancer. In some embodiments the imaging is performed on mammographically dense breast tissue. As shown herein, such compositions may provide for sensitive and specific imaging of blood vessel-associated ultrasound (US) imaging signals in tumors, but not in the normal mammary glands. In such methods, an effective dose of the MB composition is administered for imaging, e.g. parenterally. Clinical ultrasound imaging frames are captured shortly after administration, e.g. after about 15 minutes, after about 10 minutes, and usually within about 1 to 10 minutes after administration. The images are processed for detection of the imaging signal and correlation with cancerous lesions.

In some embodiments, an anti-B7-H3 affibody is conjugated to a therapeutic moiety, for example a protein toxin, a chemotherapeutic drug, a radionucleide, an immune effector domain, e.g. an Fc sequence; and the like, to provide a therapeutic agent. The therapeutic agent may be provided as a composition comprising an effective unit dose for administration to an individual, and a pharmaceutically acceptable excipient. The composition may be suitable for clinical use, e.g. administration to a human subject. In some embodiments such therapeutic agent is administered to an individual for treatment of a cancer that expresses B7-H3. Cancers of interest for treatment include, without limitation, breast carcinomas. The therapy may be provided in a combination therapy, e.g. with a checkpoint inhibitor, chemotherapeutic agent, radiotherapy, and the like. The development of a theranostic approach using drug loaded B7-H3 affibody may increase therapeutic efficacy.

In other embodiments, anti-B7-H3 affibodies are provided for modulating B7-H3 immune function, where such affibodies are optionally conjugated, for example, to a moiety such as albumin, albumin binding protein, Fc, PEG, and the like to increase the serum half-life. The therapeutic agent may be provided as a composition comprising an effective unit dose for administration to an individual, and a pharmaceutically acceptable excipient. The composition may be suitable for clinical use, e.g. administration to a human subject.

Further embodiments of the invention provide related anti-B7-H3 binding affibodies, nucleic acids encoding such affibodies, recombinant expression vectors, host cells, populations of cells, conjugates, kits, and pharmaceutical compositions relating to the polypeptides disclosed herein.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1. Amino acid sequence of anti-B7-H3 affibodies, shown as SEQ ID NO:1, SEQ ID NO:2 SEQ ID NO:3, and SEQ ID NO:4, respectively.

FIG. 2A-2D. Overview of the design study.

FIG. 3. Affibody binding to B7-H3 expressed on MS-1 endothelial cells.

FIG. 4. Cell culture flow chamber cell attachment studies of affibody-conjugated microbubbles.

FIG. 7. Affibody titrations conducted on MS-1 endothelial cells.

FIG. 8. B7-H3 expression and study design of US molecular imaging in breast cancer, (A) Box-plots analysis of CD276 (B7-H3) and PECAM1 (CD31) RNA-Seq expression data from TOGA breast invasive carcinoma database showing increased CD276 expression in LumA (n=434), LumB (n=194), Basal (n=142), and Her2+(n=67) subtypes compared to normal breast tissue samples (n=119). In contrast, PECAM1 expression is higher in normal tissue compared to all breast cancer subtypes. (B) Representative immunohistochemical staining of B7-H3 in normal and breast cancer tissue sections showing its expression in structures morphologically resembling blood vessels (arrows) and cancer cells, Extensive staining of clinical samples was shown previously (21). (C) Experimental overview including (I) microbubble (MB) targeting with affibody (ABY), (II) in vitro MB cell attachment assay, (III and IV) in vivo US imaging of mammary tumors in an orthotopic and transgenic breast cancer mouse models, and (V) B7-H3 expression on the neovasculature of both mouse models was confirmed by ex vivo immunofluorescence.

FIG. 11, $MB_{ABY-B7-H3}$ specifically bind to $MS1_{hB7-H3}$ cells under flow shear stress condition. (A) Schematic diagram of MB bio-functionalization with $ABY_{B7-H3}$ ($MB_{ABY-B7-H3}$) or anti-B7-H3 antibody ($MB_{Ab-B7-H3}$) and flow chamber cell attachment of $MS1_{hB7-H3}$ cells grown on glass slides. $MBN_{Non-targeted}$ served as control. (B) Representative photomicrographs (20× magnification) of $MS1_{hB7-H3}$ cells showing increased attachment (white arrows) of $MB_{Ab-B7-H3}$ and $MB_{ABY-B7-H3}$ compared to MBNon-targeted. Arrows point to the attached MB on cells. Scale bar represents 10 μm. (C) Bar graph quantification showing significantly higher $MB_{Ab-B7-H3}$ (*p<0.0001) and $MB_{ABY-B7-H3}$ (*p<0.0001) counts per $MS1_{hB7-H3}$ cell compared to $MB_{Non-targeted}$. (D) Significant decrease (*p<0.009) in $MB_{ABY-B7-H3}$ HS attachment after B7-H3 receptor blocking with free $ABY_{B7-H3}$ (5 μg/mL) one hour prior to cell attachment assay in comparison to the non-blocking group, Moderate changes in cell density across experimental sets (e.g. C vs. D) impact the magnitude of captured MB, but each experimental set is performed with cells cultured in parallel for rigorous comparison within a set.

FIG. 12. $MB_{ABY-B7-H3}$ enhances US molecular imaging signal of human MDA-MB-231 orthotopic breast tumors in mice. (A) Representative bioluminescence imaging signal of nude mice co-implanted with human breast cancer cell line, MDA-MB-231/f-luc (firefly luciferase reporter; left image), and MS1/r-luc endothelial cells (renilla luciferase reporter; right image). Left flank tumor consisted of $MS1_{hB7-H3}$/r-luc cells and right flank tumor consisted of $MS1_{WT}$/r-luc cells. (B) US molecular imaging signal of tumors with the administration of various MB constructs was quantified and analyzed within the same tumor group (*) or between the two tumor groups (**). Imaging within the tumor group co-implanted with $MS1_{hB7-H3}$ cells, $MB_{ABY-B7-H3}$ (*p<0.04; n=12) and $MB_{Ab-B7-H3}$ (*p<0.001; n=6) produced significantly higher imaging signal compared to $MB_{Non-targeted}$ (n=14). Between the two tumor groups co-implanted with either $MS1_{hB7-H3}$ or $MS1_{WT}$ cells, US molecular imaging signal with $MB_{ABY-B7-H3}$ (p<0.05) and $MB_{ABY-B7-H3}$ (p<0.008) was also significantly higher in tumors co-implanted with $MS1_{hB7-H3}$ cells compared to tumors co-implanted with $MS1_{WT}$ cells. B7-H3 imaging signal in the tumors with $MS1_{WT}$ cells was low with all the MB constructs with $MB_{Ab-B7-H3}$ producing a significantly higher (*p<0.001) signal compared to $MB_{Non-targeted}$. (C) Representative B-mode and contrast mode US images of tumors with $MB_{ABY-B7-H3}$ and $MB_{Non-targeted}$. B-mode images were used to draw region of interest (green outline) around the tumor for signal quantification in contrast mode. Scale bar represents 1 mm. (D) Individual immunofluorescence channels and composite images showing staining of extracted tumor sections confirming integration of $MS1_{hB7-H3}$ cells in tumor blood vessels by anti-human B7-H3 (red) and anti-mouse CD31 (green) co-staining. Tumors co-implanted with $MS1_{hB7-H3}$ but not the $MS1_{WT}$ cells stain for human B7-H3 in CD31-positive endothelial cells as indicated by white arrows. Scale bar represents 100 µm.

FIG. 13. $MB_{ABY-B7-H3}$ enhances US molecular imaging signal of mouse mammary tumors in a transgenic breast cancer model. (A) Quantification of US molecular imaging signal of mammary tumors with the administration of various MB constructs. B7-H3 targeted imaging with $MB_{ABY-B7-H3}$ (*p<0.0002; n=47) or $MB_{ABY-B7-H3}$ (*p<0.001; n=45) produced significantly higher imaging signal in tumors compared to $MB_{Non-targeted}$ (n=41). (B) Quantification of US molecular imaging signal with $MB_{ABY-B7-H3}$ before and after in vivo B7-H3 receptor blocking overnight with 150 µg free $ABY_{B7-H3}$ (n=5). (C) Representative B-mode and contrast mode US images of tumors with administration of various MB constructs including $MB_{ABY-B7-H3}$ imaging post receptor blocking. B-mode images were used to draw region of interest (green border) around the tumor for signal quantification by contrast mode. Scale bar represents 1 mm. (D) Top panel: Quantification of normal mammary gland US imaging signal with $MB_{ABY-B7-H3}$ (n=14) and $MB_{Ab-B7-H3}$ (n=10) compared to $MB_{Non-targeted}$ (n=15); Bottom panel: Representative contrast mode images of a mammary tumor with $MB_{ABY-B7-H3}$ and normal glands with all MB constructs. Scale bar represents 1 mm.

DETAILED DESCRIPTION

Figure 5:
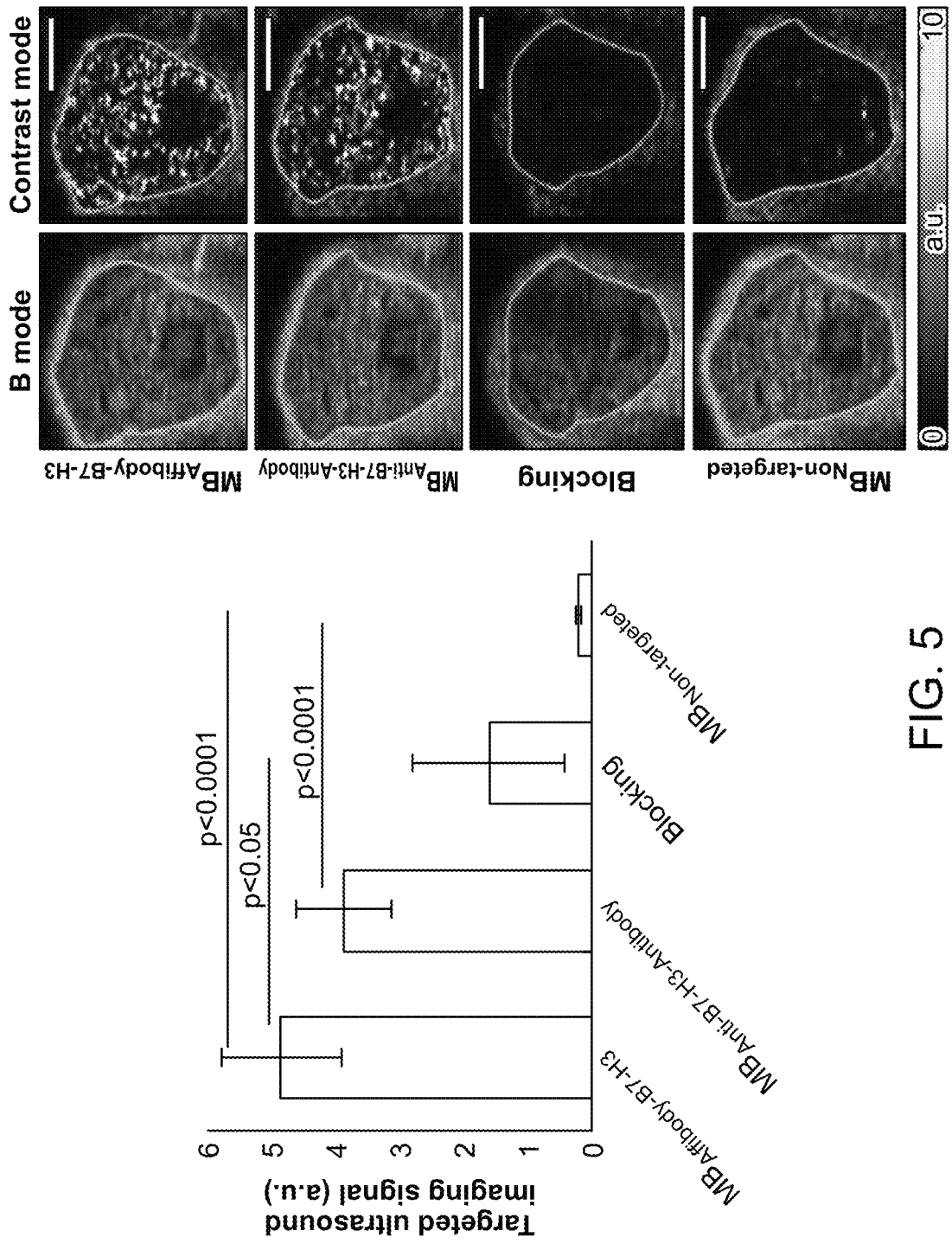
FIG. 5. In vivo ultrasound imaging in a transgenic breast cancer mouse model using microbubbles conjugates to affibody B7-H3, FIG. 6. Affibody B7-H3 conjugated microbubbles do not bind to normal breast tissue.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention, Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

By "comprising" it is meant that the recited elements are required in the composition/method/kit, but other elements may be included to form the composition/method/kit etc. within the scope of the claim. For example, a composition comprising a Wnt agonist or antagonist described herein is a composition that may comprise other elements in addition to Wnt agonist or antagonist described herein, e.g. functional moieties such as polypeptides, small molecules, or nucleic acids bound, e.g. covalently bound, to the Wnt agonist or antagonist described herein; agents that promote the stability, agents that promote solubility, adjuvants, etc. as will be readily understood in the art, with the exception of elements that are encompassed by any negative provisos.

By "consisting essentially of", it is meant a limitation of the scope of composition or method described to the specified materials or steps that do not materially affect the basic and novel characteristic(s) of the subject invention. For example, a Wnt agonist or antagonist "consisting essentially of" a disclosed sequence has the amino acid sequence of the disclosed sequence plus or minus about 5 amino acid residues at the boundaries of the sequence based upon the sequence from which it was derived, e.g. about 5 residues, 4 residues, 3 residues, 2 residues or about 1 residue less than the recited bounding amino acid residue, or about 1 residue, 2 residues, 3 residues, 4 residues, or 5 residues more than the recited bounding amino acid residue, By "consisting of", it is meant the exclusion from the composition, method, or kit of any element, step, or ingredient not specified in the claim. For example, a Wnt agonist or antagonist "consisting of" a disclosed sequence consists only of the disclosed amino acid sequence.

General methods in molecular and cellular biochemistry can be found in such standard textbooks as Molecular Cloning: A Laboratory Manual, 3rd Ed. (Sambrook et al., CSH Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

B7-H3 (CD276) is a 316-amino acid (aa) type I transmembrane glycoprotein belonging to the immunoglobulin superfamily that contains a putative 28 aa signal peptide, a 217 aa extracellular region with one V-like and one C-like Ig domain, a transmembrane region and a 45 aa cytoplasmic domain. Its molecular weight is ~45-66 kDa. As a result of axon duplication, the extracellular architecture of B7-H3 is characterized by a single IgV-IgC-like (2IgB7-H3) or IgV-IgC-IgV-IgC-like domain containing conserved cysteine residues. The predominant isoform in human tissues and cell lines is 4IgB7-H3 rather than 2IgB7-H3. The B7-H3 gene is located on chromosome 15 in humans and on chromosome 9 in mice. This gene consists of ten axons, among which exons 4 to 7 encode the extracellular IgV-IgC domains, B7-H3 is one of the most evolutionarily conserved B7 family members.

The term "polypeptide" as used herein includes oligopeptides and refers to a single chain of amino acids connected by one or more peptide bonds. The polypeptide may comprise one or more helical domains of an affibody of any of SEQ ID NO:1, 2, 3, and/or 4 or variants thereof as described herein.

Affibodies are designed protein molecules developed on a scaffold, for example the three-helix bundle derived from the Z domain of staphylococcal protein A. By randomizing amino acids on two of the three helices, large libraries can be constructed, from which potent binders can be isolated by a variety of display method. Affibody molecules can be selected to a large variety of different proteins, and can be functionalized with genetic fusions to protein modules or by chemical conjugation to functional moieties, such as toxins, imaging agents, epitope tags, and the like.

Affibody proteins have very small size and hence favorable properties for diagnostic imaging because a molecular size below 10 kDa allows more rapid extravasation from blood vessels and penetration into tissue, allowing for rapid reach of tumor targets, and a short plasma half-life. Imaging is an important tool to identify, characterize and monitor tumors. Affibodies for imaging purposes may be conjugated, for example to chelating agents for complexation of radio-metals, and imaged by single photon computed tomography (SPECT), positron emission tomography (PET), fluorescent probes in the ultraviolet, near infrared, etc.

Affibody molecules have the ability to bind protein targets with high affinity and selectivity. In contrast to antibodies that have Fc, however, they lack half-life extension and effector function modules. Therapeutic action can thus either be directly carried out by blocking ligand receptor interactions, or by functionalizing the Affibody molecules to have long half-lives and toxic payloads. For example a small engineered albumin-binding domain (ABD) has been genetically fused to affibodies, and they have been conjugated to therapeutic radionuclides, or protein toxins such as Pseudomonas exotoxin. Affibodies have also been engineered in different formats for tailored kinetic properties, including PEGylation, Fc-fusion or fusion to ABD for albumin binding.

Affibody molecules have been combinatorially fused with antibodies to form functional multispecific proteins called 'AffiMabs', for example which have a symmetric bi-valency and Fc sequence of common IgGs, with corresponding substantial half-life and stability in vivo and facile manufacturability.

Colloidal bubbles (microbubbles) are important contrast agents for diagnostic, theranostic, or therapeutic purposes, in that they can provide simultaneous and co-localized contrast for imaging and drug carrying and delivering capacity for targeted therapy. The imaging modality and therapeutic trigger is ultrasound, which is focused to microscale events distributed throughout the insonified vasculature. A gas core, e.g., air, perfluorocarbon, etc, provides the mechanism for ultrasound backscatter. Gas bubbles of this size in aqueous media are unstable owing to surface tension effects, and require a stabilizing shell. The shell may be composed of surfactants, lipids, proteins, polymers, or a combination of these materials.

Lipid-coated microbubble formulations are commercially available and approved for clinical use, e.g. Definity (Lantheus Medical Imaging) and Sonovue® (Bracco Diagnostics), Phospholipids spontaneously self-assemble into a highly oriented monolayer at the air-water interface, forming around a newly entrained gas bubble. Lipid-coated microbubbles have exhibited favorable ultrasound characteristics, such as resonance with minimal damping and the ability to reseal around the gas core following fragmentation, and are easily functionalized for drug delivery, molecular imaging or other purposes by incorporating different lipid headgroup species or post-production bio-conjugation. Examples include phosphatidyl choline and lipopolymers.

Protein-shelled microbubbles include albumin shells, avidin, mixed avidin and albumin, etc. Other shells include surfactants, e.g. SPAN-40, TWEEN-40, sucrose stearate, etc. The term "polymer microbubble" typically refers to a special class of microbubbles that are stabilized by a thick shell comprising cross-linked or entangled polymeric species. The bulk nature of the polymer shell makes it more resistant to area compression and expansion than its lipid and albumin counterparts, which reduces the echogenicity and drug delivery activity.

Microbubbles have useful effects when they are insonified by ultrasound. At low acoustic pressures, an insonified microbubble produces a backscattered echo that can be used to detect and locate the microbubble. The microbubble can therefore be used as a contrast agent in ultrasound imaging. The echogenicity, or relative strength of the backscattered signal, is strongest near the microbubble resonance frequency. Bubbles of a few micrometers in diameter resonate at frequencies in the 1-10 MHz range which is the range of typical ultrasound clinical imaging scanners. Thus, microbubbles are highly echogenic to conventional ultrasound. Additionally, microbubbles scatter ultrasound nonlinearly. Imaging pulse sequences with modulated phase, frequency and amplitude can be used to separate the microbubble and tissue signals with high fidelity.

At higher acoustic pressures, the microbubble may become unstable during oscillation and fragment into daughter bubbles. Fragmentation is a useful means of eliminating the contrast agent signal within the transducer focus.

Microbubble fragmentation is being employed to measure reperfusion in tumor and cardiac tissue and in ultrasound molecular imaging protocols.

At acoustic pressures just below the fragmentation threshold, a microbubble will undergo dissolution, e.g. for drug delivery. At high acoustic pressures and lower frequencies inertial cavitation occurs and can be exploited for drug delivery.

Commercialization of advanced ultrasound scanner technology and contrast agent detection methods (e.g., Siemens' Cadence Pulse Sequencing® mode) has made microbubble contrast agents highly effective in imaging.

A "patient" for the purposes of the present invention includes both humans and other animals, particularly mammals, including pet and laboratory animals, e.g. mice, rats, rabbits, etc. Thus the methods are applicable to both human therapy and veterinary applications. In one embodiment the patient is a mammal, preferably a primate. In other embodiments the patient is human.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having cancer. Subjects may be human, but also include other mammals, particularly those mammals useful as laboratory models for human disease, e.g. mouse, rat, etc.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. Cells of interest for detection, analysis, or treatment in the present application include precancerous (e.g., benign), malignant, pre-metastatic, metastatic, and non-metastatic cells. Cancers of virtually every tissue are known. The phrase "cancer burden" refers to the quantum of cancer cells or cancer volume in a subject. Reducing cancer burden accordingly refers to reducing the number of cancer cells or the cancer volume in a subject. The term "cancer cell" as used herein refers to any cell that is a cancer cell or is derived from a cancer cell e.g. clone of a cancer cell. Many types of cancers are known to those of skill in the art, including solid tumors such as carcinomas, sarcomas, glioblastomas, melanomas, lymphomas, myelomas, etc., and circulating cancers such as leukemias. Examples of cancer include but are not limited to, ovarian cancer, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor. Metastasis can also be defined as several steps of a process, such as the departure of cancer cells from an original tumor site, and migration and/or invasion of cancer cells to other parts of the body.

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample comprising cancer cells from a patient. A biological sample comprising a cancer cell from a patient can also include non-cancerous cells.

The term "diagnosis" is used herein to refer to the identification of a molecular or pathological state, disease or condition, such as the identification of a molecular subtype of breast cancer, prostate cancer, or other type of cancer.

The term "prognosis" is used herein to refer to the prediction of the likelihood of cancer-attributable death or progression, including recurrence, metastatic spread, and drug resistance, of a neoplastic disease, such as ovarian cancer. The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence.

As used herein, the terms "treatment," "treating," and the like, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of a tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease;

(b) inhibiting the disease, i.e., arresting its development; and
(c) relieving the disease, i.e., causing regression of the disease.

Treating may refer to any indicia of success in the treatment or amelioration or prevention of an cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with cancer or other diseases. The term "therapeutic effect" refers to the reduction, elimination, or prevention of the disease, symptoms of the disease, or side effects of the disease in the subject.

As used herein, endpoints for treatment will be given a meaning as known in the art and as used by the Food and Drug Administration.

Overall survival is defined as the time from randomization until death from any cause, and is measured in the intent-to-treat population. Survival is considered the most reliable cancer endpoint, and when studies can be conducted to adequately assess survival, it is usually the preferred endpoint. This endpoint is precise and easy to measure, documented by the date of death. Bias is not a factor in endpoint measurement. Survival improvement should be analyzed as a risk-benefit analysis to assess clinical benefit. Overall survival can be evaluated in randomized controlled studies. Demonstration of a statistically significant improvement in overall survival can be considered to be clinically significant if the toxicity profile is acceptable, and has often supported new drug approval. A benefit of the methods of the invention can include increased overall survival of patients.

Endpoints that are based on tumor assessments include DFS, ORR, TTP, PFS, and time-to-treatment failure (TTF). The collection and analysis of data on these time-dependent endpoints are based on indirect assessments, calculations, and estimates (e.g., tumor measurements). Disease-Free Survival (DFS) is defined as the time from randomization until recurrence of tumor or death from any cause. The most frequent use of this endpoint is in the adjuvant setting after definitive surgery or radiotherapy. DES also can be an important endpoint when a large percentage of patients achieve complete responses with chemotherapy.

Objective Response Rate. ORR is defined as the proportion of patients with tumor size reduction of a predefined amount and for a minimum time period. Response duration usually is measured from the time of initial response until documented tumor progression. Generally, the FDA has defined ORR as the sum of partial responses plus complete responses. When defined in this manner, ORR is a direct measure of drug antitumor activity, which can be evaluated in a single-arm study.

Time to Progression and Progression-Free Survival. TTP and PFS have served as primary endpoints for drug approval. TTP is defined as the time from randomization until objective tumor progression; TTP does not include deaths. PFS is defined as the time from randomization until objective tumor progression or death. The precise definition of tumor progression is important and should be carefully detailed in the protocol.

"In combination with", "combination therapy" and "combination products" refer, in certain embodiments, to the concurrent administration to a patient of the agents described herein. When administered in combination, each component can be administered at the same time or sequentially in any order at different points in time. Thus, each component can be administered separately but sufficiently closely in time so as to provide the desired therapeutic effect.

"Concomitant administration" of active agents in the methods of the invention means administration with the reagents at such time that the agents will have a therapeutic effect at the same time. Such concomitant administration may involve concurrent (Le. at the same time), prior, or subsequent administration of the agents. A person of ordinary skill in the art would have no difficulty determining the appropriate timing, sequence and dosages of administration for particular drugs and compositions of the present invention.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s), "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease. An effective amount or effective dose with respect to an imaging agent is that does that provides for imaging of a cancerous lesion in an individual, if such a lesion is present.

Polypeptide Compositions

In an embodiment, polypeptide compositions are provided comprising affibody sequences with a high affinity binding to human B7-H3, as set forth in any of SEQ ID NO:1, 2, 3, and/or 4, or variants and derivatives, including conjugates and fusion proteins, thereof. The polypeptides and proteins of the invention are useful as anti-human B7-H3 binding moieties, and may additionally cross-react with non-human B7-H3 proteins, including without limitation mouse B7-H3. In this regard, an embodiment of the invention provides an anti-B7-H3 binding moiety comprising any of the polypeptides or proteins described herein. Methods of testing for the ability to bind to B7-H3 are known in the art and include any antigen binding assay, such as, for example, radioimmunoassay (RIA), enzyme-linked immunosorbent assay (ELISA), Western blot, immunoprecipitation, surface plasmin resonance, and competitive inhibition assays.

Exemplary sequences are:

```
(SEQ ID NO: 1) AC2:
AEAKYAKEKIFAVGEIYWLPNLTHGQIMAFIAALNDDPSQSSELLSEAK
KLNDSQAPK (SEQ ID NO: 2) AC9:
AEAKYAKEKIIALSEIIWLPNLTHGQIMAFIAALNDDPSQSSELLSEAK
KLNDSQAPK (SEQ ID NO: 3) AC12:
AEAKYAKEKIAALSEIIWLPNLTHGQIMAFIAALNDDPSQSSELLSEAK
KLNDSQAPK (SEQ ID NO: 4) AC16:
AEAKYAKEKVHALSEIIWLPNLTHGQIMAFIAALNDDPSQSSELLSEAK
KLNDSQAPK
```

In some embodiments, the affinity of an affibody for B7-H3 is characterized by a $K_d$ (dissociation constant) of $10^{-6}$ M or less; $10^{-7}$ or less, $10^{-9}$ or less, $10^{-9}$ or less, which may be determined by methods known in the art, including those described in the Examples. "Affinity" refers to the strength of binding, increased binding affinity being correlated with a lower $K_d$.

The polypeptide may further comprise a leader sequence, signal peptide, linker, fusion partner, etc. The polypeptide may be conjugated to an epitope tag, e.g. for purification. In an embodiment of the invention, while the leader sequence may facilitate expression of the polypeptide on the surface of the cell, the presence of the leader sequence in an expressed polypeptide is not necessary in order for the polypeptide to function. In an embodiment of the invention, upon expression of the polypeptide on the cell surface, the leader sequence may be cleaved off of the polypeptide. Accordingly, in an embodiment of the invention, the polypeptide lacks a leader sequence.

If, for example, the protein comprises a single polypeptide chain comprising one of (i) SEQ ID NO: 1-4, the polypeptide may further comprise other amino acid sequences, e.g., an amino acid sequence encoding an immunoglobulin Fc sequence, albumin binding protein, etc. or a portion thereof. A fusion protein can comprise one or more copies of the affibody and/or one or more copies of the other polypeptide. For instance, the fusion protein can comprise 1, 2, 3, 4, 5, or more, copies of the affibody and/or of the other polypeptide. Suitable methods of making fusion proteins are known in the art, and include, for example, recombinant methods. See, for instance, Choi et al,, Mol, Biotechnol. 31: 193-202 (2005), Included in the scope of the invention are functional portions of the inventive polypeptides, proteins, and chimeric antigen receptors (CARS) and derivatives thereof. The term "functional portion" refers to any part or fragment of the polypeptide that retains the biological activity of the polypeptide. Functional portions encompass, for example, those sequences that retain the ability to recognize target cells, or detect, treat, or prevent a disease, to a similar extent, the same extent, or to a higher extent, as the parent polypeptide, protein, or CAR. In reference to the parent polypeptide the functional portion can comprise, for instance, about 10%, 25%, 30%, 50%, 68%, 80%, 90%, 95%, or more, of the parent polypeptide.

For example, an affibody sequence may be truncated at the C-terminus or the N-terminus by 1, 2, 3, 4, 5, etc. amino acid residues, so long as the binding affinity is retained. Alternatively the functional portion can comprise additional amino acids at the amino or carboxy terminus of the portion, or at both termini, which additional amino acids are not found in the amino acid sequence of the parent polypeptide. Desirably, the additional amino acids do not interfere with the biological function of the functional portion, e.g., recognize target cells, detect cancer and/or tumor vasculature, treat or prevent cancer, reduce or eliminate tumor vasculature, etc. More desirably, the additional amino acids enhance the biological activity, as compared to the biological activity of the parent.

Included are functional variants of the anti-B7-H3 polypeptides described herein. The term "functional variant" as used herein refers to a polypeptide having substantial or significant sequence identity or similarity to a parent polypeptide, which functional variant retains the biological activity of the polypeptide of which it is a variant. Functional variants encompass, for example, those variants of the polypeptide described herein that retain the ability to recognize target cells to a similar extent, the same extent, or to a higher extent, as the parent polypeptide. In reference to the parent polypeptide, the functional variant can, for instance, be at least about 30%, about 50%, about 75%, about 80%, about 85%, about 90%, about 91%, about 92%, about 93%, about 94%, about 95%, about 96%, about 97%, about 98%, about 99% or more identical in amino acid sequence to the parent polypeptide.

In some embodiments a sequence variant comprises a sequence of any of SEQ ID NO:1-4, residues 1-36 fused in frame or through a linker to a third helix sequence, which third helix sequence may be variable provided that protein stability is maintained, for example where from 1 to 10, from 1 to 5, from 1-4, from 1-3, from 1-2 or 1 amino acid residue is substituted relative to the sequence provided in any of SEQ ID NO:1-4, residues 37-58. Examples of suitable third helix sequences include sequences known in the art, for example shown as SEQ ID NO:5-20, below.

| | |
|---|---|
| SEQ ID NO: 5 | DPSQSAELLAEAKKLNDAQAPK |
| SEQ ID NO: 6 | DPSQSANLLAEAKKLNDAQAPK |
| SEQ ID NO: 7 | DPSQSANLLSEAKKLNESQAPK |
| SEQ ID NO: 8 | DPSQSANVLGEAKKLNDSQAPK |
| SEQ ID NO: 9 | DPSQSANVLGEAQKLNDSQAPK |
| SEQ ID NO: 10 | DPSQSSNLLSEAKKLNESQAPK |
| SEQ ID NO: 11 | DPSQSTNVLGEAKKLNESQAPK |
| SEQ ID NO: 12 | DPSVSKEILAEAKKLNDAQAPK |
| SEQ ID NO: 13 | DPSVSKEILAEAKKLNESQAPK |
| SEQ ID NO: 14 | DPSQSANLLAEAKKLNDAQAPK |
| SEQ ID NO: 15 | DPSQSANLLSEAKKLNESQAPK |
| SEQ ID NO: 16 | DPSQSANVLGEAQKLNDSQAPK |
| SEQ ID NO: 17 | DPSQSTNVLGEAKKLNESQAPK |
| SEQ ID NO: 18 | DPSVSKEILAEAKKLNDAQAPK |
| SEQ ID NO: 19 | DPSVSKEILAEAKKLNESQAPK |
| SEQ ID NO: 20 | DSSQSANVLGEAQKLNDSQAPK |
| SEQ ID NO: 21 | DPSQSSELLSEAKKLNDSQAPK |

In some embodiments residues 1-36 of the affibody have a sequence of formula I

A E A K Y A K E K $X_1$ $X_2$ A $X_3$ $X_4$ S E I $X_5$ W L P N L T H G Q I M A F I A A L N D where $X_1$ is selected from I, V, L, A, F usually I or V;
$X_2$ is selected from I, V, L, A, F, H usually F, I, A, H;
$X_3$ is selected from I, V, L, A, F usually L, V;
$X_4$ is selected from G or S;
$X_5$ is selected from Y or I;
which sequence may be joined to a third helix sequence.

A functional variant can, for example, comprise the amino acid sequence of the parent polypeptide with one, two, three or more conservative amino acid substitution(s). Alternatively or additionally, the functional variants can comprise the amino acid sequence of the parent polypeptide with one, two, three or more non-conservative amino acid substitution(s). It is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent polypeptide.

Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g, Ile, Thr, and Val), an amino acid with an aromatic side-chain substituted for another amino acid with an aromatic side chain (e.g., His, Phe, Trp, and Tyr), etc.

The polypeptide sequences (including functional portions and functional variants) can be of any length, i.e., can comprise any number of amino acids, provided that the polypeptides, (or functional portions or functional variants thereof) retain their biological activity, e.g., the ability to specifically bind to antigen, detect diseased cells in a mammal, or treat or prevent disease in a mammal, etc.

The polypeptide sequences (including functional portions and functional variants) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, 6-hydroxylysine, ornithine, aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The polypeptide sequences (including functional portions and functional variants) can be glycosylated, amidated, carboxylated, phosphorylated, esterified, N-acylated, cyclized via, e.g, a disulfide bridge, or converted into an acid addition salt and/or optionally dimerized or polymerized.

The polypeptide sequences (including functional portions and functional variants) can be obtained by methods known in the art. The polypeptides, proteins, or CARs may be made by any suitable method of making polypeptides or proteins. Suitable methods of de novo synthesizing polypeptides and proteins are described in references, such as Chan et al., Fmoc Solid Phase Peptide Synthesis, Oxford University Press, Oxford, United Kingdom, 2000; Peptide and Protein Drug Analysis, ed. Reid, R., Marcel Dekker, Inc., 2000: Epitope Mapping, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. Further, polypeptide sequences (including functional portions and functional variants) can be isolated and/or purified from a source, such as a plant, a bacterium, an insect, a mammal, e.g., a rat, a human, etc.

Polypeptide Conjugates

The affibodies polypeptides disclosed herein have utility on their own without conjugation and may be utilized without further modification. However, the conjugation of effector function, cytotoxic or imaging agents is yet another embodiment, as the added moieties also add functionality to the polypeptide.

Thus, the anti-B7-H3 affibodies may be coupled or conjugated to one or more therapeutic cytotoxic or imaging moieties. As used herein, "cytotoxic moiety" simply means a moiety that inhibits cell growth or promotes cell death when proximate to or absorbed by the cell. Suitable cytotoxic moieties in this regard include radioactive isotopes (radionuclides), chemotoxic agents such as differentiation inducers and small chemotoxic drugs, toxin proteins, and derivatives thereof. As utilized herein, "imaging moiety" means a moiety which can be utilized to increase contrast between a tumor and the surrounding healthy tissue in a visualization technique (e.g., radiography, positron-emission tomography, magnetic resonance imaging, direct or indirect visual inspection.) Thus, suitable imaging moieties include microbubbles, radiography moieties (e.g, heavy metals and radiation emitting moieties), positron emitting moieties, magnetic resonance contrast moieties, and optically visible moieties (e.g., fluorescent or visible-spectrum dyes, visible particles, etc.). It will be appreciated by one of ordinary skill that some overlap exists between what is a therapeutic moiety and what is an imaging moiety. For instance $^{212}$Pb and $^{212}$Bi are both useful radioisotopes for therapeutic compositions, but are also electron-dense, and thus provide contrast for X-ray radiographic imaging techniques, and can also be utilized in scintillation imaging techniques. Microbubbles are useful for delivery of drugs, in addition to their imaging properties.

In general, therapeutic or imaging agents may be conjugated to the anti-B7-H3 affibody by any suitable technique, with appropriate consideration of the need for pharmokinetic stability and reduced overall toxicity to the patient. A therapeutic agent may be coupled either directly or indirectly (e.g. via a linker group). A direct reaction between an agent and an affibody is possible when each possesses a functional group capable of reacting with the other. For example, a nucleophilic group, such as an amino or sulfhydryl group, may be capable of reacting with a carbonyl-containing group, such as an anhydride or an acid halide, or with an alkyl group containing a good leaving group (e.g., a halide). Alternatively, a suitable chemical linker group may be used. A linker group can function as a spacer to distance an affibody from an agent in order to avoid interference with binding capabilities. A linker group can also serve to increase the chemical reactivity of a substituent on a moiety or an affibody, and thus increase the coupling efficiency. An increase in chemical reactivity may also facilitate the use of moieties, or functional groups on moieties, which otherwise would not be possible.

Suitable linkage chemistries include maleimidyl linkers and alkyl halide linkers (which react with a sulfhydryl on the affibody moiety) and succinimidyl linkers (which react with a primary amine on the affibody moiety). Several primary amine and sulfhydryl groups are present on affibodies, and additional groups may be designed into recombinant molecules. It will be evident to those skilled in the art that a variety of bifunctional or polyfunctional reagents, both homo- and hetero-functional (such as those described in the catalog of the Pierce Chemical Co., Rockford, Ill.), may be employed as a linker group. Coupling may be effected, for example, through amino groups, carboxyl groups, sulfhydryl groups or oxidized carbohydrate residues. There are numerous references describing such methodology, e.g., U.S. Pat. No. 4,671,958. As an alternative coupling method, cytotoxic or imaging moieties may be coupled to the anti-B7-H3 affibody moiety through a an oxidized carbohydrate group at a glycosylation site, as described in U.S. Pat. Nos. 5,057,313 and 5,156,840. Yet another alternative method of coupling the affibody moiety to the cytotoxic or imaging moiety is by the use of a non-covalent binding pair, such as streptavidin/biotin, or avidin/biotin. In these embodiments, one member of the pair is covalently coupled to the affibody moiety and the other member of the binding pair is covalently coupled to the cytotoxic or imaging moiety.

Imaging Conjugates

Imaging conjugates may comprise any of a variety of agents, e.g. contrast agents such as microbubbles, fluorophores, radio-agents, and the like as known in the art.

In some embodiments a contrast agent is a microbubble. As used herein, "microbubbles" refer to micron-sized contrast agents composed of a shell and a gas core, as is well known to those of skill in the art. Microbubbles are commercially available from a number of sources. The shell may be formed from any suitable material, including but not limited to albumin, polysaccharides (such as galactose), lipids (such as phospholipids), polymers and combinations thereof. Any suitable gas core can be used in the microbubbles of the invention, including but not limited to air, octafluoropropane, perfluorocarbon, sulfur hexafluoride or nitrogen. The gas core determines the echogenecity of the microbubble. When gas bubbles are caught in an ultrasound frequency field, they compress, oscillate, and reflect a characteristic echo, this generates the strong and unique sonogram in contrast-enhanced ultrasound. Gas cores can be composed of air, or heavy gases like octafluoropropane, perfluorocarbon, sulfur hexafluoride or nitrogen. Heavy gases are less water-soluble so they are less likely to leak out from the microbubble to impair echogenecity.

The average diameter of the microbubble can be between 1 μm and 25 μm. In general, the microbubbles have a diameter of about 1 μm and about 10 μm on average, and more preferably between about 1 μm and 5 μm, 1 μm and 4 μm, 1 μm and 3 μm, 1 μm and about 2 pm, 2 μm and 5 μm, 2 μm and 4 μm, 2 μm and 3 μm, 3 μm and 5 μm, 3 μm and 4 μm, or about as 1 μm, 2 μm, 2.5 μm, 3 μm, 3.5 μm or 4 μm on average. OPTISON®, (made by GE Healthcare) was the first microbubble approved by Food and Drug Administration (FDA), and has an albumin shell and octafluoropropane ($C_3F_8$) gas core. The second FDA-approved microbubble, LEVOVIST®, (made by Schering AG), has a palmitic acid/galactose shell and an air core. Other examples of microbubble include, but are not limited to ALBUNEX® (made by Molecular Biosystems), SONOVUE® (made by Bracco Diagnostics, Inc.), SONOZOID® (made by Schering AG), SONOVIST® (made by Schering AG), and DEFINITY® (made by DuPont Pharmaceuticals). ALBUNEX® has an albumin shell and an air core. SONOVUE® and contains a sulfur hexafluoride ($SF_6$) gas core that is stabilized in aqueous dispersion of a monolayer of phospholipids. SONOZOID® is another microbubble preparation containing a perfluorocarbon gas core and a lipid shell. DEFINITY® is another FDA-approved microbubble that contains a lipid shell and an octafluoropropane ($C_3F_8$) gas core. In one exemplary embodiment, microbubbles of the present invention comprise a lipid shell and perfluorocarbon gas core of between about 1 µm and about 5 µm, 1 µm and about 4 µm diameter, 1 µm and about 3 µm, or 1 µm and about 2 µm, on average.

The microbubbles can be used, for example, as a contrast agent for ultrasound imaging. Microbubbles have a high degree of echogenicity (i.e.: the ability of an object to reflect ultrasound waves). The echogenicity difference between the gas in the microbubbles and the soft tissue surroundings of the body is large. Thus, ultrasonic imaging using microbubble contrast agents enhances the ultrasound backscatter, or reflection of the ultrasound waves, to produce a unique sonogram with increased contrast due to the high echogenicity difference.

The microbubbles can be functionalized in any suitable manner for binding to the affibody polypeptide. Such techniques are well known to those of skill in the art, such as those for functionalizing the surface of a microbubble to permit binding of a protein. In one embodiment, the microbubble surface is functionalized to permit direct attachment of the binding agent to the microbubble surface. In another embodiment, the microbubble surface is functionalized to permit indirect attachment of the binding molecule to the microbubble surface. In one non-limiting embodiment of indirect binding, the microbubble surface can be coated with streptavidin, to which biotinylated binding molecules can be bound. Any other suitable binding pair can be similarly used, as will be apparent to those of skill in the art.

Following administration to the patient (such as by parenteral, e.g. intravenous injection), the targeted microbubbles accumulate at tissue sites that over-express B7-H3, causing a local increase in the ultrasound imaging signal. Due to their small size, the microbubbles stay predominantly within the vascular compartment after intravenous injection. Thus, the microbubbles can be used, for example, to exclusively detect vascular endothelial cell associated molecular markers that are present in early stage cancers or precancerous lesions.

Radiographic moieties for use as imaging moieties in the present invention include compounds and chelates with relatively large atoms, such as gold, iridium, technetium, barium, thallium, iodine, and their isotopes. It is preferred that less toxic radiographic imaging moieties, such as iodine or iodine isotopes, be utilized in the compositions and methods of the invention. Examples of such compositions which may be utilized for x-ray radiography are described in U.S. Pat. No. 5,709,846, incorporated fully herein by reference. Such moieties may be conjugated to the anti-B7-H3 affibody moiety through an acceptable chemical linker or chelation carrier. Positron emitting moieties for use in the present invention include $^{18}F$, which can be easily conjugated by a fluorination reaction with the anti-B7-H3 affibody moiety according to the method described in U.S. Pat. No. 6,187,284; or moieties such as $^{64}Cu$ and $^{68}Ga$ by chelation. The affibody may be conjugated to a chelating agent, e.g. 1,4,7,10-tetraazacyclododecane-N,N',N'',N'''-tetraacetic acid (ROTA), for chelating a radioisotope.

Preferred magnetic resonance contrast moieties include chelates of chromium(III), manganese(II), iron(II), nickel (II), copper(II), praseodymium(III), neodymium(III), samarium(III) and ytterbium(III) ion. Because of their very strong magnetic moment, the gadolinium(III), terbium(III), dysprosium(III), holmium(III), erbium(III), and iron(III) ions are especially preferred. Examples of such chelates, suitable for magnetic resonance spin imaging, are described in U.S. Pat. No. 5,733,522, incorporated fully herein by reference. Nuclear spin contrast chelates may be conjugated to the anti-B7-H3 affibody moieties through a suitable chemical linker.

Optically visible moieties for use as imaging moieties include fluorescent dyes, or visible-spectrum dyes, visible particles, and other visible labeling moieties. Fluorescent dyes such as fluorescein, coumarin, rhodamine, bodipy Texas red, and cyanine dyes such as indocyanine green, are useful when sufficient excitation energy can be provided to the site to be inspected visually. Endoscopic visualization procedures may be more compatible with the use of such labels. For many procedures where imaging agents are useful, such as during an operation to resect a brain tumor, visible spectrum dyes are preferred. Acceptable dyes include FDA-approved food dyes and colors, which are non-toxic, although pharmaceutically acceptable dyes which have been approved for internal administration are preferred. Alternatively, visible particles, such as colloidal gold particles or latex particles, may be coupled to the anti-B7-H3 affibody moiety via a suitable chemical linker.

In some embodiments, methods are utilized for imaging use in vivo, e.g., to locate or identify sites where tumor cells are present. The phrase "in vivo imaging" as used herein refers to methods of detecting the presence of an affibody in whole, live mammal. In these embodiments, a detectably-labeled moiety, e.g., an affibody, which is specific for B7-H3 is administered to an individual (e.g., by injection), and labeled cells are located using standard imaging techniques, including, but not limited to, Positron emission tomography (PET), Magnetic resonance imaging (MRI), Computed tomography (CT), Optical Imaging (OI), Photoacoustic Imaging (PI), and Ultrasound Imaging (US), and the like. The affibody may be labeled with a radionuclide or a microbubble for this purpose. Optically detectable proteins such as fluorescent and luciferases-conjugated proteins may also be detected by in vivo imaging. In vivo imaging of fluorescent proteins in live animals is described in, e.g., Hoffman, Cell Death and Differentiation 2002, 9:786-789.

In general, any conventional method for visualizing diagnostic imaging can be utilized in accordance with this invention, using clinical imaging instruments. For diagnostic in vivo imaging, the type of detection instrument available is a factor in selecting a given radionuclide. A radionuclide chosen must have a type of decay that is detectable by a given type of instrument. Another important factor in selecting a radionuclide for in vivo diagnosis is that its half-life be long enough that it is still detectable at the time of maximum uptake by the target tissue, but short enough that deleterious radiation of the host is minimized.

The detectably labeled B7-H3 specific affibody is used in conjunction with imaging techniques, in order to analyze the expression of the target. In one embodiment, the imaging method is one of PET or SPECT, which are imaging techniques in which a radionuclide is synthetically or locally administered to a patient. The subsequent uptake of the radiotracer is measured over time and used to obtain information about the targeted tissue. Because of the high-energy (γ-ray) emissions of the specific isotopes employed and the sensitivity and sophistication of the instruments used to detect them, the two-dimensional distribution of radioactivity may be inferred from outside of the body. Among the most commonly used positron-emitting nuclides in PET are included $^{11}C$, $^{13}N$, $^{15}O$, and $^{18}F$. Isotopes that decay by electron capture and/or .gamma. emission are used in SPECT, and include $^{123}$I and $^{99m}$Tc.

Where the methods are in vitro, the biological sample can be any sample in which a cancer cell may be present, including but not limited to, blood samples (including whole blood, serum, etc.), tissues, whole cells (e.g., intact cells), and tissue or cell extracts. Particularly, detection can be assessed on an extracellular surface of a cell. For example, the tissue sample may be fixed (e.g., by formalin treatment) and may be provided embedded in a support (e.g., in paraffin) or frozen unfixed tissue.

Assays can take a wide variety of forms, such as competition, direct reaction, or sandwich type assays. Examples of assays include Western blots; agglutination tests; enzyme-labeled and mediated immunoassays, such as enzyme-linked immunosorbent assays (ELISAs); biotin/avidin type assays; radioimmunoassays; immunoelectrophoresis; immunoprecipitation, and the like. The reactions generally include detectable labels conjugated to the affibody. Labels include those that are fluorescent, chemiluminescent, radioactive, enzymatic and/or dye molecules, or other methods for detecting the formation of a complex between antigen in the The diagnostic imaging assays described herein can be used to determine whether a subject has a cancer, as well as monitor the progress of treatment in a subject. Thus, the diagnostic assays can inform selection of therapy and treatment regimen by a clinician.

The assay reagents, including the affibodies of the present disclosure, can be provided in kits, with suitable instructions and other necessary reagents, for imaging purposes. The kit can also contain, depending on the particular assay used, suitable labels and other packaged reagents and materials (i.e. wash buffers and the like). Standard immunoassays, such as those described above, can be conducted using these kits.

Cytotoxic Conjugates

Where a cytotoxic moiety is more potent when free from the affibody portion of the conjugates of the present invention, it may be desirable to use a linker group which is cleavable during or upon internalization into a cell, or which is gradually cleavable over time in the extracellular environment. A number of different cleavable linker groups have been described. The mechanisms for the intracellular release of a cytotoxic moiety agent from these linker groups include cleavage by reduction of a disulfide bond (e.g., U.S. Pat. No. 4,489,710), by irradiation of a photolabile bond (e.g., U.S, Pat. No. 4,625,014), by hydrolysis of derivatized amino acid side chains (e.g., U.S. Pat. No. 4,638,045), by serum complement-mediated hydrolysis (e.g., U.S. Pat. No. 4,671, 958), and acid-catalyzed hydrolysis (e.g., U.S. Pat. No. 4,569,789).

Toxin proteins for use as cytotoxic moieties include ricin, abrin, diphtheria toxin, cholera toxin, gelonin, Pseudomonas exotoxin, Shigella toxin, pokeweed antiviral protein, and other toxin proteins known in the medicinal biochemistry arts. As these toxin agents may elicit undesirable immune responses in the patient, especially if injected intravascularly, they may be encapsulated in a carrier for coupling to the anti-B7-H3 affibody moiety.

Examples of drugs that may be suitable in the conjugates include, but are not limited to, pyrrolobenzodiazepine (PBD) dimer, tubulin-binders such as, for example, dolastatin 10, monomethyl dolastatin 10, auristain E, monomethyl auristain E (MMAE), auristatin F, monomethyl auristatin F, HTI-286, tubulysin M, maytansinoid AP-3, cryptophycin, Boc-Val-Dil-Dap-OH, tubulysin IM-1, Boc-Val-Dil-Dap-Phe-OMe, tubulysin IM-2, Boc-Nme-Val-Val-Dil-Dap-OH, tubulysin 1M-3, and colchicine DA; DNA-alkylators (duocarmycin analogs) such as, for example, duocarmycin SA, duocarmycin ON, duocarmycin DMG, duocarmycin DMA, duocarmycin MA, duocarmycin TM, duocarmycin MB, duocarmycin GA; tomaymycin DM; SJG-136; illudin S; irofulven; apaziquone; triptolide; staurosporine; camptothecin; methotrexate; and other anti-cancer drugs such as, for example, kinase inhibitors, histone deacetylase (HDAC) inhibitors, proteasome inhibitors, and matrix metalloproteinase (MMP) inhibitors. In an embodiment, the drug is MMAE or PBD dimer.

It may be desirable to couple more than one cytotoxic and/or imaging moiety to an affibody. By poly-derivatizing the anti-B7-H3 affibody, several cytotoxic strategies may be simultaneously implemented, an affibody may be made useful as a contrasting agent for several visualization techniques, or a therapeutic affibody may be labeled for tracking by a visualization technique. In one embodiment, multiple molecules of an imaging or cytotoxic moiety are coupled to one affibody molecule. In another embodiment, more than one type of moiety may be coupled to one affibody. Regardless of the particular embodiment, conjugates with more than one moiety may be prepared in a variety of ways. For example, more than one moiety may be coupled directly to an affibody molecule, or linkers which provide multiple sites for attachment (e.g., dendrimers) can be used. Alternatively, a carrier with the capacity to hold more than one cytotoxic or imaging moiety can be used.

A carrier may bear the agents in a variety of ways, including covalent bonding either directly or via a linker group, and non-covalent associations. Suitable covalent-bond carriers include proteins such as albumins (e.g., U.S. Pat. No. 4,507,234), peptides, and polysaccharides such as aminodextran (e.g., U.S. Pat. No. 4,699,784), each of which have multiple sites, for the attachment of moieties. A carrier may also bear an agent by non-covalent associations, such as non-covalent bonding or by encapsulation, such as within a liposome vesicle (e.g., U.S. Pat. Nos, 4,429,008 and 4,873, 088). Encapsulation carriers are especially useful for imaging moiety conjugation to anti-B7-H3 affibody moieties. In addition, encapsulation carriers are also useful in chemotoxic therapeutic embodiments, as they can allow the therapeutic compositions to gradually release a chemotoxic moiety over time while concentrating it in the vicinity of the tumor cells.

Carriers and linkers specific for radionuclide agents (both for use as cytotoxic moieties or positron-emission imaging moieties) include radiohalogenated small molecules and chelating compounds, such as DOTAP. For example, U.S. Pat, No, 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis. Such chelation carriers are also useful for magnetic spin contrast ions for use in magnetic resonance imaging tumor visualization methods, and for the chelation of heavy metal ions for use in radiographic visualization methods.

Preferred radionuclides for use as cytotoxic moieties are radionuclides which are suitable for pharmacological administration. Such radionuclides include $^{123}$I, $^{125}$I, $^{131}$I, $^{90}$Y, $^{211}$At, $^{67}$Cu, $^{186}$Re, $^{188}$Re, $^{212}$Pb, and $^{212}$Bi. Iodine and astatine isotopes are useful radionuclides for use in the therapeutic compositions of the present invention, as a large body of literature has been accumulated regarding their use, $^{131}$I is particularly preferred, as are other β-radiation emitting nuclides, which have an effective range of several millimeters. $^{123}$I, $^{125}$I, $^{131}$I, or $^{211}$At may be conjugated to affibody moieties for use in the compositions and methods utilizing any of several known conjugation reagents, including Iodogen, N-succinimidyl 3-[$^{211}$At]astatobenzoate, N-succinimidyl 3-[$^{131}$I]iodobenzoate (SIB), and, N-succinimidyl 5-[$^{131}$I]podob-3-pyridinecarboxylate (SIPC). Any iodine isotope may be utilized in the recited iodo-reagents. Other radionuclides may be conjugated to anti-B7-H3 affibody moieties by suitable chelation agents known to those of skill in the nuclear medicine arts.

Conjugates are also useful in therapeutic moieties for pharmacokinetic purposes, which may be referred to as a pharmacokinetic moiety. Affibody molecules have the ability to bind protein targets with high affinity and selectivity. In contrast to antibodies that have Fc, however, they lack half-life extension and effector function modules. Therapeutic action can thus either be directly carried out by blocking ligand receptor interactions, or by functionalizing the Affibody molecules to have long half-lives and toxic payloads. Affibodies can be fused for example to a small engineered albumin-binding domain (ABD) to increase circulatory half-life, with increased dose to the tumor and reduced kidney uptake; or to a human serum albumin sequence. Affibodies can also be fused to, for example, an Fc sequence, which provides for effector functions, i.e. an effector function moiety, and increased circulatory half-life. The choice of Fc may be based on the desired effector function, e.g. a human Fc sequence including IgGI IgG2a, IgG2b, IgG3, IgG4, IgA, IgM, IgD, IgE, etc. The Fc region optionally provides for dimerization. Alternatively other molecules can be used to increase the serum half-life, including without limitation, polyethylene glycol (PEG), and mimetics thereof.

Polynucleotide Compositions

In the present methods, an affibody, may be produced by recombinant methods. The nucleic acid encoding the affibody can be inserted into a replicable vector for expression. Many such vectors are available. The vector components generally include, but are not limited to, one or more of the following: an origin of replication, one or more marker genes, an enhancer element, a promoter, and a transcription termination sequence. Exemplary coding sequences for an affibody are provided herein. Codon usage may be optimized for the desired host cell.

Expression vectors will contain a promoter that is recognized by the host organism and is operably linked to the Wnt agonist or antagonist coding sequence. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature.

Promoters suitable for use with prokaryotic hosts include the β-lactamase and lactose promoter systems, alkaline phosphatase, a tryptophan (trp) promoter system, and hybrid promoters such as the tac promoter. However, other known bacterial promoters are also suitable. Such nucleotide sequences have been published, thereby enabling a skilled worker operably to ligate them to a DNA coding sequence. Promoters for use in bacterial systems also will contain a Shine-Dalgarno (S.D.) sequence operably linked to the coding sequence.

Promoter sequences are known for eukaryotes. Examples of suitable promoting sequences for use with yeast hosts include the promoters for 3-phosphoglyceratekinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Transcription from vectors in mammalian host cells may be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment.

Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, x-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence, but is preferably located at a site 5' from the promoter.

Expression vectors used in eukaryotic host cells (yeast, fungi, insect, plant, animal, human, or nucleated cells from other multicellular organisms) may also contain sequences necessary for the termination of transcription and for stabilizing the mRNA. Such sequences are commonly available from the 5' and, occasionally 3', untranslated regions of eukaryotic or viral DNAs or cDNAs.

Construction of suitable vectors containing one or more of the above-listed components employs standard techniques. Isolated plasmids or DNA fragments can be cleaved, tailored, and re-ligated in the form desired to generate the plasmids required. For analysis to confirm correct sequences in plasmids constructed, the ligation mixtures are used to transform host cells, and successful transformants selected by ampicillin or tetracycline resistance where appropriate. Plasmids from the transformants are prepared, analyzed by restriction endonuclease digestion, and/or sequenced.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis*, *Pseudomonas* such as *P. aeruginosa*, and *Streptomyces*. These examples are illustrative rather than limiting.

In addition to prokaryotes, eukaryotic microbes such as filamentous fungi or yeast are suitable expression hosts. *Saccharomyces cerevisiae*, or common baker's yeast, is the most commonly used among lower eukaryotic host microorganisms. However, a number of other genera, species, and strains are commonly available and useful herein, such as Schizosaccharomyces pombe; *Kluyveromyces* hosts such as *K. lactis*, *K. fragilis*, etc.; *Pichia pastoris*; *Candida*; *Neurospora crassa*; *Schwanniomyces* such as *Schwanniomyces occidentalis*; and filamentous fungi such as *Penicillium*, *Tolypocladium*, and *Aspergillus* hosts such as *A. nidulan*, and *A. niger*.

Examples of useful mammalian host cell lines are mouse L cells (L-M[TK-], ATCC#CRL-2648), monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); Chinese hamster ovary cells/-DHFR (CHO); mouse sertoli cells (TM4); monkey kidney cells (CV1 ATCC CCL 70); African green monkey kidney cells (VERO-76, ATCC CRL-1 587); human cervical carcinoma cells (HELA, ATCC CCL 2); canine kidney cells (MACK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2).

Host cells are transfected with the above-described expression vectors for affibody production, and cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression, and will be apparent to the ordinarily skilled artisan.

Imaging Methods

Provided is a method of locating B7-H3 proteins that are overexpressed in a tissue or organ of a subject. The method comprises the steps of: a) administering a affibody molecule, e.g. conjugated to an imaging moiety, described herein to a subject, b) obtaining a diagnostic image of the tissue or organ, c) determining the location of affibody molecule bound to the tissue or organ, and d) correlating the location of the bound affibody molecule with the location of B7-H3 in the subject. Of particular interest is the localization of cancerous lesions over-expressing B7-H3. The affibody molecule is administered in an amount effective to provide an image. The tissue or organ in the subject to be tested is any tissue or organ that is known or suspected to overexpress B7-H3, e.g, potential sites of cancerous lesions. Such tissues and organs include the entire organ or a tissue sample of a breast, an ovary, a salivary gland, a stomach, a kidney, a colon, a lung, a cervix, a bladder, a head, or a neck, including an esophagus.

Obtaining a diagnostic image of the tissue or organ in typically comprises exposing the tissue or organ in the subject to an energy source, whereupon a diagnostic image of the tissue or organ is obtained. The diagnostic image can be, for example, ultrasound image, positron emission tomography (PET) image, a magnetic resonance image (MRI), a computerized tomography (CT) scan, single photon emission computed spectroscopy (SPECT) image, or the like.

The diagnostic image can be an MRI, When administered to a subject, a radiolabeled affibody molecule distributes in various concentrations to different tissues, and catalyzes the relaxation of protons in the tissues that have been excited by the absorption of radiofrequency energy from a magnetic resonance imager. This acceleration of the rate of relaxation of the excited protons provides for an image of different contrast when the subject is scanned with a magnetic resonance imager. The magnetic resonance imager is used to record images at various times, generally either before and after administration of the $^{18}$F labeled affibody molecule, or after administration only, and the differences in the images created by the presence of the radiolabeled affibody molecule in tissues are used in diagnosis.

Single Positron Emission Computed Tomography (SPECT) is a non-invasive imaging method to localize the position of a target such as a cancer metastasis, based on radioactive substances that emit gamma radiation when decaying.

A CT scan provides anatomical detail, such as size and location of the tumor or mass. Digital geometry processing is used to generate a three-dimensional image of the internals of an object from a large series of two-dimensional X-ray images taken around a single axis of rotation. CT produces a volume of data which can be manipulated, through a process known as windowing, in order to demonstrate various structures based on their ability to block the X-ray beam. Combined techniques such as PET/CT and PET/MRI are suitable for use in the invention.

PET is a non-invasive imaging method to localize the position of a target such as a cancer metastasis. In PET, 511 keV gamma photons produced during positron annihilation decay are detected. A positron-emitting radionuclide, such as $^{18}$F or $^{76}$Br, is introduced, usually by injection, and accumulates in the target tissue or organ. As it decays it emits a positron, which promptly combines with a nearby electron resulting in the simultaneous emission of two identifiable gamma rays in opposite directions. These are detected by a PET camera and give very precise indication of their origin. A PET scan can provide in vivo physiology such as metabolic detail (e.g., cellular activity) of the tumor or mass. The diagnosis is at a molecular level thereby providing detection of a tumor or mass at an early stage. Since PET is a quantitative tool, the present invention provides a method of measuring the quantity of a B7-H3 that is overexpressed in a tissue or organ of a subject.

In conjunction with the above-described methods, also provided a method of quantifying B7-H3 expression in a tissue or organ of a subject before and after administration of an therapeutic agent, e.g. cancer therapy. It is contemplated that this method is useful as a non-invasive means to determine the effectiveness of an anticancer agent in decreasing B7-H3 positive cells from a tumor, which can be indicative of tumor shrinkage and/or reduction. The method comprises the steps of determining a first amount of affibody molecule bound to the tissue or organ; correlating the first amount of the bound affibody molecule with a first quantity of B7-H3 in the subject; administering cancer therapy; determining a second amount of affibody molecule bound to the tissue or organ, and correlating the second amount of the bound affibody molecule with a second quantity of B7-H3 in the subject.

Methods of Treatment

Methods are provided for treating or reducing primary or metastatic cancer in a regimen comprising contacting the targeted cells with a therapeutically effective affibody composition, e.g. a conjugate to a cytotoxic moiety, or to an immune effector moiety. The administering is optionally in combination with a second therapy, e.g. a chemotherapeutic drug, targeted antibody, immune effector agent, radiotherapy, and the like. Alternatively, the affibody can be utilized as an immune checkpoint modulator, in which case will typically not be conjugated to a cytotoxic agent, although it may be beneficial to conjugate the affibody to a moiety for pharmacokinetic purposes, e.g. increased serum stability, decreased kidney clearance, etc.

The cancer can be any cancer that over-expresses B7-H3 for targeting; or where B7-H3-mediated immune responses are involved, including any of rhabdomyosarcoma, bladder cancer (e.g., bladder carcinoma), bone cancer, brain cancer (e.g., medulloblastoma, neuroblastoma, and glioblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, Ewing's sarcoma, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma), lymphoma, malignant mesothelioma, mastocytoma, melanoma, multiple myeloma, nasopharynx cancer, neuroblastoma, non-Hodgkin lymphoma, B-chronic lymphocytic leukemia, hairy cell leukemia, acute lymphocytic leukemia (ALL), acute lymphocytic cancer, acute myeloid leukemia, Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, stomach cancer, testicular cancer, thyroid cancer, and ureter cancer. Frequently the cancer is a solid tumor such as adult carcinoma, neuroblastoma, glioblastoma, Ewing's sarcoma, rhabdomyosarcoma, prostate cancer, ovarian cancer, colorectal cancer, or lung cancer. In an embodiment, the cancer is characterized by the expression or overexpression of B7-H3.

Effective doses for the treatment of cancer vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g. companion animals such as dogs, cats, horses, etc., laboratory mammals such as rabbits, mice, rats, etc., and the like. Treatment dosages can be titrated to optimize safety and efficacy.

In some embodiments, the therapeutic dosage may range from about 0.0001 to 100 mg/kg, and more usually 0.01 to 5 mg/kg, of the host body weight. For example dosages can be from about 0.1 mg/kg body weight, up to 1 mg/kg body weight, up to 10 mg/kg body weight, up to 25 mg/kg body weight, or within the range of 0.1-25 mg/kg. An exemplary treatment regime entails administration once every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

In prophylactic applications, a relatively low dosage may be administered at relatively infrequent intervals over a long period of time. Some patients continue to receive treatment for the rest of their lives. In other therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

In still other embodiments, methods of the present invention include treating, reducing or preventing tumor growth, tumor metastasis or tumor invasion of cancers including carcinomas, hematologic cancers, melanomas, sarcomas, gliomas, etc. For prophylactic applications, pharmaceutical compositions or medicaments are administered to a patient susceptible to, or otherwise at risk of disease in an amount sufficient to eliminate or reduce the risk, lessen the severity, or delay the onset of the disease, including biochemical, histologic and/or behavioral symptoms of the disease, its complications and intermediate pathological phenotypes presenting during development of the disease.

Compositions for the treatment of cancer can be administered by parenteral, topical, intravenous, intratumoral, oral, subcutaneous, intraarterial, intracranial, intraperitoneal, intranasal or intramuscular means. A typical route of administration is intravenous or intratumoral, although other routes can be equally effective.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the combined agents described herein can be determined by standard pharmaceutical procedures in cell cultures or experimental animals, e,g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that compositions of the invention when administered orally, should be protected from digestion. This is typically accomplished either by complexing the molecules with a composition to render them resistant to acidic and enzymatic hydrolysis, or by packaging the molecules in an appropriately resistant carrier,such as a liposome or a protection barrier. Means of protecting agents from digestion are well known in the art.

The compositions for administration will commonly comprise an affibody dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

Also within the scope of the invention are kits comprising the active agents and formulations thereof, of the invention and instructions for use. The kit can further contain a least one additional reagent, e.g. a chemotherapeutic drug, etc. Kits typically include a label indicating the intended use of the contents of the kit. The term label includes any writing, or recorded material supplied on or with the kit, or which otherwise accompanies the kit.

Combination therapy may provide for administration of an affibody in combination with an anti-tumor agent, or a pharmaceutically acceptable salt or prodrug thereof. Further, detection of cancer with an imaging agent as described herein can be used to guide treatment, e.g. by determining the efficacy of a treatment and making clinical decisions as to whether to continue or discontinue a treatment, making an initial diagnosis of cancer and treating according, and the like.

In some embodiments, the anti-tumor agents include but are not limited to antitumor alkylating agents, antitumor antimetabolites, antitumor antibiotics, plant-derived antitumor agents, antitumor organoplatinum compounds, antitumor campthotecin derivatives, antitumor tyrosine kinase inhibitors, monoclonal antibodies, interferons, biological response modifiers, and other agents having antitumor activities, or a pharmaceutically acceptable salt thereof.

Alkylating agents are known to act through the alkylation of macromolecules such as the DNA of cancer cells, and are usually strong electrophiles. This activity can disrupt DNA synthesis and cell division. Examples of alkylating reagents suitable for use herein include nitrogen mustards and their analogues and derivatives including, cyclophosphamide, ifosfamide, chlorambucil, estramustine, mechlorethamine hydrochloride, melphalan, and uracil mustard. Other examples of alkylating agents include alkyl sulfonates (e.g, busulfan), nitrosoureas (e.g. carmustine, lomustine, and streptozocin), triazenes (e.g. dacarbazine and temozolomide), ethyleniminesimethylmelamines (e.g. altretamine and thiotepa), and methylhydrazine derivatives (e.g. procarbazine). Included in the alkylating agent group are the alkylating-like platinum-containing drugs comprising carboplatin, cisplatin, and oxaliplatin, Antimetabolic antineoplastic agents structurally resemble natural metabolites, and are involved in normal metabolic processes of cancer cells such as the synthesis of nucleic acids and proteins. They differ enough from the natural metabolites so that they interfere with the metabolic processes of cancer cells. Suitable antimetabolic antineoplastic agents to be used in the present invention can be classified according to the metabolic process they affect, and can include, but are not limited to, analogues and derivatives of folic acid, pyrimidines, purines, and cytidine. Members of the folic acid group of agents suitable for use herein include, but are not limited to, methotrexate (amethopterin), pemetrexed and their analogues and derivatives. Pyrimidine agents suitable for use herein include, but are not limited to, cytarabine, floxuridine, fluorouracil (5-fluorouracil), capecitabine, gemcitabine, and their analogues and derivatives. Purine agents suitable for use herein include, but are not limited to, mercaptopurine (6-mercaptopurine), pentostatin, thioguanine, cladribine, and their analogues and derivatives. Cytidine agents suitable for use herein include, but are not limited to, cytarabine (cytosine arabinodside), azacitidine (5-azacytidine) and their analogues and derivatives.

Natural antineoplastic agents comprise antimitotic agents, antibiotic antineoplastic agents, camptothecin analogues, and enzymes, Antimitotic agents suitable for use herein include, but are not limited to, vinca alkaloids like vinblastine, vincristine, vindesine, vinorelbine, and their analogues and derivatives. They are derived from the Madagascar periwinkle plant and are usually cell cycle-specific for the M phase, binding to tubulin in the microtubules of cancer cells. Other antimitotic agents suitable for use herein are the podophyllotoxins, which include, but are not limited to etoposide, teniposide, and their analogues and derivatives. These reagents predominantly target the G2 and late S phase of the cell cycle. Also included among the natural antineoplastic agents are the antibiotic antineoplastic agents. Antibiotic antineoplastic agents are antimicrobial drugs that have anti-tumor properties usually through interacting with cancer cell DNA. Antibiotic antineoplastic agents suitable for use herein include, but are not limited to, belomycin, dactinomycin, doxorubicin, idarubicin, epirubicin, mitomycin, mitoxantrone, pentostatin, plicamycin, and their analogues and derivatives. The natural antineoplastic agent classification also includes camptothecin analogues and derivatives which are suitable for use herein and include camptothecin, topotecan, and irinotecan. These agents act primarily by targeting the nuclear enzyme topoisomerase I. Another subclass under the natural antineoplastic agents is the enzyme, L-asparaginase and its variants, L-asparaginase acts by depriving some cancer cells of L-asparagine by catalyzing the hydrolysis of circulating asparagine to aspartic acid and ammonia.

Hormonal antineoplastic agents act predominantly on hormone-dependent cancer cells associated with prostate tissue, breast tissue, endometrial tissue, ovarian tissue, lymphoma, and leukemia. Such tissues may be responsive to and dependent upon such classes of agents as glucocorticoids, progestins, estrogens, and androgens. Both analogues and derivatives that are agonists or antagonists are suitable for use in the present invention to treat tumors. Examples of glucocorticoid agonists/antagonists suitable for use herein are dexamethasone, cortisol, corticosterone, prednisone, mifepristone (RU486), their analogues and derivatives. The progestin agonist/antagonist subclass of agents suitable for use herein includes, but is not limited to, hydroxyprogesterone, medroxyprogesterone, megestrol acetate, mifepristone (RU486), ZK98299, their analogues and derivatives. Examples from the estrogen agonistiantagonist subclass of agents suitable for use herein include, but are not limited to, estrogen, tamoxifen, toremifene, RU58668, SR16234, ZD164384, ZK191703, fulvestrant, their analogues and derivatives. Examples of aromatase inhibitors suitable for use herein, which inhibit estrogen production, include, but are not limited to, androstenedione, formestane, exemestane, aminoglutethimide, anastrozole, letrozole, their analogues and derivatives. Examples from the androgen agonist/antagonist subclass of agents suitable for use herein include, but are not limited to, testosterone, dihydrotestosterone, fluoxymesterone, testolactone, testosterone enanthate, testosterone propionate, gonadotropin-releasing hormone agonists/antagonists (e.g. leuprolide, goserelin, triptorelin, buserelin), diethylstilbestrol, abarelix, cyproterone, flutamide, nilutamide, bicalutamide, their analogues and derivatives.

Angiogenesis inhibitors work by inhibiting the vascularization of tumors. Angiogenesis inhibitors encompass a wide variety of agents including small molecule agents, antibody agents, and agents that target RNA function. Examples of angiogenesis inhibitors suitable for use herein include, but are not limited to, ranibizumab, bevacizumab, SU11248, PTK787, ZK222584, CEP-7055, angiozyme, dalteparin, thalidomide, suramin, CC-5013, combretastatin A4 Phosphate, LY317615, soy isoflavones, AE-941, interferon alpha, PTK787/ZK 222584, ZD6474, EMD 121974, ZD6474, BAY 543-9006, celecoxib, halofuginone hydrobromide, bevacizumab, their analogues, variants, or derivatives.

Antibody agents bind targets selectively expressed in cancer cells and can either utilize a conjugate to kill the cell associated with the target, or elicit the body's immune response to destroy the cancer cells. Immunotherapeutic agents can either be comprised of polyclonal or monoclonal antibodies. The antibodies may be comprised of non-human animal (e.g. mouse) and human components, or be comprised of entirely human components ("humanized antibodies"). Examples of monoclonal irnmunotherapeutic agents suitable for use herein include, but are not limited to, rituximab, tosibtumomab, ibritumomab which target the CD-20 protein. Other examples suitable for use herein include trastuzumab, edrecolomab, bevacizumab, cetuximab, carcinoembryonic antigen antibodies, gemtuzumab, alemtuzumab, mapatumumab, panitumumab, EMD 72000, TheraClM hR3, 2C4, HGS-TR2J, and HGS-ETR2.

The process whereby cancer cells spread from the site of the original tumor to other locations around the body is termed cancer metastasis. Certain agents have anti-metastatic properties, designed to inhibit the spread of cancer cells. Examples of such agents suitable for use herein include, but are not limited to, marimastat, bevacizumab, trastuzumab, rituximab, erlotinib, MMI-166, GRN163L, hunter-killer peptides, tissue inhibitors of metalloproteinases (TIMPs), their analogues, derivatives and variants.

In some embodiments, treatment of cancer with the subject methods is accompanied by administration of pharmaceutical agents that can alleviate the side effects produced by the antineoplastic agents. Such agents suitable for use herein include,but are not limited to, anti-emetics, anti-mucositis agents, pain management agents, infection control agents, and anti-anemia/anti-thrombocytopenia agents. Examples of anti-emetics suitable for use herein include, but are not limited to, 5-hydroxytryptamine 3 receptor antagonists, metoclopramide, steroids, lorazepam, ondansetron, cannabinoids, their analogues and derivatives. Examples of anti-mucositis agents suitable for use herein include, but are not limited to, palifermin (keratinocyte growth factor), glucagon-like peptide-2, teduglutide, L-glutamine, amifostin, and fibroblast growth factor 20. Examples of pain management agents suitable for use herein include,but are not limited to, opioids, opiates, and non-steroidal anti-inflammatory compounds. Examples of agents used for control of infection suitable for use herein include, but are not limited to, antibacterials such as aminoglycosides, penicillins, cephalosporins, tetracyclines, clindamycin, lincomycin, macrolides, vancomycin, carbapenems, monobactams, fluoroquinolones, sulfonamides, nitrofurantoins, their analogues and derivatives. Examples of agents that can treat anemia or thrombocytopenia associated with chemotherapy suitable for use herein include, but are not limited to, erythropoietin, and thrombopoietin.

In combination therapy, an affibody may be administered with an immune response modulator. Alternatively, the anti-B7-H3 affibody can act as an immune checkpoint modulator itself. Immune checkpoint proteins are immune inhibitory molecules that act to decrease immune responsiveness toward a target cell, particularly against a tumor cell in the methods of the invention. Endogenous responses to tumors by T cells can be dysregulated by tumor cells activating immune checkpoints (immune inhibitory proteins) and inhibiting co-stimulatory receptors (immune activating proteins). The class of therapeutic agents referred to in the art as "immune checkpoint inhibitors" reverses the inhibition of immune responses through administering antagonists of inhibitory signals. Other immunotherapies administer agonists of immune costimulatory molecules to increase responsiveness.

The immune-checkpoint receptors that have been most actively studied in the context of clinical cancer immunotherapy, cytotoxic T-lymphocyte-associated antigen 4 (CTLA4; also known as CD152) and programmed cell death protein 1 (PD1; also known as CD279)—are both inhibitory receptors. The clinical activity of antibodies that block either of these receptors implies that antitumor immunity can be enhanced at multiple levels and that combinatorial strategies can be intelligently designed, guided by mechanistic considerations and preclinical models. Lymphocyte activation gene 3 (LAG3; also known as CD223), 2B4 (also known as CD244), B and T lymphocyte attenuator (BTLA; also known as CD272), T cell membrane protein 3 (TIM3; also known as HAVcr2), adenosine Ata receptor (A2aR) and the family of killer inhibitory receptors have each been associated with the inhibition of lymphocyte activity and in some cases the induction of lymphocyte anergy. Antibody targeting of these receptors can be used in the methods of the invention.

Agents that agonize an immune costimulatory molecule are also useful in the combination therapies. Such agents include agonists or CD40 and OX40. CD40 is a costimulatory protein found on antigen presenting cells (APCs) and is required for their activation. These APCs include phagocytes (macrophages and dendritic cells) and B cells. CD40 is part of the TNF receptor family. The primary activating signaling molecules for CD40 are IFNγ and CD40 ligand (CD40L). Stimulation through CD40 activates macrophages. One of the major effects of CD47 blocking agents is to enhance phagocytosis of target cells by macrophages and other phagocytes. Therefore, combining agonistic CD40 ligands with anti CD47 can enhance the therapeutic efficacy compared to each mono therapy (example 1). Agonistic CD40 agents may be administered substantially simultaneously with anti-CD47 agents; or may be administered prior to and concurrently with treatment with anti-CD47 to pre-activate macrophages. Anti CCR4 (CD194) antibodies of interest include humanized monoclonal antibodies directed against C—C chemokine receptor 4 (CCR4) with potential anti-inflammatory and antineoplastic activities. Exemplary is mogamulizumab, which selectively binds to and blocks the activity of CCR4, which may inhibit CCR4-mediated signal transduction pathways and, so, chemokine-mediated cellular migration and proliferation of T cells, and chemokine-mediated angiogenesis. In addition, this agent may induce antibody-dependent cell-mediated cytotoxicity (ADCC) against CCR4-positive T cells, CCR4, a G-coupled-protein receptor for C—C chemokines such MIP-1, RANTES, TARC and MCP-1, is expressed on the surfaces of some types of T cells, endothelial cells, and some types of neurons. CCR4, also known as CD194, may be overexpressed on adult T-cell lymphoma (ATL) and peripheral T-cell lymphoma (PTCL) cells.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Experimental

Example 1

According to the American Cancer Society, 266,120 women will be newly diagnosed with breast cancer and 40,920 associated deaths are estimated this year. Early detection is paramount to reducing patient mortality rates. Mammography is the first-line screening tool for early detection but its diagnostic accuracy is limited to only 5% of women with abnormal mammogram presenting real malignancy, especially in women with dense breast tissue. Conventional ultrasound is performed as a second line test in women with dense breast tissue but with a high number of false positives and unnecessary biopsies.

B7-H3 has been validated as a biomarker, which can be used as an ultrasound molecular imaging target differentially expressed on the neovasculature of human breast tumor compared to benign lesions and normal breast tissue (see FIG. 3). Microbubbles (MBs), typically used for contrast-enhanced ultrasound, can be functionalized with high-affinity binding ligands against molecular targets, such as B7-H3, on tumor vasculature to enable highly specific detection of cancer.

Provided herein is the development and analysis of a B7-H3-affibody peptide (affibody B7-H3) for uses that include without limitation targeted-contrast MBs and perform molecular ultrasound imaging in a transgenic breast cancer mouse model.

FIG. 2 shows the study design. A, Structure of the affibody peptide. B-D, overview of the overall study design. Microbubble-B7-H3-affibody was generated by covalently attaching the B7-H3-affibody peptide on the surface of microbubbles (MBs). C, molecularly-targeted MBs were tested both in vitro and D, in vivo in a transgenic mouse model of breast cancer followed by ex vivo quantitative immunofluorescence of B7-H3 expression on the tumor neovasculature. Ultrasound molecular imaging signal was measured using the destruction-replenishment technique.

An affibodyB7-H3 was engineered using the yeast display technique and was recombinantly expressed in E, coli. The affibodyB7-H3 was purified by fast protein liquid chromatography, and purity determined by SDS-PAGE and mass spectrometry. AffibodyB7-H3 was further validated for its specific binding to B7-H3-expressing vascular endothelial cell line in culture. The affibody peptide purification was performed in *E. coli* BL21, transformed with bacterial expression vector. A single bacterial colony grown on an LB plate supplemented with kanamycin (50 µg/mL) was inoculated into 5 mL of lysogeny broth (LB) media supplemented with kanamycin. After overnight culture, bacteria were transferred to 1 L of lysogeny broth (LB) media and grown at 30° C. and 250 rpm for 4 hours. Bacteria were further cultured at 37° C. and 250 rpm for 6 hours after 0.5 M isopropyl β-D-1-thiogalactopyranoside (IPTG) was added. The bacterial pellet was harvested via centrifugation at 3,200×g for 10 min, and was resuspended in 3 mL of ice-cold lysis buffer. The supernatant obtained by centrifugation at 12,000×g for 5 min were applied to a HisTrap FF column (GE Healthcare Biosciences, PA) in an AKTA FPLC system (GE Healthcare Biosciences), and 6xHis-tag B7-H3-affibodies were isolated and then lyophilized. The concentration of purified B7-H3-affibody protein was measured by UV spectrometry after dissolving in PBS. Evaluation of purity of the B7-H3-affibody was analyzed using SDS-PAGE electrophoresis. 30 μl of each purified protein and 6 μl of 5× reducing SDS loading buffer were added to 1.5 ml tubes and denatured at 96° C. for 5 minutes. The samples were run on SDS-PAGE gel in SDS running buffer at 30 mA for 2 hours. The gel was then stained with Coomassie Brilliant Blue for 1 hour and 3 subsequently destained for at least 12 hours with Coomassie destaining solution. The gel was visualized and analyzed using a BioRad Gel-Doc system.

The affibodyB7-H3-MBs were created by attaching affibodyB7-H3 to the shell of synthesized perfluorobutane-filled phospholipid MBs. Subsequently, the binding of affibodyB7-H3 -MBs to a soluble B7-H3 was assessed by flow cytometry. Non-targeted MBs and anti-B7-H3 antibody-decorated MBs (anti-B7-H3-MBs) were used as controls. All microbubble constructs were then tested for their molecular imaging capabilities in a transgenic breast cancer mouse model (FVB/N-Tg(MMTV-PyMT)634Mul/J).

The engineered affibodyB7-H3 showed a specific binding to B7-H3-cell lysate. For cell-binding assay, MS1 B7-H3+ cells were stained with streptavidin-APC-labeled B7-H3-affibody for 1 hour at 4° C. and analyzed with FACS. As negative control cells, MS1-WT, a negative cell line, was stained with streptavidin-APC-labeled B7-H3-affibody. B7-H3-affibody (with a concentration of 5-25 μM) showed binding to B7-H3-expressing cells, whereas there was no binding to B7-H3-negative cells (MS1-Control). Furthermore, blocking of B7-H3 receptors with free B7-H3-affibody resulted in significantly ($P<0.01$) decreased binding of fluorescently-labeled B7-H3-affibody, confirming binding specificity of B7-H3-affibody to cellularly B7-H3-expressing cells.

Compared to non-targeted MBs, in vitro flow analysis showed high-affinity binding to soluble B7-H3 using affibodyB7-H3 -MBs and anti-B7-H3-MBs, respectively. In vivo ultrasound molecular imaging of tumors (n=9) showed significantly higher signal following affibodyB7-H3-MBs (4.92±1.12 a.u.; $p<0.0004$) and anti-B7-H3-MBs (4.82±0.86 a,u.; $p<0.0001$) administration compared to the non-targeted MBs (0.15±0.05 a.u.). Ex vivo immunofluorescence staining of tumor sections confirmed B7-H3 expression on the neoangiogenic vessels of breast tumors.

Wild-type (WT) MILE SVEN 1 mouse vascular endothelial (MS1-WT or MS1 Control) cells were directly obtained directly from the American Type Culture Collection [(CRL2279; (ATCC)] that performs standard cell line characterizations of mycoplasma, yeast, bacterial, and viral contamination. The cell line was maintained according to the recommendations of the ATCC. Cells were cultured under sterile conditions in DMEM (ATCC) with FBS at 5% and maintained in a 5% CO2-humidified atmosphere at 37° C. Cells were transfected with human B7-H3 DNA. In brief, the human B7-H3 DNA sequence was first optimized for mammalian codon usage using standard techniques. The transfection of MS1-WT cells with the B7-H3-expression vector was performed using lipofectamine 2000 transfection reagent (Life Sciences; Invitrogen), following the recommended manufacturer's standard protocol. MS1 cells stably expressing human B7-H3 (MS1 B7-H3+) were grown in DMEM containing 10% FBS and 0.4 mg/mL puromycin (G418, Sigma) in a 5% CO2 humidified atmosphere and subcultured prior to confluence using trypsin.

Binding specificity of MB-B7-H3-affibody to the target B7-H3 was also assessed in cell culture experiments under flow shear stress conditions simulating flow in blood capillaries by using a parallel flow chamber experimental set-up (see FIG. 4). MS1 B7-H3+ cells between passages 2 and 4 were used in all experiments. Before flow chamber experiment, FACS analysis was performed in order to confirm B7-H3 expression of MS1 B7-H3+ cells. The geometric mean fluorescence intensity was determined using FlowJo software. MS1 B7-H3+ cells were grown on coated (Sigmacote; Sigma, St Louis, Mo) neutral-charged glass microscope slides (VWR, USA) for 24 hours and mounted on a parallel plate flow chamber (GlycoTech, Rockville, Md). A syringe infusion and withdrawal pump (Genie Plus; Kent Scientific, Torrington, Conn) was used to maintain the flow rate of 0.6 mL/min, corresponding to a wall shear stress rate of 100 sec-1, similar to that in tumor capillaries. The glass microscope slides were inverted and positioned in the parallel flow chamber apparatus in order to allow microbubbles to float and then bind to B7-H3-expressing cells. In brief, solutions were passed over cells in the following order; PBS for 2 minutes; $5×10^7$ of either MB-B7-H3-affibody, MB-anti-B7-H3-antibody, or MB-Non-targeted in PBS for 4 minutes; and finally washing with PBS for 2 minutes. The adhered microbubble number on the MS1 B7-H3+ cells monolayer was quantified manually by counting attached microbubbles on MS1 B7-H3+ cells with a phase-contrast bright-field microscope (Axiovert 25; Carl Zeiss, Thornwood, NY; original magnification, ×100) to assess the number of attached microbubbles per cell. At least five random fields of view of these slides were immediately imaged. Note that microbubbles can be visualized as small, rounded particles (yellow arrow) and were considered to be attached to MS1 B7-H3+ cells when there was direct contact with the cells without free floating. The flow chamber cell attachment study confirmed high binding specificity of MB-B7-H3-affibody to MS1 B7-H3+ cells. The average numbers of MB-B7-H3-affibody (8.52±1.42 MB/cell) and positive control MB-anti-B7-H3-antibody (9.79±1.34 MB/cell) attached per MS1 B7-H3+ cell were both significantly higher ($p<0.05$) than the average number of MB-Non-targeted attached (0.5±0.12 MB/cell). Furthermore,when comparing MB-B7-H3-affibody attachment to MS1 B7-H3+ cells versus MS1-WT cells, the average numbers of cell attachment to MS1-WT cells (0.57±0.18 MB/cell) was significantly lower ($p<0.05$) than to MS1 B7-H3+ cells.

Figure 6:
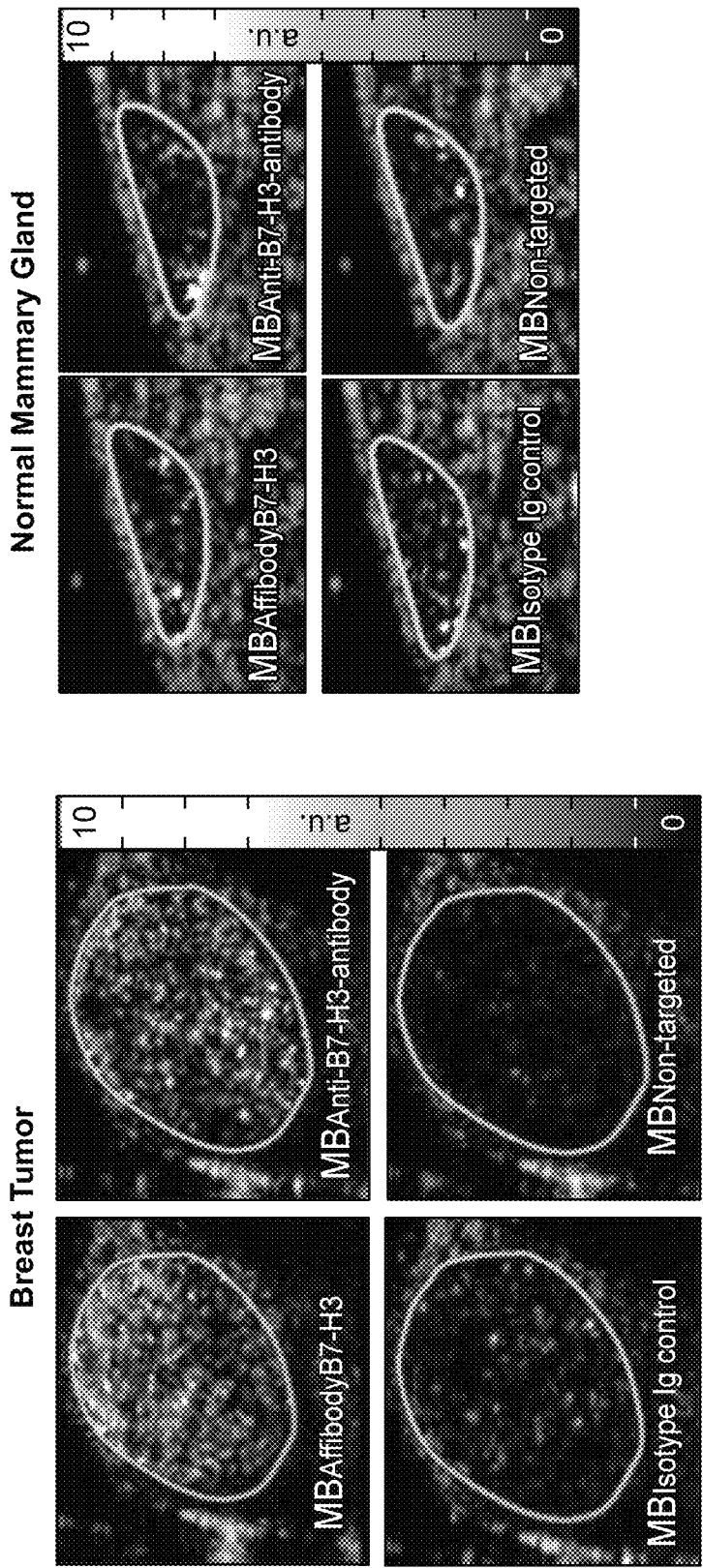

Shown in FIGS. 5 and 6 are in vivo ultrasound molecular imaging of transgenic breast cancer mouse model (FVB/N-Tg(MMTV-PyMT)634Mul/J) using MB-B7-H3-affibody. All experiments were approved by the Institutional Administrative Panel on Laboratory Animal Care. The transgenic mouse model of breast cancer development FVB/N-Tg (MMTV-PyMT)634Mul was used. The mammary tissue of this transgenic mouse model progresses through four distinct histological stages from normal mammary tissues, through hyperplasia, to ductal carcinoma in situ (DCIS), and finally invasive breast carcinoma which highly recapitulates human breast cancer.

For this study, inguinal mammary glands with invasive breast carcinoma were imaged by USMI (mean age, 7 weeks; range, 4-10 weeks) with 12 mammary tumors). Four control litter mates with normal mammary glands were used as controls. Mice were kept anesthetized with 2% isoflurane in oxygen at 2 Limin on a heated stage for 37° C. throughout the ultrasound imaging sessions. In an intra-animal comparison experiments, molecularly-targeted MBs ($5×10^7$ MB-B7-H3-affibody, MB-anti-B7-H3-antibody, and MB-Non-targeted) were injected intravenously through the tail vein of mice in random order to minimize any bias. Between imaging sessions using the three different contrast agents, a waiting interval of 30 min was used to allow for clearance of MBs from the vasculature. Also, at 30 min it was confirmed by USMI that no remaining MBs were present from the previous injection. In addition, control litter mates with normal mammary glands were scanned as tumor angiogenesis-negative models after the injection of all MB types to assess the contrast enhancement of non-angiogenic microvasculature. To further confirm binding specificity of molecularly-targeted MBs, an in vivo competition experiment was performed. In a subgroup of breast cancer-bearing mice, in vivo blocking of B7-H3 by injecting 100-150 μg B7-H3-affibody via the tail vein was performed in order to block binding of MB-B7-H3-affibody to its target B7-H3.

All in vivo imaging studies were performed in contrast mode using a small-animal high resolution ultrasound imaging system (Vevo2100; VisualSonics, Canada). Images were acquired with a 21-MHz high-resolution linear transducer (M5250, VisualSonics; lateral and axial resolution of 165 μm and 75 μm, respectively), and all imaging parameters (focal length, 8 mm; transmit power, 10%; mechanical index, 0.2; dynamic range, 40 dB and a center frequency of 18 MHz) were kept constant during all imaging sessions. The transducer was fixed on a railing system to maintain the acoustic focus at the center of the mammary gland at the level of the largest transverse cross section.

In vivo ultrasound molecular imaging results confirmed high binding specificity of MB-B7-H3-affibody to mouse tumors. In the transgenic mice with breast tumors, the targeted imaging signal of MB-B7-H3-affibody (5.45±1.18 a.u.) and MB-anti-B7-H3-antibody (6.22±2.50 a.u.) were both significantly higher (p<0.05) than that of MB-Non-targeted (0.49±0.12 a.u.) (FIGS. 1b & 1c), When comparing MBAf-B7-H3 imaging signal in transgenic mice tumors versus normal mice mammary glands, the imaging signal of MB-B7-H3-affibody in normal mice (1.26±0.37 a.u.) was significantly lower (p<0.05). To further confirm B7-H3-binding specificity of MB-B7-H3-affibody, in vivo blocking of B7-H3 receptors with free B7-H3-affibody was performed and showed significantly decreased imaging signal by ~60% compared to tumors without pre-administration of the blocking agent.

Examples of coding sequences for affibodies include without limitation:

```
1.4.0 Affibody B7-H3
                                          (SEQ ID NO: 22)
GCTAGCGCCGAAGCAAAATACGCTAAAGAAAAGATTTTTGCGGTTGGTGA

AATCTATTGGCTGCCGAACCTGACCCATGGTCAGATTATGGCATTCATAG

CGGCACTGAATGATGACCCGTCCCAGAGCTCTGAACTCCTGTCTGAGGCG

AAGAAACTGAACGATTCCCAAGCACCAAAAGGATCCCACCATCACCATCA

TCAC 1.2.6 Affibody B7-H3
                                          (SEQ ID NO: 23)
GCTAGCGCCGAAGCGAAATACGCTAAAGAAAGGCATCGGGCGTGGATGGA

AATCACGGGGCTGCCGAACCTGACCAGGCCTCAGCGTATTGCATTCATAC

TTGCACTGCGGGATGACCCGTCCCAGAGCTCTGAACTCCTGTCTGAGGCG

AAGAAACTGAACGATTCCCAAGCACCAAAAGGATCCCACCATCACCATCA

TCAC 1.2.7 Affibody B7-H3
                                          (SEQ ID NO: 24)
GCTAGCGCCGAAGCGAAATACGCTAAAGAATTTTCGTCTGCGCTTGTTGA

AATCTTGACTCTGCCGAACCTGACCCGGGCGCAGGTGGTCGCGCTCATGC

ATGCACTGCATAGCGACCCGTCCCAGAGCTCTGAACTCCTGTCTGAGGCG

AAGAAACTGAACGATTCCCAAGCACCAAAAGGATCCCACCATCACCATCA

TCAC
```

B7-H3 affibody peptides are a promising contrast agent for molecular ultrasound imaging and significantly improves breast cancer detection in a transgenic mouse model. Compared to monoclonal antibodies, affibody affords advantages of reduced molecular weight, potentially easier scale up for manufacturing and a clinically translatable platform. Thus, the design of a clinical-grade B7-H3-targeted ultrasound contrast agent may pave the way for reducing false positives and missed diagnoses of breast cancer, enabling rapid and effective detection of breast cancer at an early curable stage.

Example 2

Advances in genomic and proteomic methods have increased knowledge of disease biomarkers at a rate that has outpaced the development of new agents for diagnosis and therapy. Several classes of molecules can be applied to bridge this gap including engineered proteins. A variety of scaffolds have shown therapeutic effectiveness as inhibitors, targeting agents for drug delivery, radioisotope carriers, and immune system engagers and diagnostic success for early disease detection, patient stratification, and treatment monitoring.

Materials and Methods

Cells and Cell Culture. Mile Sven 1 cells stably transfected to express human CD276 (MS1-CD276) were kind gifts from Professor Juergen Willmann (Stanford University). All cell lines were grown at 37 °0 in a humidified atmosphere with 5% $CO_2$ in ©MEM with 4.5 g/L glucose, sodium pyruvate, and glutamine supplemented with 10% (v/v) fetal bovine serum.

Yeast surface display was performed essentially as described. EBY100 yeast harboring expression plasmids were grown in SD-CAA medium (16.8 g/L sodium citrate dihydrate, 3.9 g/L citric acid, 20.0 g/L dextrose, 6.7 giL yeast nitrogen base, 5.0 g/L casamino acids) at 30° C. with shaking. Protein expression was induced by transferring yeast cells in logarithmic phase ($OD_{600nm}$<6) into SG-CAA medium (10.2 g/L sodium phosphate dibasic heptahydrate, 8.6 g/L sodium phosphate monobasic monohydrate, 19.0 g/L galactose, 1.0 g/L dextrose, 6.7 g/L yeast nitrogen base, 5.0 g/L casamino acids) and growing at 30° C. with shaking for at least 8 hrs. EBY100 without plasmid were grown in YPD medium (10.0 g/L yeast extract, 20.0 g/L peptone, 20.0 g/L dextrose) at 30° C. with shaking.

Library Construction and Characterization. Oligonucleotides encoding for the second generation sitewise gradient affibody library were synthesized by IDT DNA Technologies. Full length amplicons for each respective library were assembled by overlap extension PCR and homologously recombined into pCT-40 yeast surface display vector within yeast stain EBY100 by electroporation transformation. Transformation efficiency was quantified by dilution plating on SD-CAA agar plates.

Proper library construction was characterized by simultaneous labeling of the N-terminal hemagglutinin (HA) epitope and C-terminal c-Myc epitope by flow cytometry. Two million yeast were pelleted at 12,000 g for 1 min, washed once with phosphate-buffered saline (PBS) with 1 g/L bovine serum albumin (PBSA), then labeled with mouse anti-c-Myc antibody 9E10 (1:1,000 dilution, BioLegend) and biotinylated goat anti-HA polyclonal antibody (1:500 dilution, Genscript) for 30 min at room temperature. Cells were washed once with 1 mL PBSA, labeled by goat anti-mouse Alexa Fluor 647 conjugate (1:1,000 dilution, Life Technologies) and streptavidin Alexa Fluor 488 conjugate (1:1,000 dilution, Life Technologies) for 15 min at 4° C., and washed once. Fluorescence was analyzed by flow cytometry (Accuri C6, BD Biosciences).

Magnetic Bead Selections with Soluble Extracellular Domains. Recombinant human CD276 extracellular domain (Sino Biological, Cat: 11188-H08H-B) was obtained in biotinylated form.

Magnetic bead selections were carried out as essentially previously described using 15-fold oversampling of ligand diversity at all stages. For the first round of selection, libraries were depleted of magnetic bead binders three times with streptavidin coated Dynabeads (Thermo Fisher Scientific, Cat: 11205D). Remaining yeast were incubated with CD276 coated magnetic beads at 4° C. and washed twice with ice cold PBSA. Beads with attached cells were resuspended in SD-CAA for growth. Magnetic beads were removed using a Dynal magnet prior to the induction of protein expression for the next round of selection. For subsequent rounds, non-specific binders were depleted with streptavidin coated magnetic beads and negative control protein coated magnetic beads prior to enrichment with target coated magnetic beads. Selections were carried out at room temperature and target-coated beads were washed three times with PBSA before regrowth of the attached yeast. Dilution plating on YPD plates of all negative control and target-coated bead populations was completed to quantify enrichment.

FACS with Soluble Extracellular Domains. Fluorescence-activated cell sorting (FACS) was carried out essentially as described. Induced yeast were simultaneously labeled with anti-c-Myc antibody and 10-100 nM biotinylated target protein or biotinylated negative control protein for at least 30 min at room temperature. Cells were washed once with PBSA, labeled with goat anti-mouse Alexa Fluor 647 conjugate and streptavidin Alexa Fluor 488 conjugate for 15 min at 4° C., and washed with 1 mL PBSA. Cells with the highest binding ligand display ratio (AlexaFluor488:AlexaFluor647) were sorted using a FACSAria (BD Bioscience).

FACS Selections with Detergent Solubilized Cell Lysates. Detergent solubilized cell lysates were prepared essentially as described. MS1-Thy1 and MS1-CD276 cells were grown to 70-90% confluence in 75 cm² tissue culture-treated T-flasks. Culture medium was removed and the cells were washed once with 5 mL PBS. Cells were detached by trypsin-EDTA treatment for 4-7 minutes, quenched with serum-containing culture medium, and centrifuged at 500 g for 3 min. Pelleted cells were washed three times with ice cold PBS and pelleted at 300 g for 3 min at 4° C. Washed cells were resuspended in PBS with 0.5 mg/mL fresh sulfo-NHS-biotin (Thermo Fisher Scientific), rotated for 30 min at room temperature, and washed twice with ice cold PBSA to quench and remove excess biotin. Cells were resuspended in 100-200 µL FACS lysis buffer (PBS with 1% (viv) Triton X-100, 2 mM EDTA, and 1× complete protease inhibitor cocktail (Roche)) and incubated with rotation at 4° C. for 15 min, Cell debris was pelleted at 15,000 g for 30 min at 4° C. and removed. Induced yeast were washed once with PBSA, then incubated with cell lysate and mouse anti-c-Myc antibody (2.5 µg/mL) simultaneously for 2 h at 4° C. with rotation. Yeast were washed with 1 mL ice cold PBS containing 1% (v/v) Triton-X 100 and then with 1 mL ice cold PBSA. Cells were incubated with goat anti-mouse Alexa Fluor 647 conjugate (10 µg/mL) and streptavidin Alexa Fluor 488 conjugate (2 µg/mL) at 4° C. for 15 min, and washed with 1 mL ice cold PBSA. Cells with the highest binding:ligand display ratio (AlexaFluor488:AlexaFluor647) were sorted using a FACSAria.

Yeast-Cell Panning Selections, Cell panning selections were carried out essentially as described. Mammalian cells were grown in 6-well plates to approximately 90% confluence. Culture medium was removed and cells were washed three times with ice cold PBSA with 1 mM CaCl$_2$ and 0.5 mM Mg$_2$SO$_4$ (PBSACM). For the first round of selection, 2.4×10⁹ yeast (six-fold diversity of Affibody library) were washed once with ice cold PBSACM, resuspended to 1×10⁸ yeast/mL in ice cold PBSACM, and applied to mammalian cells in 1 mL aliquots dropwise. Cells were incubated without shaking for 2 h at 4° C. and unbound yeast were removed by aspiration. Cells were washed with 1 mL ice cold PBSACM four times with 25 gentle tilts and 5 nutations and one time with 10 nutations. Bound yeast were recovered by scraping cell monolayers and resuspending them in SD-CAA growth medium. Yield was quantified by dilution plating on YPD plates. For each subsequent round, at least 15-fold of the recovered yield were washed and resuspended to no more than 1×10³ yeast/mL in ice cold PBSACM. Yeast were panned, in parallel, against one target-positive and two target-negative cell lines.

Clonal Characterization of Sorted Populations by Yeast-Cell Panning. Forty-eight colonies from each selection campaign, obtained by plating yeast populations on SD-CAA, were picked and resuspended in 1 mL SG-CAA in deep-well 96-well plates. Plates were covered and grown at 30° C. with shaking for at least 8 h.

Target-positive and target-negative mammalian cells were grown to approximately 80% confluence in 24-well plates. Cells were washed 3 times with ice cold PBSACM. 250 µL of induced clonal yeast was added dropwise directly to one well of target-positive and one well of target-negative mammalian cells. Cells were incubated without shaking for at least 2 h at 4° C. Cells were washed with 250 µL ice cold PBSACM twice with 25 gentle tilts and 5 nutations and once with 10 nutations. Yeast binding was visualized using EVOS FL Cell Imaging System (Thermo Fisher Scientific) at 40× total magnification. Individual clone binding was categorized as –, +, ++, or +++ through counting associated yeast in a random microscope field. Clones were characterized as "–" if fewer than 15 yeast were observed, "+" if 15 to 50 yeast were observed, "++" if greater than 50 yeast were observed but mammalian cells were still visible, and "+++" if yeast were the dominant organism seen in the frame.

DNA. Sequencing Plasmid DNA from yeast clones that bound target-positive but not target-negative cells was recovered by zymoprep of 200 µL of each individual clone. Ligand sequences were amplified in 50 µL PCR mixtures containing 2 µL zymoprep DNA, 1× Phusion High Fidelity buffer, 0.5 µM each of primers W5 and W3 (25), 0.2 mM dNTP mixture, and 2.5 U Phusion polymerase (New England Biolabs, Ipswich, Mass.). PCR products were purified by agarose gel electrophoresis and Sanger sequenced with GeneAmp5 primer (5'-CGACGATTGAAGGTAGATACC-CATACG-3') (Eurofins MWG Operon, Louisville, Ky.).

Error-Prone PCR of Affibody Domains. Random mutation of fibronectin domains and affibodies was performed essentially as described by error-prone PCR with nucleoside analogs. Zymoprepped plasmid DNA was mutated by error-prone PCR of full affibody genes using primers W5/W3, and affibody helicies using primers ABY1F-b/ABY1R and ABY2F/ABY2R-b. PCR products were purified by agarose gel electrophoresis, amplified in four 200 μL PCR mixtures, concentrated by ethanol precipitation, and resuspended in 30 μL buffer E several hours before electroporation. Mutated sublibraries were homologously recombined with linearized pCT-Gene (cut with NdeI, Pstl-HF, and BamHl-HF), or pCT-40-Helix (cut with SmaI, NcoI-HF, and NdeI) in EBY100 yeast by electroporation transformation as described. Transformation efficiency was quantified by dilution plating on SD-CAA plates.

Helix Walking Library Construction. CD276 rational mutagenesis libraries were constructed using an analogous method to CDR-walking. Affibody helix one was diversified while retaining parental helix two, and vice versa. The diversified oligonucleotide for one helix and parental oligonucleotide for the other helix were assembled by overlap extension PCR and homologously recombined into pCT yeast surface display vector within yeast strain EBY100 by electroporation transformation. Transformation efficiency was quantified by dilution plating on SD-CAA agar plates. Full-length library construction was characterized by flow cytometry as previously described.

Clone Production. Gel-purified PCR amplicons were digested by Nhel-HF and BamHl-HF (New England Biolabs) and ligated into a pET-22b vector containing a C-terminal His6 tag (Novagen, EMD Millipore, Billerica, MA) using T4 DNA ligase (New England Biolabs). Plasmids were transformed via heat-shock into T7 *E. coli* (New England Biolabs) and plated on lysogeny broth (LB) (10.0 μL tryptone, 5.0 g/L yeast extract, 10.0 g/L sodium chloride) agar plates containing kanamycin (50 mg/L). Clones were verified by Sanger sequencing of plasmids recovered by bacterial miniprep (Epoch Life Science, Sugar Land, TX).

*E. coli* were grown to saturation in 5 mL LB containing kanamycin at 37° C. with shaking. Cultures were diluted to $OD_{600}=0.03$ with 100 mL LB in 250 mL baffled culture flasks. At $OD_{600}=0.5$-1.0, protein expression was induced with 0.5 mM isopropyl β-D-1-thiogalactopyranoside overnight at 30° C. with shaking. Cells were pelleted at 3220 g for 20 min, resuspended in bacterial lysis buffer (50 mM sodium phosphate (pH 8.0), 0.5 M sodium chloride, 5% glycerol, 5 mM CHAPS, and 25 mM imidazole) and subjected to 5 freeze-thaw cycles. Insoluble cell debris was removed by centrifugation at 10,000 g for 10 min followed by filtration (0.2 μm). Protein was purified by metal affinity chromatography on 2 mL of Cobalt HisPur Resin according to the manufacturer's protocol (Thermo Fisher Scientific). Purity was assessed by SDS-PAGE using 4-12% bis-tris gels (Life Technologies, Carlsbad, CA), Protein concentration was quantified by absorbance at 280 nm (27).

Affinity Measurement. MS1-CD276 were grown to 70-90% confluence. Cells were washed once with 5 mL PBS, detached by trypsin-EDTA treatment for 4-7 min, quenched by the addition of serum-containing culture medium, pelleted at 500 g for 3 min, and resuspended in PBSACM Fifty thousand cells were pelleted at 500 g for 3 min at 4° C. and incubated with purified ligand at varying concentrations at 4° C. with rotation. Cells were washed once with ice cold PBSACM, pelleted at 500 g for 3 min, incubated with 1:200 dilution rabbit anti-His-tag FITC conjugate (pAb, Genscript) for 30 min at 4° C., washed once more with ice cold PBSACM, and again pelleted at 500 g for 3 min at 4° C. Fluorescence was analyzed by flow cytometry using an Accuri C6. Affibody affinity was determined through nonlinear least squares regression.

Example 3

Affibody Ligand Targeting Vascular B7-H3 for Early Detection of Breast Cancer by Ultrasound Molecular Imaging Smaller protein scaffolds enable efficient, site-specific conjugation and prokaryotic production and can replace antibodies (150 kDa) for MB functionalization. Recently, affibodies (ABY) have been shown to be a promising platform for designing binding ligands for molecular imaging. The ABY is a 58-amino-acid protein (~7 kDa) derived from the three alpha helix bundle Z domain of Staphyloccocus aureus protein A. Compared to antibodies, ABY exhibit faster renal clearance, greater stability at a wide range of physiological pH and temperature, are cost-effective for larger-scale production, and enable site-specific conjugation. ABY molecules are an alternative to full-length antibodies in diagnostic applications and have been validated pre-clinically and translated to clinical trials.

Breast cancer is the second leading cause of cancer deaths in women in the United States and its early detection is key to improving survival. While mammography is currently the modality of choice for breast cancer screening, its diagnostic accuracy is limited in women with dense breast tissue. Ultrasound (US) is often performed as a second-line test for dense breast tissue: however, due to its low specificity, US results in many false positive findings, leading to unnecessary biopsies. The ability of clinically translatable US molecular imaging to differentiate benign and malignant lesions in dense breast tissue is critically important, as it could improve the detection of clinically relevant disease while reducing overall costs, unnecessary biopsies, and patient anxiety associated with false-positive recalls. Towards this aim, we demonstrate the efficacy of affibody-based US molecular imaging of vascular B7-H3 expression in breast cancer animal models.

Purpose: Human B7-H3 (hB7-H3) is a promising molecular imaging target differentially expressed on the neovasculature of breast cancer and has been validated for pre-clinical ultrasound (US) imaging with anti-B7-H3-antibody functionalized microbubbles (MB). However, smaller ligands such as affibodies (ABY) are more suitable for the design of clinical-grade targeted-MB.

Experimental design: Binding of ABYB7-H3 (SEQ ID NO:1) was confirmed with soluble and cell-surface B7-H3 by flow-cytometry. MB were functionalized with ABYB7-H3 or anti-B7-H3-antibody (AbB7-H3). Control and targeted-MB were tested for binding to hB7-H3-expressing cells (MS1hB7-H3) under shear stress conditions. US imaging was performed with MBABY-B7-H3 in an orthotopic mouse model of human MDA-MB-231 co-implanted with MS1hB7-H3 or control MS1WT cells and a transgenic mouse model of breast cancer development.

Results: ABYB7-H3 specifically binds to MS1hB7-H3 and murine-B7-H3-expressing monocytes. MBABY-B7-H3 (8.5±1.4 MB/cell) and MBAb-B7-H3 (9.8±1.3 MB/cell) showed significantly higher (p<0.0001) binding to the MS1hB7-H3 cells compared to control MBNon-targeted (0.5±0.1 MB/cell) under shear stress conditions. In vivo, MBABY-B7-H3 produced significantly higher (p<0.04) imaging signal in orthotopic tumors co-engrafted with MS1hB7-H3 (8.4±3.3 a.u.) compared to tumors with MS1WT cells (1.4±1.0 a,u.). In the transgenic mouse tumors, MBABY-B7-H3 (9.6±2.0 au.) produced higher (p<0.0002) imaging signal compared to MBNon-targeted (1.3±0.3 a.u.), while MBABY-B7-H3 signal in normal mammary glands and tumors with B7-H3-blocking significantly reduced (p<0.02) imaging signal.

Conclusions: MBABY-B7-H3 (SEQ ID NO:1) enhances B7-H3 molecular signal in breast tumors, improving cancer detection, while offering the advantages of a small size ligand and easier production for clinical imaging.

The purpose of this proof-of-principle study is to utilize the engineered B7-H3-specific ABY protein (ABYB7-H3) conjugated to contrast MB, and to validate their use in vitro for endothelial cell binding under flow shear stress conditions, and assess specificity and sensitivity for US molecular imaging of tumor neovasculature in two different mouse models of breast cancer: human xenografts and transgenic models.

Methods

Human B7-H3 expression analysis. Human breast cancer samples for tissue staining were collected as described elsewhere and were obtained with written informed consent and institutional review board approval. RNA-Seq expression data for CD276 (B7-H3) and PECAM1 (CD31) in patient breast invasive carcinoma was downloaded from The Cancer Genome Atlas (TCGA) database and compared in PAM50 gene-expression based intrinsic breast cancer subtypes using UCSC Xena Browser.

Production of recombinant ABYB7-H3. ABYB7-H3 ligand was recombinantly expressed in *Escherichia coli* and purified by a HisTrap FF column (GE Healthcare Biosciences).

Preparation of targeted microbubbles. Commercially available perfluorocarbon-filled, lipid-shelled, streptavidin-coated contrast MB (VisualSonics) with a mean diameter of 1.5 µm (range, 1-3 µm) were reconstituted in 1 mL sterile saline (0.9% sodium chloride). Three types of MB were prepared: two MB with the ability to target both hB7-H3 (for xenograft tumor models) and mB7-H3 (for transgenic tumor models) were made by either conjugating MB with biotinylated ABYB7-H3 (MBABY-B7-H3) or a commercially available biotinylated anti-B7-H3 antibody (eBiosciences, clone M3.2D7,) (MBAb-B7-H3), and unconjugated MB (MBNon-targeted).

To create each targeted MB, lyophilized streptavidin coated MB were suspended in 1 mL of sterile saline according to the published recommendations. 6 pg of biotinylated ABY or antibody were incubated with $5 \times 10^7$ MB for 10 minutes at room temperature before use in in vitro and in vivo experiments. For the confirmation of ABY conjugation to MB, APC-anti-HisTag antibody (Biolegend) and biotin-ABY (incorporating His6 tag sequence) were first incubated together for 30 minutes to form a complex and then incubated with streptavidin MB for 10 minutes. Non-bound ligands were removed by centrifugation at 300 g for 2 min and washed in PBS. ABY-coated MB were then assessed for APC signal by flow cytometry (Guava easyCyte, Luminex).

Flow chamber cell attachment assay. Binding specificity of MBABY-B7-H3 and MBAb-B7-H3 to the target B7-H3 was first assessed in cell culture experiments under flow shear stress conditions simulating flow in blood capillaries by using a flow chamber experimental set-up. Please see Supplementary Methods for more details.

Two mouse models of breast cancer. All experiments were approved by the Institutional Administrative Panel on Laboratory Animal Care. An orthotopic human breast cancer model with tumors from MDA-MB-231 cells stably expressing firefly luciferase (f-luc) reporter gene mixed in matrigel with either MS1WT or MS1hB7-H3 cells expressing renilla luciferase (r-luc) reporter gene was used for establishing tumors in the contralateral flanks of nude (nu/nu) mice (The Jackson Laboratory). Reporter expression details are provided in the supplemental document.

$1 \times 10^6$ MDA-MB-231/f-luc cells were mixed with $5 \times 10^6$ MS1/r-luc cells and implanted on the fourth mammary glands: MS1hB7-H3ir-luc cell mixture on the left flank and MSIWT/r-luc cell mixture on the right flank. Imaging was performed in the nude mice after two weeks of tumor cell engraftment with a mean size of 4 mm (range, 3-5 mm).

In addition, the transgenic mouse model of breast cancer development FVB/N-Tg(MMTV-PyMT)634Mul was used (The Jackson Laboratory) (21). The mammary tissue of this transgenic mouse model progresses through four distinct histological stages from normal mammary tissues, hyperplasia, ductal carcinoma in situ, and finally invasive breast carcinoma which highly recapitulates human breast cancer. For this study, female mice (mean age, 7 weeks; range, 4-10 weeks) with 10 mammary glands with invasive breast carcinoma were imaged with a mean size of 7 mm (range 5-9 mm) by US molecular imaging. The litter mates with normal mammary glands were used as controls, In vivo imaging. Bioluminescence Imaging. Mice co-injected with MDA-MB-231/f-luc cells and MSI/r-luc cells were tested for successful implantation by bioluminescence imaging in live animals after two weeks of engraftment. Mice were subjected to intraperitoneal injection of 50 µL D-luciferin (30 mg/mL) substrate followed by anesthesia in 2% isoflurane in room air, and bioluminescence imaging (Lago in vivo Imaging System, Spectral Instruments Imaging) to confirm the growth of MDA-MB-231 tumors. After a 24-hour interval, anesthetized mice were injected with 150 µL of coelenterazine (5 mg/mL) substrate via tail vein injection followed by bioluminescence imaging to confirm the presence of MS1 cells within these tumors.

Ultrasound (US) molecular imaging. Contrast-enhanced US imaging was performed using a dedicated small-animal high resolution US imaging system (Veno 2100; VisualSonics). All mice were kept anesthetized with 2% isoflurane in room air at 2 L/min on a heated stage at 37° C. throughout the US molecular imaging sessions. Image acquisition was performed in the transverse plane using a high-resolution transducer (MS250; center frequency, 18MHz, lateral and axial resolution of 165 µm and 75 µm, respectively; focal length, 8 mm; transmit power, 10%; mechanical index, 0.2; dynamic range, 40 dB). Imaging was performed by fixing the transducer with a clamp and placing the acoustic focus at the center of the mammary tumors in the plane showing the largest transverse cross section. The same US settings and equipment were used for all imaging experiments, Recommendations for using targeted MB (MicroMarker, VisualSonics) for small animal imaging were followed as described elsewhere. US molecular signal (i.e. US contrast signal from vessel-bound MBABY-B7-H3) was obtained by the destruction-subtraction technique, and its signal specificity confirmed by comparisons with a positive control, MB coated with anti-B7-H3 antibody (MBAb-B7-H3), and a negative control, non-functionalized MB (MBNon-targeted). $5 \times 10^7$ MB (50 were injected intravenously via the tail vein in random order to minimize any bias from injection order. Targeted MB were allowed to attach to B7-H3 on the tumor neovasculature. After four minutes, 200 imaging frames were captured over a 15-second period and averaged to obtain imaging signal from adherent and freely circulating MB This was followed by a 1-second continuous high-power destructive pulse of 3.7 MPa (transmit power, 100%; mechanical index, 0.63) which destroyed all MB within the image. Ten seconds after the destruction pulse, another 200 imaging frames were acquired and averaged to capture the signal from the influx of freely circulating MB. The averaged images before and after bursting MB were then subtracted to determine the molecular imaging signal. The time between injection and imaging with different MB constructs was 20 minutes to allow for freely circulating MB to clear from the previous injection.

US data analyses, including breathing motion correction, defining the region of interest in mammary tissue, and differential targeted enhancement, were performed in Vevo LAB (Visual Sonics) software.

Statistical Analysis. Student's t-test was used to compare statistical significance between the experimental groups and all data were expressed as mean±standard error of mean. Experiments were considered significantly different if the P value was less than 0.05.

Results

Figures 9A, 9B:
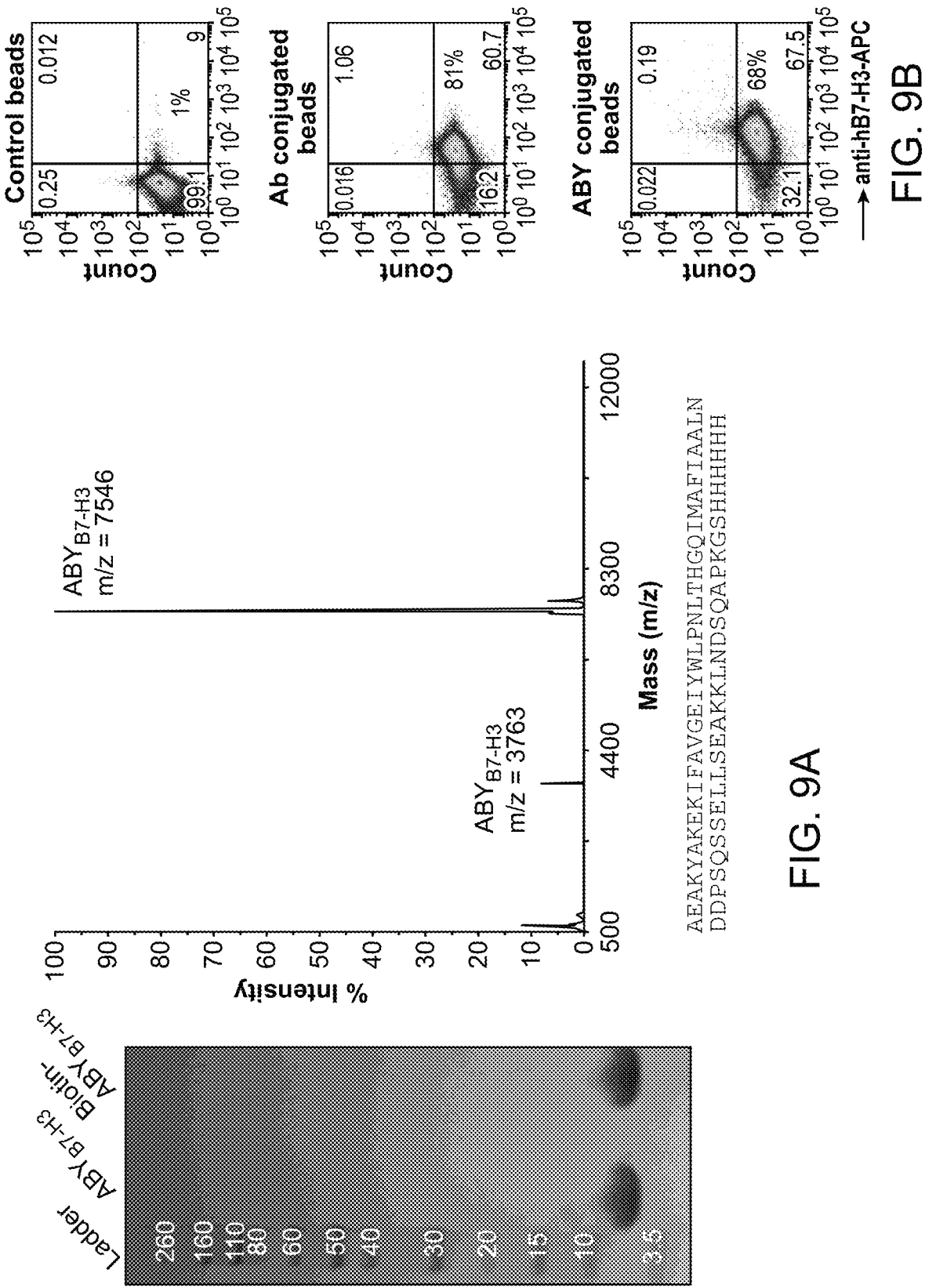
FIG. 9. Production and validation of $ABY_{B7-H3}$.(A) Left panel: Commassie Blue staining of SDS-PAGE showing high purity and expected size (7,490 Da) of finalized $ABY_{B7-H3}$ produced in E. Coli. Right panel: Mass spectrometric analysis of $ABY_{B7-H3}$ showing a mass-to-charge peak (m/z=7,546) corresponding to ABY molecular weight. A doubly charged peak (m/z=3763) is also present. Amino acid sequence of $ABY_{B7-H3}$ (SEQ ID NO:28) is shown on the bottom. (B) Flow cytometry of biotin-$ABY_{B7-H3}$ conjugated streptavidin-microbeads complex showing binding to soluble recombinant B7-H3 (3 μM) as detected by APC conjugated anti-B7-H3 antibody. Unconjugated beads (negative control) and anti B7-H3 antibody (AB) conjugated beads (positive control) were also tested for binding to soluble B7-H3 antigen.

B7-H3 expression in breast cancer, To compare gene expression of CD276 (B7-H3) in patient breast cancer samples against a pan-endothelial marker, PECAM1 (CD31), RNA-Seq expression data across PAM50 molecular breast cancer subtypes in the TCGA database were downloaded using the UCSC Xena web-based tool. Analysis showed higher CD276 expression in all breast cancer subtypes compared to the normal tissue, while the PECAM1 expression was higher in normal tissue compared to cancer tissue (FIG. 8A). As B7-H3 is expressed by both vascular endothelial cells and neoplastic cells, we tested its protein expression in patient tissue sections by immunohistochemical staining. In the representative samples, B7-H3 staining was observed in structures morphologically resembling blood vessels as well as the cancer cells independent of disease sub-types as seen by its increased staining in luminal, triple-negative, and Her2+breast cancer samples compared to a normal mammary tissue (FIG. 8B). Based on endothelial expression of B7-H3 in clinical tissue samples, experimental plans for clinically translatable targeted-microbubble (MB) contrast agent development and its use in contrast-enhanced US imaging of mouse models of breast cancer was formulated as the work flow in FIG. 1C, Production of ABYB7-H3. Development of a B7-H3-binding ligand from an ABY yeast display library is described in Example 1. The ABY ligand clone termed ABYB7-H3 with a Kd of 310±100 nM is used. ABYB7-H3 ligand was recombinantly expressed in E. coli, purified, and functionalized with 1:1 molar ratio of biotin. SDS-PAGE analysis of biologically produced ABY showed the predicted size of the ABY (expected: 7,490 Da), which was measured to be 7,546 Da by mass spectrometry (FIG. 9A). No impurities were observed in the purified ABY by SDS gel or mass spectrometry. In order to confirm binding specificity of recombinantly produced ABYB7-H3 to its target, biotinylated-ABY was immobilized to streptavidin- magnetic beads and incubated with 3 µM of recombinant soluble human B7-H3 ectodomain protein. Unconjugated beads (negative control) showed 1% binding compared to ABYB7-H3 conjugated beads, which showed 68% binding to the soluble B7-H3. The binding of ABYB7-H3 is comparable to the beads conjugated to biotinylated anti- B7-H3 antibody positive control, which had 81% binding (FIG. 9B).

ABYB7-H3 binds specifically to B7-H3. ABYB7-H3 binding to cells predominantly expressing 4Ig-B7-H3 (hB7-H3) isoform and mouse cells expressing 2Ig-B7-H3 (mB7-H3) isoform was tested. B7-H3 total protein as well as cell-surface expression was confirmed in MS1 mouse endothelial cells engineered to overexpress hB7-H3 (MS1hB7-H3) by western blotting and flow cytometry (FIG. 10A and B); only MS1hB7-H3 cells expressed B7-H3 protein, while both MS1WT and MS1hB7-H3 cells endogenously expressed CD31 protein, a common vascular endothelial marker, by western blot. Biotinylated ABYB7-H3 bound specifically to MS1hB7-H3 cells but not to MS1WT cells as detected by streptavidin-AF647 dye in flow cytometry (FIG. 10B), Similarly, ABYB7-H3 binds to the mouse monocyte cell line, RAW264.7, which endogenously expresses moderate levels of cell-surface mB7-H3 (FIG. 10C). ABYB7-H3 dose dependent increases in binding signal in both MS1hB7-H3 (0-10 µM) and RAW264.7 (0 25 µM) cells was observed, but not in the B7-H3-negative cells, MS1WT.

Because ABYB7-H3 binding to endogenously expressed hB7-H3 is critical for its clinical translation, a human monocytic cell line, THP1, was chemically induced for hB7-H3 expression by phorbol myristate acetate (PMA) to test for ABY binding. THP1 cells express a basal level of cell-surface hB7-H3, which was further increased upon stimulation by PMA (10 ng/mL) as detected by APC conjugated anti-B7-H3 antibody using flow cytometry (FIG. 10D). The increase in PMA-induced B7-H3 expression correlated with increased biotinylated ABYB7-H3 binding to THP1 cells as detected by streptavidin AF647 (FIG. 10D).

Figure 10E:
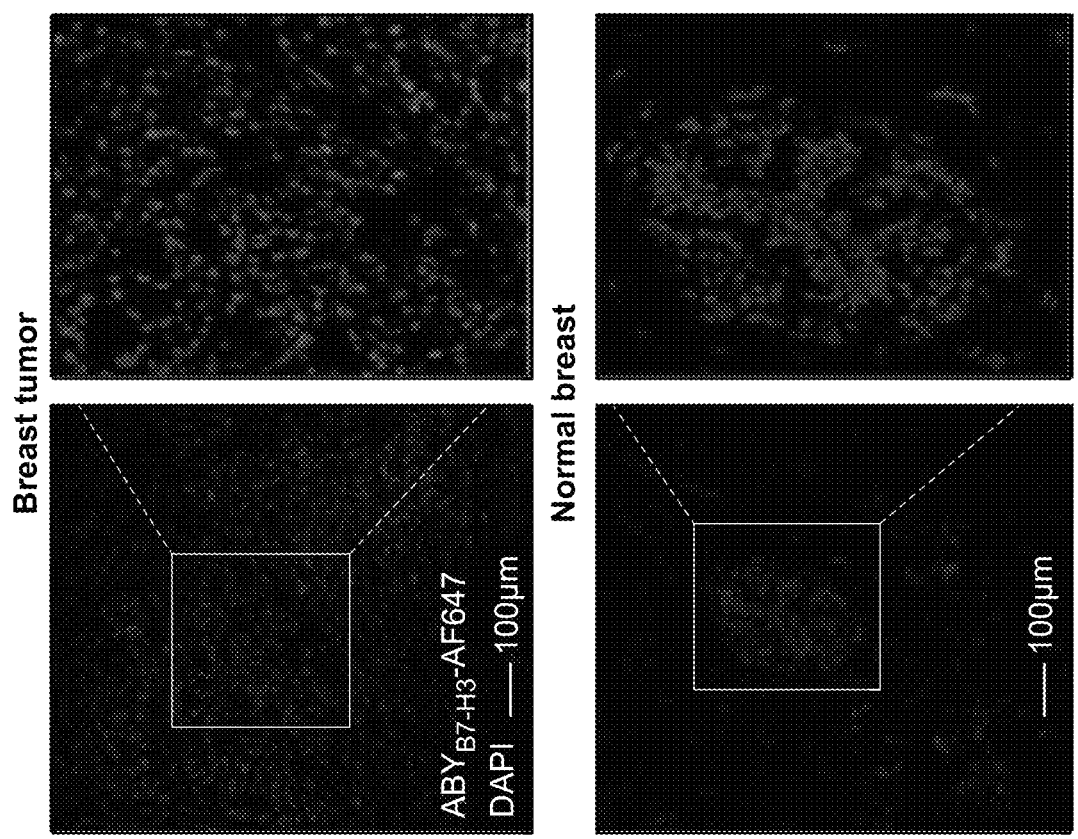
FIG. 10. $ABY_{B7-H3}$ binds to B7-H3-positive cells with high specificity in vitro. (A) Human B7-H3 protein overexpression in the cell lysate of stably transfected murine endothelial cells, $MS1_{hB7-H3}$, compared to that of MS1 wild-type ($MS1_{WT}$) cells by western blot with fluorescent detection. CD31 is an endothelial cell-specific maker and actin β is a protein loading control. Numbers below the protein bands indicate radiance (p/sec/cm$^2$/sr) of the expressed proteins. (B) Left panel: Histogram showing cell-surface hB7-H3 receptor expression in $MS1_{hB7-H3}$ cells compared to $MS1_{WT}$ r by flow cytometry using anti-hB7-H3-APC antibody (Ab) or no antibody control (Ctl,). Right panels: Biotin- $ABY_{B7-H3}$ (10 μM) binding specifically to $MS1_{hB7-H3}$ cells but not the $MS1_{WT}$ cells as detected by streptavidin-AF647 dye. (C) Cell surface staining of endogenous mB7-H3 in the mouse monocyte cell line, RAW264.7, using anti-mB7-H3 antibody compared to IgG control (Ctl.) antibody; histogram representation of biotin-$ABY_{B7-H3}$ (10 μM) binding to cells. (D) Histograms showing anti-hB7-H3 antibody or biotin-$ABY_{B7-H3}$ (10 μM) staining of THP1 human monocytic cell line chemically induced for B7-H3 expression with PMA (0 and 10 ng/mL). Unstained control (Ctl.) cells used as reference. (E) Immunofluorescence staining with $ABY_{BY-H3}$-AF647 (red) and a nuclear marker, DAPI (blue), in a human breast tumor and normal breast tissue sections. Scale bar represents 100 μm. Zoomed images of insets are shown on the right panel.

As post-translational modifications, including glycosylation of tissue-expressed B7-H3 receptors, can limit accessibility of engineered ligands or antibodies to the receptor binding pockets, ABY binding was tested in human breast tissue sections by immunofluorescence staining. ABYB7-H3 conjugated to AF647 dye stained positive for B7-H3 expressed on the cell-surface on the tumor tissue section (FIG. 10E). In contrast, ABYB7-H3 did not bind to normal breast tissue sections.

ABYB7-H3 coated microbubbles (MBABY-B7-H3) attach to B7-H3 expressed on endothelial cells. To mimic the in vivo shear stress that would occur on bound MB by blood flow in the capillaries, an in vitro flow chamber cell attachment assay of MB using MS1hB7-H3 cells was performed (FIG. 11A). Biotinylated ABY was conjugated to streptavidin MB (MBABY-B7-H3). A positive control group was included with biotinylated anti-B7-H3 antibody conjugated MB (MBAb-B7-H3), which were validated in previous studies. Unconjugated MB (MBNon-targeted) served as negative controls for quantification of non-specific binding to cells. The number of MBABY-B7-H3 (8.5±1.4 MB/ cell) and MBAb-B7-H3 (9.8±1.3 MB/ cell) attached to MS1hB7-H3 cells was significantly higher (p<0.0001) compared to the MBNon- targeted (0.5±0,1 MB/cell) (FIG. 11B and C). In contrast, a low number of all MB constructs attached to MS1WT cells. There was no significant difference between MBABY-B7-H3 (1.5±0.3 MB/cell; p<0.00001 vs. MS1hB7-H3) and MBNon-targeted (1.3±0.3 MB/ cell) attachment to the MS1WT cells. Furthermore, to determine the specificity of MBABY-B7-H3 to the cell-surface B7-H3, a receptor blocking study was performed by incubating MS1hB7-H3 cells with free ABYB7-H3 (5 µg/mL) prior to the cell attachment assay with MBABY-B7-H3. Blocking significantly (p<0.009) decreased the MBABY-B7-H3 attachment to cells (10.9±2.9 MB/ cell) compared to cells without blocking (26.3±4.4 MB/cell) (FIG. 11D). Overall, these results suggest that MBABY-B7-H3 is capable of binding specifically to human B7-H3-expressing cells under flow shear stress conditions.

MBABY-B7-H3 enhance B7-H3 ultrasound (US) molecular signal in breast tumors. To evaluate binding of MBABY-B7-H3 to both human and murine B7-H3 in vivo, both an orthotopic human breast cancer xenograft expressing hB7-H3 on its vasculature as well as a transgenic mouse model of spontaneous breast cancer expressing mB7-H3 on its neovasculature were used. US molecular imaging of tumors was conducted with all MB constructs in mice. After 2 weeks of tumor and endothelial cell co-engraftments in nude mice, in vivo bioluminescence imaging confirmed signal from MDA-MB-231/f-luc cancer cells from both flanks, MS1hB7-H3/r-luc endothelial cells on the left flank, and MS1WT/r-luc endothelial cells on the right flank (FIG. 12A). Luciferase reporter gene introduction into MS1 cells did not alter B7-H3 expression and bioluminescence activity was confirmed in vitro prior to in vivo use. US molecular imaging of the left tumors, consisting of MS1hB7-H3 cells, produced significantly higher molecular imaging signal with MBABY-B7-H3 (8.4±3.3 a.u.; n=12 tumors, *p<0.04) compared to the MBNon-targeted (1.4±1.0 a.u., n=14 tumors). The positive control MBAb-B7-H3 also produced high molecular imaging signal (8.2±1.3 a.u.; n=6, *p<0.001 vs. MBNon-targeted), similar to that from MBABY-B7-H3 (FIG. 12B and C). In the tumors consisting of MS1WT cells on the right flanks, the molecular imaging signal with MBABY-B7-H3 (1.6±0.6 a.u.), MBAb-B7-H3 (3.1±0.9 a.u.), and MBNon-targeted (0.6±0.2 a.u.) were low.

Of all the MB constructs tested for molecular imaging signal in the tumors with MS1WT cells, MBAb-B7-H3 produced the highest background imaging signal (*p<0,001 vs. MBNon-targeted). MBABY-B7-H3 (p<0.05) and MBAb-B7-H3 (p<0.008), but not MBNon-targeted, produced higher imaging signal in tumors consisting of MS1hB7-H3 cells compared to their respective MB constructs in the tumors consisting of MS1WT cells (FIG. 12B and C). Immunofluorescence co-staining with anti-mouse CD31 and anti-human B7-H3 antibodies confirmed the integration of MS1 cells on the mouse blood vessels as well as non-vascular compartments of the engrafted tumors (FIG. 12D). hB7-H3 expression was absent on the tumors engrafted with MS1WT cells.

After evaluation in the xenograft breast cancer model, we also tested targeted MBs in a MMTV-PyMT transgenic mouse model that spontaneously develops mammary tumors, which progress into highly invasive disease over time. MBABY-B7-H3 (9.6±2.0 a.u,; n=47 tumors, *p<0.0002) and MBAb-B7-H3 (7.2±1.8 a.u.; n=45 tumors, *p<0.001) produced significantly higher US molecular imaging signal from mammary tumors compared to the MBNon-targeted (1.3±0.3 a.u.; n=41 tumors) (FIG. 6A and C). In vivo blocking of the mB7-H3 receptors in the transgenic mice with free ABY (150 µg) 24 hours prior to tumor imaging resulted in significantly reduced molecular imaging signal (0.4±0.2 a,u.; n=5, *p<0.02) from tumors compared to the same animals imaged before blocking (4.3±1.0 a.u.) with the MBABY-B7-H3 (FIG. 13B and C). Also, as a negative control for nonangiogenic B7-H3-negative vessels, normal mammary glands in age-matched control littermates were scanned after intravenous administration of MBABY-B7-H3, MBAb-B7-H3, and MBNon-targeted. US imaging signal in normal mammary gland was low with all microbubble constructs (MBABY-B7-H3 (2.3±0.5 a.u.; n=14 glands), MBAb-B7-H3 (2.5±0.8 a.u.; n=10 glands) and MBNon-targeted (2.6±0.6 a.u.; n=15 glands) (FIG. 13D). B7-H3 expression on the CD31-positive vasculature of the transgenic mammary tumors was confirmed by immunofluorescence staining with anti-B7-H3 antibody. B7-H3 was not expressed in CD31-positive vasculature in the tissue sections derived from normal mammary glands. These results confirm that ABY is specific to both human and murine B7-H3 expressed on tumor endothelial cells in vivo and that MBABY-B7-H3 provides B7-H3 specific molecular imaging signal of breast tumors compared to the normal mammary tissue.

A clinically translatable contrast agent for US molecular imaging of breast cancer is provided. An engineered ABY protein ligand for a breast cancer-associated vascular marker, B7-H3, was applied to MB-based US molecular imaging for mammary tumor detection in mouse models. In vitro, ABYB7-H3 binds specifically to its soluble and cell-surface target overexpressed on the endothelial cells and mouse RAW264.7 or human THP1 monocyte cells that are known to endogenously express B7-H3, Targeting of MB contrast agent by bio-functionalization with surface conjugation of ABYB7-H3 significantly increased their attachment to endothelial cells under flow shear stress conditions. In vivo, B7-H3 targeting of MB (MBABY-B7-H3) significantly improved the blood vessel-associated US molecular imaging signal in tumors but not in the normal mammary glands. In vivo blocking of B7-H3 receptor significantly reduced the molecular imaging signal achieved with MBABY-B7-H3 further validating molecular specificity. The sensitivity and specificity of this molecular contrast agent provides for clinical translation for US detection of vascular B7-H3 expressing breast tumors, which could increase the sensitivity of US as a complementary imaging modality for accurate diagnosis of breast cancer in women, including those with mammographically dense breasts.

In recent years, US molecular imaging of tumor angiogenesis and inflammatory processes using MB-based contrast agents has made significant progress in biomarker-based detection of underlying pathology. For this study, B7-H3 (CD276) was selected as a biomarker for US molecular imaging as the expression of B7-H3 in tumor endothelial and epithelial compartments of breast cancer has been extensively reported in the literature. In our analysis, B7-H3 expression in the blood vessels as well as the cancer cells in human tissue sections of various breast cancer subtypes was upregulated compared to normal breast tissues. As B7-H3 expression is a sub-type independent biomarker of breast cancer angiogenesis and is downregulated in benign tumors of the breast tissue, it is an ideal biomarker for the development of a clinically translatable US contrast agent. As an example, a targeted MB contrast agent against another validated vascular marker, VEGFR2/KDR, has been used in anti-angiogenic therapy monitoring of colon cancer and recently, tested in the first-in-human trials with US signal correlating with histological VEGFR2 expression of patient tissue sections of breast and ovarian cancer. The current work expands the capacity for molecular profiling of breast cancer.

Previously, an US contrast agent composed of MBs functionalized with anti-B7-H3 antibody improved US imaging signal of mammary tumors expressing B7-H3 in the vasculature (Bachawal et al. Cancer Res 2015;75:2501-9), Instead of an antibody, the use of ABY is economical for large-scale synthetic production, which is a major advantage over the costs associated with development and production of humanized monoclonal antibodies. ABY have high stability, solubility, and ability to withstand high temperatures (90° C.) or acidic and alkaline conditions (pH 2.5 or pH 11, respectively). Moreover, the small, single-domain architectures of ABY allow for efficient site-specific chemical conjugations via incorporation of terminal amino acids such as a cysteine to functionalize contrast MB. ABYB7-H3 was developed based on multiple criteria encompassing affinity, specificity, solubility, and thermal stability that are crucial for its optimal function in vivo. ABY scaffolds are of clinical value for biomarker detection and safe for imaging use in humans.

ABYB7-H3 recognized both exogenously overexpressed human B7-H3 in endothelial cells as well as endogenously expressed mouse/human B7-H3 by monocyte cell lines in our in vitro experiments. ABYB7-H3 recognized B7-H3 expressed in breast cancer patient tissue sections, MBABY-B7-H3 bound specifically to the endothelial cells expressing human B7-H3 under flow shear stress conditions in vitro and tumor blood vessels of breast cancer mouse models. A crucial requirement for targeted MB is that they not only bind to the desired target but bind under shear stress from the expected forces on the MB from blood flow in capillaries. We have shown in an in vivo murine model of breast cancer that MBABY-B7-H3 enhanced US molecular imaging signal of MDA-MB-231 orthotopic tumors consisting of MS1hB7-H3 but not those consisting of MS1WT cells. MBABY-B7-H3 showed lower non-specific imaging signal compared to MBAb-B7-H3 in tumors implanted with MS1WT cells suggesting its ability to reduce background contrast signal in US. Immunofluorescence staining of tumor sections showed hB7-H3 staining in the CD31-positive tumor endothelium indicating incorporation of MS1hB7-H3 cells in angiogenic vessels during the growth of orthotopic tumors. Furthermore, MBABY-B7-H3 significantly increased imaging signal of spontaneously developed mammary tumors in transgenic mice but not the normal glands of control mice. Immunostaining of B7-H3 showed expression in CD31-positive blood vessels of mammary tumor tissue sections, while staining was negative in normal glandular tissue. Anecdotal evidence suggested that the in vivo B7-H3 receptor blocking with excess ABYB7-H3 prior to imaging with MBABY-B7-H3 significantly reduced US molecular imaging signal from tumors. These results indicate that MBABY-B7-H3 can not only differentiate a malignant tumor within the normal mammary tissue but also generates a highly specific molecular B7-H3 signal in tumors. Due to its affinity for both mouse and human isoforms of B7-H3, ABYB7-H3 allows for simultaneous optimization of MB contrast development for human use and testing in translational mouse models of breast cancer.

A clinical grade MBABY-B7-H3 contrast agent is suitable for breast cancer screening, and provides an ideal development for ultrasonic detection of mammographically occult malignancy in women with dense breast tissue. Full clinical translation may include safety testing of targeted MB use in patients, fine tuning the acoustic parameters for the MB constructs, and image processing or pulse sequencing for use in newer clinical US systems, such as the automated breast volume scanners that are capable of producing 3D images and lowering operator dependency or software beamforming systems that are capable of integrating new and more sensitive molecular imaging techniques. To date, the use of targeted and non-targeted contrast microbubbles has shown a very low number of adverse events in humans and had no nephrotoxic effects, which also means a patient is not required to perform renal function tests prior to MB administration as required before CT and MRI imaging methods. In addition, MBs show a low systemic toxicity profile in human subjects based on recent clinical trials on inoperable pancreatic cancer patients.

Less immunogenic chemical approaches are available for conjugating ABYB7-H3 to the MB, such as cysteine-maleimide conjugation used in the FDA approved antibody-drug conjugates and synthesis of MB from pre-formed lipid-ligand conjugates increasing their shelf life. Also, while this study was conducted with an adequate affinity ABY, a higher affinity ABY (Kd=0.9±0.6 nM) was developed, which can further increase the US molecular signal sensitivity and specificity. In pre-clinical US molecular imaging, high frequency US is used to delineate targeted imaging signal, which cannot be integrated in low frequency US systems used in clinic. Pre-clinical US systems are also poor in distinguishing background tissue signal from MB signal due to high echogenicity of tissue in a heterogeneous tumor microenvironment. Clinical-frequency, real-time molecular imaging methods that do not require the destruction-subtraction technique used here and improve the sensitivity of bound MB signals to background tissue signal and non-bound MB signals are necessary for clinical translation.

Our work is one step closer to achieving clinically translatable targeted MB for accurate breast cancer detection by US molecular imaging. The use of B7-H3 targeted US imaging can be expanded to monitoring breast cancer anti-angiogenic therapy, determining disease progression with non-invasive quantification of vascular B7-H3 expression as a proxy for tumor pathological state, and creating multi-targeted MB with other relevant disease markers for high contrast clinical images. More immediately, MBABY-B7-H3 will aid in the earlier cancer detection of breast cancer as a supporting tool for mammography.

What is claimed is:

1. A polypeptide comprising residues 1-36 of any one of SEQ ID NO:1, SEQ ID NO:2, SEQ ID NO:3, or SEQ ID NO:4.

2. The polypeptide of claim 1, operably joined to an affibody third helix sequence.

3. The polypeptide of claim 2, wherein the affibody third helix sequence is selected from any of SEQ ID NO:5-21.

4. A polypeptide of claim 1 comprising any one of SEQ ID NO: 1, SEQ ID NO: 2, SEQ ID NO: 3, or SEQ ID NO: 4.

5. The polypeptide of claim 1, comprising an imaging moiety.

6. The polypeptide of claim 5, wherein the imaging moiety comprises a radiography heavy metal, a radiation emitting moiety, or a positron emitting moiety.

7. The polypeptide of claim 5, wherein the imaging moiety comprises a positron emitting moiety, a magnetic resonance contrast moiety, an ultrasound contrast moiety, a microbubble, or an optically visible moiety.

8. The polypeptide of claim 7, wherein the optically visible moiety comprises a fluorescent moiety, a visible-spectrum dye, or a visible particle.

9. The polypeptide of claim 1, comprising a cytotoxic moiety.

10. The polypeptide of claim 9, wherein the cytotoxic moiety comprises a radioactive isotope.

11. The polypeptide of claim 9, wherein the cytotoxic moiety comprises a chemotoxic agent or a toxin protein.

12. The polypeptide of claim 1, comprising an immunoglobulin Fc sequence.

13. The polypeptide of claim 1, comprising a pharmacokinetic moiety.

14. A contrast agent comprising a microbubble conjugated to a polypeptide of claim 1.

15. A pharmaceutical composition comprising the polypeptide of claim 1, and a pharmaceutically acceptable excipient.

16. A nucleic acid comprising a nucleotide sequence encoding the polypeptide of claim 1, optionally in an expression vector.

17. An isolated host cell comprising the nucleic acid of claim 16.

18. A method of imaging the presence of B7-H3 expressing cells, the method comprising:
 (a) contacting one or more cells with an effective dose of a polypeptide comprising: any one of SEQ ID NO:1, SEQ ID NO:2, SEQ ID NO:3, SEQ ID NO:4; and an imaging moiety, thereby forming a complex, and (b) detecting the complex, wherein detection of the complex is indicative of the presence of B7-H3 expressing cells.

19. The method of claim 18, wherein the imaging is performed in vivo.

20. The method of claim 18, wherein the cells are human cells.

21. The method of claim 18, wherein the B7-H3 expressing cells are endothelial cells of tumor vasculature or cancer cells.

22. The method of claim 18 wherein the B7-H3 expressing cells are vascular endothelial cells of human breast cancer.

23. The method of claim 18 wherein the polypeptide is conjugated to a microbubble; administered by parenteral injection; and the complex with B7-H3 is detected by ultrasound in vivo.

24. The method of claim 22, wherein the imaging is of a mammographically occult malignancy in women with dense breast tissue.

25. The method of claim 18, wherein the imaging is performed by any of ultrasound, positron emission tomography (PET), magnetic resonance imaging (MRI), computerized tomography (CT) scan, single photon emission computed spectroscopy (SPECT), or radiography.

26. A method of treating B7H3-positive cancer, the method comprising contacting B7-H3 positive cancer cells with an effective dose of a polypeptide comprising:
   any one of SEQ ID NO:1, SEQ ID NO:2, SEQ ID NO:3, SEQ ID NO:4; and
   a cytotoxic moiety.

* * * * *

SEQUENCE LISTING

```
<160> NUMBER OF SEQ ID NOS: 28

<210> SEQ ID NO 1
<211> LENGTH: 58
<212> TYPE: PRT
<213> ORGANISM: Artificial Sequence
<220> FEATURE:
<223> OTHER INFORMATION: Synthetic Sequence

<400> SEQUENCE: 1

Ala Glu Ala Lys Tyr Ala Lys Glu Lys Ile Phe Ala Val Gly Glu Ile
1               5                   10                  15

Tyr Trp Leu Pro Asn Leu Thr His Gly Gln Ile Met Ala Phe Ile Ala
            20                  25                  30

Ala Leu Asn Asp Asp Pro Ser Gln Ser Ser Glu Leu Leu Ser Glu Ala
        35                  40                  45
```

Lys Lys Leu Asn Asp Ser Gln Ala Pro Lys
    50                  55

<210> SEQ ID NO 2
<211> LENGTH: 58
<212> TYPE: PRT
<213> ORGANISM: Artificial Sequence
<220> FEATURE:
<223> OTHER INFORMATION: Synthetic Sequence

<400> SEQUENCE: 2

Ala Glu Ala Lys Tyr Ala Lys Glu Lys Ile Ala Leu Ser Glu Ile
1               5                   10                  15

Ile Trp Leu Pro Asn Leu Thr His Gly Gln Ile Met Ala Phe Ile Ala
            20                  25                  30

Ala Leu Asn Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 3
<211> LENGTH: 58
<212> TYPE: PRT
<213> ORGANISM: Artificial Sequence
<220> FEATURE:
<223> OTHER INFORMATION: Synthetic Sequence

<400> SEQUENCE: 3

Ala Glu Ala Lys Tyr Ala Lys Glu Lys Ile Ala Ala Leu Ser Glu Ile
1               5                   10                  15

Ile Trp Leu Pro Asn Leu Thr His Gly Gln Ile Met Ala Phe Ile Ala
            20                  25                  30

Ala Leu Asn Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 4
<211> LENGTH: 58
<212> TYPE: PRT
<213> ORGANISM: Artificial Sequence
<220> FEATURE:
<223> OTHER INFORMATION: Synthetic Sequence

<400> SEQUENCE: 4

Ala Glu Ala Lys Tyr Ala Lys Glu Lys Val His Ala Leu Ser Glu Ile
1               5                   10                  15

Ile Trp Leu Pro Asn Leu Thr His Gly Gln Ile Met Ala Phe Ile Ala
            20                  25                  30

Ala Leu Asn Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 5
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 5

```
Asp Pro Ser Gln Ser Ala Glu Leu Leu Ala Glu Ala Lys Lys Leu Asn
1               5                   10                  15

Asp Ala Gln Ala Pro Lys
            20
```

<210> SEQ ID NO 6
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 6

```
Asp Pro Ser Gln Ser Ala Asn Leu Leu Ala Glu Ala Lys Lys Leu Asn
1               5                   10                  15

Asp Ala Gln Ala Pro Lys
            20
```

<210> SEQ ID NO 7
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 7

```
Asp Pro Ser Gln Ser Ala Asn Leu Leu Ser Glu Ala Lys Lys Leu Asn
1               5                   10                  15

Glu Ser Gln Ala Pro Lys
            20
```

<210> SEQ ID NO 8
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 8

```
Asp Pro Ser Gln Ser Ala Asn Val Leu Gly Glu Ala Lys Lys Leu Asn
1               5                   10                  15

Asp Ser Gln Ala Pro Lys
            20
```

<210> SEQ ID NO 9
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 9

```
Asp Pro Ser Gln Ser Ala Asn Val Leu Gly Glu Ala Gln Lys Leu Asn
1               5                   10                  15

Asp Ser Gln Ala Pro Lys
            20
```

<210> SEQ ID NO 10
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 10

-continued

Asp Pro Ser Gln Ser Ser Asn Leu Leu Ser Glu Ala Lys Lys Leu Asn
1               5                   10                  15

Glu Ser Gln Ala Pro Lys
            20

<210> SEQ ID NO 11
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 11

Asp Pro Ser Gln Ser Thr Asn Val Leu Gly Glu Ala Lys Lys Leu Asn
1               5                   10                  15

Glu Ser Gln Ala Pro Lys
            20

<210> SEQ ID NO 12
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 12

Asp Pro Ser Val Ser Lys Glu Ile Leu Ala Glu Ala Lys Lys Leu Asn
1               5                   10                  15

Asp Ala Gln Ala Pro Lys
            20

<210> SEQ ID NO 13
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 13

Asp Pro Ser Val Ser Lys Glu Ile Leu Ala Glu Ala Lys Lys Leu Asn
1               5                   10                  15

Glu Ser Gln Ala Pro Lys
            20

<210> SEQ ID NO 14
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 14

Asp Pro Ser Gln Ser Ala Asn Leu Leu Ala Glu Ala Lys Lys Leu Asn
1               5                   10                  15

Asp Ala Gln Ala Pro Lys
            20

<210> SEQ ID NO 15
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 15

Asp Pro Ser Gln Ser Ala Asn Leu Leu Ser Glu Ala Lys Lys Leu Asn
1               5                   10                  15

Glu Ser Gln Ala Pro Lys
            20

<210> SEQ ID NO 16
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 16

Asp Pro Ser Gln Ser Ala Asn Val Leu Gly Glu Ala Gln Lys Leu Asn
1               5                   10                  15

Asp Ser Gln Ala Pro Lys
            20

<210> SEQ ID NO 17
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 17

Asp Pro Ser Gln Ser Thr Asn Val Leu Gly Glu Ala Lys Lys Leu Asn
1               5                   10                  15

Glu Ser Gln Ala Pro Lys
            20

<210> SEQ ID NO 18
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 18

Asp Pro Ser Val Ser Lys Glu Ile Leu Ala Glu Ala Lys Lys Leu Asn
1               5                   10                  15

Asp Ala Gln Ala Pro Lys
            20

<210> SEQ ID NO 19
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 19

Asp Pro Ser Val Ser Lys Glu Ile Leu Ala Glu Ala Lys Lys Leu Asn
1               5                   10                  15

Glu Ser Gln Ala Pro Lys
            20

<210> SEQ ID NO 20
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 20

Asp Ser Ser Gln Ser Ala Asn Val Leu Gly Glu Ala Gln Lys Leu Asn
1               5                   10                  15
Asp Ser Gln Ala Pro Lys
            20

<210> SEQ ID NO 21
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 21

Asp Pro Ser Gln Ser Ser Glu Leu Leu Ser Glu Ala Lys Lys Leu Asn
1               5                   10                  15
Asp Ser Gln Ala Pro Lys
            20

<210> SEQ ID NO 22
<211> LENGTH: 204
<212> TYPE: DNA
<213> ORGANISM: Artificial Sequence
<220> FEATURE:
<223> OTHER INFORMATION: Synthetic Sequence

<400> SEQUENCE: 22
gctagcgccg aagcaaaata cgctaaagaa aagatttttg cggttggtga aatctattgg      60
ctgccgaacc tgacccatgg tcagattatg cattcatag cggcactgaa tgatgacccg     120
tcccagagct ctgaactcct gtctgaggcg aagaaactga acgattccca agcaccaaaa    180
ggatcccacc atcaccatca tcac                                           204

<210> SEQ ID NO 23
<211> LENGTH: 204
<212> TYPE: DNA
<213> ORGANISM: Artificial Sequence
<220> FEATURE:
<223> OTHER INFORMATION: Synthetic Sequence

<400> SEQUENCE: 23
gctagcgccg aagcgaaata cgctaaagaa aggcatcggg cgtggatgga aatcacgggg     60
ctgccgaacc tgaccaggcc tcagcgtatt gcattcatac ttgcactgcg ggatgacccg    120
tcccagagct ctgaactcct gtctgaggcg aagaaactga acgattccca agcaccaaaa    180
ggatcccacc atcaccatca tcac                                           204

<210> SEQ ID NO 24
<211> LENGTH: 204
<212> TYPE: DNA
<213> ORGANISM: Artificial Sequence
<220> FEATURE:
<223> OTHER INFORMATION: Synthetic Sequence

<400> SEQUENCE: 24
gctagcgccg aagcgaaata cgctaaagaa ttttcgtctg cgcttgttga aatcttgact     60
ctgccgaacc tgacccgggc gcaggtggtc gcgctcatgc atgcactgca tagcgacccg    120
tcccagagct ctgaactcct gtctgaggcg aagaaactga acgattccca agcaccaaaa    180
ggatcccacc atcaccatca tcac                                           204

```
<210> SEQ ID NO 25
<211> LENGTH: 37
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (10)..(10)
<223> OTHER INFORMATION: Xaa can be selected from I, V, L, A, and F.
<220> FEATURE:
<221> NAME/KEY: MISC_FEATURE
<222> LOCATION: (11)..(11)
<223> OTHER INFORMATION: Xaa can be selected from I, V, A, F, and H.
<220> FEATURE:
<221> NAME/KEY: MISC_FEATURE
<222> LOCATION: (13)..(13)
<223> OTHER INFORMATION: Xaa can be selected from I, V, L, A, and F.
<220> FEATURE:
<221> NAME/KEY: MISC_FEATURE
<222> LOCATION: (14)..(14)
<223> OTHER INFORMATION: Xaa can be selected from G and S.
<220> FEATURE:
<221> NAME/KEY: MISC_FEATURE
<222> LOCATION: (18)..(18)
<223> OTHER INFORMATION: Xaa can be selected from Y and I.

<400> SEQUENCE: 25

Ala Glu Ala Lys Tyr Ala Lys Glu Lys Xaa Xaa Ala Xaa Xaa Ser Glu
1               5                   10                  15

Ile Xaa Trp Leu Pro Asn Leu Thr His Gly Gln Ile Met Ala Phe Ile
            20                  25                  30

Ala Ala Leu Asn Asp
        35

<210> SEQ ID NO 26
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 26
cgacgattga aggtagatac ccatacg                                            27

<210> SEQ ID NO 27
<211> LENGTH: 36
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (10)..(10)
<223> OTHER INFORMATION: Xaa can be selected from I or V.
<220> FEATURE:
<221> NAME/KEY: MISC_FEATURE
<222> LOCATION: (11)..(11)
<223> OTHER INFORMATION: Xaa can be selected from F, I, A, or H.
<220> FEATURE:
<221> NAME/KEY: MISC_FEATURE
<222> LOCATION: (13)..(11)
<223> OTHER INFORMATION: Xaa can be selected from L or V.
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: Xaa can be selected from G or S.
<220> FEATURE:
```

```
<221> NAME/KEY: MISC_FEATURE
<222> LOCATION: (17)..(17)
<223> OTHER INFORMATION: Xaa can be selected from Y or I.

<400> SEQUENCE: 27

Ala Glu Ala Lys Tyr Ala Lys Glu Lys Xaa Xaa Ala Xaa Xaa Glu Ile
1               5                   10                  15

Xaa Trp Leu Pro Asn Leu Thr His Gly Gln Ile Met Ala Phe Ile Ala
            20                  25                  30

Ala Leu Asn Asp
        35

<210> SEQ ID NO 28
<211> LENGTH: 66
<212> TYPE: PRT
<213> ORGANISM: Artificial Sequence
<220> FEATURE:
<223> OTHER INFORMATION: Synthetic Sequence

<400> SEQUENCE: 28

Ala Glu Ala Lys Tyr Ala Lys Glu Lys Ile Phe Ala Val Gly Glu Ile
1               5                   10                  15

Tyr Trp Leu Pro Asn Leu Thr His Gly Gln Ile Met Ala Phe Ile Ala
            20                  25                  30

Ala Leu Asn Asp Asp Pro Ser Gln Ser Ser Glu Leu Leu Ser Glu Ala
        35                  40                  45

Lys Lys Leu Asn Asp Ser Gln Ala Pro Lys Gly Ser His His His
    50                  55                  60

His His
65
```